United States Patent
Wu et al.

(10) Patent No.: US 10,463,721 B2
(45) Date of Patent: Nov. 5, 2019

(54) ENGINEERED CHIMERIC PEGYLATED ADI AND METHODS OF USE

(71) Applicant: TDW Group, Taipei (TW)

(72) Inventors: Bor-Wen Wu, San Diego, CA (US); Robert Almassy, Vista, CA (US); Wei He, San Diego, CA (US); Richard E. Showalter, El Cajun, CA (US); Jiaojuan He, Shanghai (CN); Yunyun Guo, Shanghai (CN); James A. Thomson, San Diego, CA (US)

(73) Assignee: TDW Group, Grand Cayman (KY)

(*) Notice: Subject to any disclaimer, the term of this patent is extended or adjusted under 35 U.S.C. 154(b) by 247 days.

(21) Appl. No.: 15/125,833

(22) PCT Filed: Mar. 18, 2015

(86) PCT No.: PCT/US2015/021189
§ 371 (c)(1),
(2) Date: Sep. 13, 2016

(87) PCT Pub. No.: WO2015/143006
PCT Pub. Date: Sep. 24, 2015

(65) Prior Publication Data
US 2017/0000862 A1    Jan. 5, 2017

Related U.S. Application Data

(60) Provisional application No. 61/954,929, filed on Mar. 18, 2014.

(51) Int. Cl.
*A61K 38/50* (2006.01)
*C12N 9/78* (2006.01)
*A61K 45/06* (2006.01)

(52) U.S. Cl.
CPC .............. *A61K 38/50* (2013.01); *A61K 45/06* (2013.01); *C12N 9/78* (2013.01); *C12Y 305/03006* (2013.01); *Y02A 50/401* (2018.01); *Y02A 50/491* (2018.01)

(58) Field of Classification Search
None
See application file for complete search history.

(56) References Cited

U.S. PATENT DOCUMENTS

| | | | |
|---|---|---|---|
| 5,372,942 A | 12/1994 | Mcgarrity et al. | |
| 5,474,928 A | 12/1995 | Takaku et al. | |
| 5,804,183 A | 9/1998 | Filpula et al. | |
| 6,132,713 A | 10/2000 | Fiipula et al. | |
| 6,180,387 B1 | 1/2001 | Biswas et al. | |
| 6,183,738 B1 | 2/2001 | Clark | |
| 6,635,462 B1 | 10/2003 | Ensor et al. | |
| 7,204,980 B2 | 4/2007 | Clark | |
| 7,323,167 B2 | 1/2008 | Clark et al. | |
| 7,413,735 B2 | 8/2008 | Min et al. | |
| 9,333,268 B2 | 5/2016 | Bomalaski et al. | |
| 9,789,170 B2 | 10/2017 | Showalter et al. | |
| 2003/0215429 A1 | 11/2003 | de Simone | |
| 2004/0258675 A1 | 12/2004 | Ensor et al. | |
| 2005/0129706 A1 | 6/2005 | Clark | |
| 2006/0002915 A1 | 1/2006 | Min et al. | |
| 2007/0198198 A1 | 8/2007 | Burczynski et al. | |
| 2007/0212311 A1 | 9/2007 | Burne et al. | |
| 2009/0238813 A1 | 9/2009 | Georgiou et al. | |
| 2010/0197944 A1 | 8/2010 | Palle et al. | |
| 2010/0303893 A1 | 12/2010 | Luo et al. | |
| 2011/0111403 A1 | 5/2011 | Petrauskene et al. | |
| 2011/0301189 A1 | 12/2011 | Khattar et al. | |
| 2012/0015049 A1 | 1/2012 | Zhang | |
| 2012/0148559 A1 | 6/2012 | Georgiou et al. | |
| 2013/0052179 A1 | 2/2013 | Huang et al. | |
| 2014/0348814 A1 | 11/2014 | Almassy et al. | |
| 2015/0132278 A1 | 5/2015 | Bomalaski et al. | |
| 2015/0231272 A1 | 8/2015 | Bomalaski et al. | |
| 2016/0074487 A1 | 3/2016 | Showalter et al. | |

FOREIGN PATENT DOCUMENTS

| | | |
|---|---|---|
| EP | 1987838 B1 | 1/2016 |
| JP | 2001-524836 | 12/2001 |
| JP | 2006-515281 | 5/2006 |
| JP | 2009-523433 | 6/2006 |
| KR | 10-2004-0004449 | 1/2004 |
| WO | WO 1998/051784 A1 | 11/1998 |
| WO | WO 2001/083774 A2 | 11/2001 |
| WO | WO 2002/044360 A2 | 6/2002 |
| WO | WO 2004/046309 A2 | 6/2004 |
| WO | WO 2013/151568 A1 | 10/2013 |
| WO | WO 2014/151982 A2 | 9/2014 |
| WO | WO 2015/143006 A1 | 9/2015 |
| WO | WO 2016/044376 A1 | 3/2016 |

OTHER PUBLICATIONS

Office Action for U.S. Appl. No. 14/214,040, dated Aug. 18, 2017, 25 pages.
Office Action for U.S. Appl. No. 14/214,040, dated Mar. 30, 2018, 15 pages.
Office Action for U.S. Appl. No. 14/214,040, dated Nov. 1, 2018, 28 pages.
Inada, et al., "Modification of Proteins with Polyethylene Glycol Derivatives." Methods in Enzymology (1994); 242: 65-90, 26 pages.
Rashotte, et al., "Daily Cycles in Body Temperature, Metabolic Rate, and Substrate Utilization in Pigeons: Influence of Amount and Timing of Food Consumption." Physiology & Behavior (1995); 57 (4): 731-746.
Schummer, et al., "The Proton Gradient Across Mycoplasma Membranes." Current Microbiology (1981); 5: 371-374.
Scopes and Smith, "Analysis of Proteins". In: Current Protocols in Molecular Biology (2006); John Wiley & Sons, Inc., Ch. 10, 10.0.1-10.0.22, Supplement 76, 22 pages.

(Continued)

*Primary Examiner* — Suzanne M Noakes
(74) *Attorney, Agent, or Firm* — Cooley LLP

(57) ABSTRACT

Provided are chimeric arginine deiminases, including pegylated chimeric arginine deiminases, and related compositions and methods of use thereof, including methods of treating cancer.

23 Claims, No Drawings
Specification includes a Sequence Listing.

(56) References Cited

OTHER PUBLICATIONS

[Author Unknown] UniProtKB/TrEMBL Submission A7LHN6_9MOLU (Sep. 11, 2007), retrieved from the Internet Jun. 12, 2018, 1 page, http://uniprot.org/uniprot/A7LHN6.txt?version=1.

[Author Unknown] UniProtKB/TrEMBL Submission A5YRS4_9MOLU (Jul. 10, 2007), retrieved from the Internet Jun. 12, 2018, 1 page, http://uniprot.org/uniprot/A5YRS4.txt?version=1.

[Author Unknown] UniProtKB/TrEMBL Submission D4XVN8_9MOLU (Jun. 15, 2010), retrieved from the Internet Jun. 12, 2018, 1 page, http://uniprot.org/uniprot/ D4XVN8.txt?version=1.

[Author Unknown] UniProtKB/TrEMBL Submission F9UJU2_9MOLU (Oct. 19, 2011), retrieved from the Internet Jun. 12, 2018, 1 page, http://uniprot.org/uniprot/ F9UJU2.txt?version=1.

Office Action for U.S. Appl. No. 14/214,040, dated Oct. 18, 2016, 19 pages.

Office Action for U.S. Appl. No. 14/855,661, dated Feb. 13, 2017, 15 pages.

International Preliminary Report on Patentability for International Application No. PCT/US2015/050354, dated Mar. 21, 2017, 6 pages.

Baxalta US Inc., Westlake Village, CA, Oncaspar, U.S. Food and Drug Administration Product Label, 8 pages, (Revised 2015).

De Angelis, M., et al., "Arginine Catabolism by Sourdough Lactic Acid Bacteria: Purification and Characterization of the Arginine Deiminase Pathway Enzymes from Lactobacillus sanfranciscensis CB 1." Applied and Environmental Microbiology, vol. 68, No. 12, Dec. 2002, pp. 6193-6201.

Fenske, J.D., and Kenny, George E. "Role of arginine deiminase in growth of Mycoplasma hominis." Journal of bacteriology 126.1 (1976): 501-510.

Kim, J., et al., "Expression, purification, and characterization of arginine deiminase from Lactococcus lactis ssp. lactis ATCC7962 in Escherichia coli BL21," Protein Expr. Purif. (2007), doi:10.1016/j.pep.2006.12.002, 7 pages.

Singapore Application No. 201307953-8, Search Report and Written Opinion dated Jan. 26, 2016, 9 pages.

CAS Registry search "Pegargiminase", performed Aug. 10, 2017, 3 pages.

NLM search https://chem.nlm.nih.gov/chemidplu&/rn/1394129-74-8 and "ADI-PEG 20" performed Aug. 2017, 1 page.

Toxnet search "Pegargiminase", search initially performed Aug. 2017 and results accessed Oct. 11, 2017, 2 pages.

Extended European Search Report for European Application No. 15765975.6, dated Oct. 27, 2017, 6 pages.

UniProtKB/TrEMBL Submission A7LHN6_9MOLU (Sep. 11, 2007), retrieved from the Internet Jun. 12, 2018, 1 page, http://uniprot.org/uniprot/A7LHN6.txt?version=1.

UniProtKB/TrEMBL Submission A5YRS4_9MOLU (Jul. 10, 2007), retrieved from the Internet Jun. 12, 2018, 1 page, http://uniprot.org/uniprot/A5YRS4.txt?version=1.

UniProtKB/TrEMBL Submission D4XVN8_9MOLU (Jun. 15, 2010), retrieved from the Internet Jun. 12, 2018, 1 page, http://uniprot.org/uniprot/ D4XVN8.txt?version=1.

UniProtKB/TrEMBL Submission F9UJU2_9MOLU (Oct. 19, 2011), retrieved from the Internet Jun. 12, 2018, 1 page, http://uniprot.org/uniprot/ F9UJU2.txt?version=1.

Zalipsky and Lee, Polyethylene Glycol Chemistry: Biotechnical and Biomedical Applications, J. M. Harris, ed., Plenum Press, NY, Chapter 21, pp. 347-370 (1992).

Extended European Search Report for European Application No. 14769340.2, dated Jun. 16, 2016, 9 pages.

Office Action for U.S. Appl. No. 14/214,040, dated Dec. 1, 2015, 21 pages.

Office Action for U.S. Appl. No. 14/214,040, dated May 16, 2016, 17 pages.

International Search Report and Written Opinion for International Application No. PCT/US2012/039979, dated Nov. 5, 2012, 12 pages.

International Preliminary Report on Patentability for International Application No. PCT/US2012/039979, dated Oct. 7, 2014, 8 pages.

International Search Report and Written Opinion for International Application No. PCT/US2015/021189, dated Jun. 25, 2015, 9 pages.

International Preliminary Report on Patentability for International Application No. PCT/US2015/021189, dated Sep. 20, 2016, 6 pages.

International Search Report and Written Opinion for International Application No. PCT/US2014/026766, dated Oct. 24, 2014, 14 pages.

International Preliminary Report on Patentability for International Application No. PCT/US2014/026766, dated Sep. 15, 2015, 9 pages.

International Search Report and Written Opinion for International Application No. PCT/US2015/050354, dated Dec. 18, 2015, 7 pages.

Ascierto, P. A. et al., "Pegylated Arginine Deiminase Treatment of Patients with Metastitic Melanoma: Results from Phase I and II Studies," Journal of Clinical Oncology, 23(30):7660-7668 and Erratum p. 4047 (2005).

Avramis, V. I. et al., "Pharmacokinetic/Pharmacodynamic Relationships of Asparaginase Formulations," Clin Pharmacokinet, 44(4):367-393 (2005).

Bi, D. et al., Isolation and identification of mycoplasmas from pigeons, Chinese Journal of Animal Poultry and Infectious Diseases, 19(6):1-5 (1997) [and English translation].

Bowles, T. et al., "Pancreatic Cancer Cell Lines Deficient in Argininosuccinate Synthetase are Sensitive to Arginine Deprivation by Arginine Deiminase," Int. J. Cancer, 128(8):1950-1955 (2008).

Cantor et al., "Therapeutic enzyme deimmunization by combinatorial T-cell epitope removal using neutral drift." Proc Natl Acad Sci USA, Jan. 5, 2011, vol. 108, No. 4, pp. 1272-1277.

Chen, N. et al., "Autophagy and tumorigenesis," FEBS Letters 584:1427-1435 (2010).

Das et al., "Crystal structures of arginine deiminase with covalent reaction intermediates implications for catalytic mechanism." Structure, Apr. 2004, vol. 12, No. 4, pp. 657-667.

Daylami, R. et al., "Abstract 4847: Arginine Deprivation by PEG-ADI Induces Autophagic Cell Death and Enhances the Tumor Suppression Effect of Gemcitabine in Pancreatic Cancer," Cancer Research, 70:4847 (2010).

Delage, B. et al., "Abstract 4445: Pegylated arginine deiminase induces mitochondrial apoptosis and synergizes with cisplatin in ASS1-negative malignant pleural mesothelioma," In: Proceedings of the 101st Annual Meeting of the American Association for Cancer Research, Apr. 17-21, 2010, Washington, DC, Philadelphia, PA: AACR; Cancer Research, 70(8 Suppl):Abstract nr 4445 (2010), 2 pages.

Delage, B. et al., "Arginine Deprivation and Argininosuccinate Synthetase Expression in the Treatment of Cancer," International Journal of Cancer, 126:2762-2772 (2010).

Ensor, C. M. et al., "Pegylated Arginine Deiminase (ADI-SS PEG20,000 mw) Inhibits Human Melanomas and Hepatocellular Carcinomas in Vitro and in Vivo," Cancer Research, 62(19):5443-5450 (2002).

Feun, L. et al., "Arginine Deprivation as a Targeted Therapy for Cancer," Current Pharmaceutical Design, 14:1049-1057 (2008).

Feun, L. et al., "Pegylated arginine deiminase: a novel anticancer enzyme agent," Expert Opin. Investig. Drugs., 15(7):815-822 (2006).

Fu, C. H. et al., "PEG-asparaginase," Expert Opinion Pharmacotherapy, 8(12):1977-1984 (2007).

Gallego, Pablo, et al. "Structural characterization of the enzymes composing the arginine deiminase pathway in Mycoplasma penetrans." PloS One (2012); 7.10: e47886.

Glazer, E. et al., "Phase II Study of Pegylated Arginine Deiminase for Nonresectable and Metastatic Hepatocellular Carcinoma," Journal of Clinical Oncology, 28(13):2220-2226 (2010).

Gong, H. et al., "Arginine Deiminase Inhibits Proliferation of Human Leukemia Cells More Potently than Asparaginase by Inducing Cell Cycle Arrest and Apoptosis," Leukemia, 14:826-829 (2000).

Guo, Zisheng, et al. "Genome sequence of Mycoplasma columbinum strain SF7." Genome Announcements (2013); 1.2: e00157-13.

(56) References Cited

OTHER PUBLICATIONS

Guo, Zisheng, et al. Mycoplasma columbinum Strain SF7 genome translation from Guo et al, Genome Announcements (2013); 1.2: e00157-13, 64 pages.
Guven, K. et al., "Cisplatin and Carboplatin Combination as Second-Lind Chemotherapy in Dacarbazine-Resistant Melanoma Patients," Melanoma Research, 11:411-415 (2001).
He, W. et al., "Abstract 4703: Lack of Expression of Argininosuccinate Synthetase in Human Cancer Tissue: A Biomarker for Sensitivity to Arginine Depetion with Pegylated Arginine Deiminase," Cancer Research, 70, Proceedings: AACR 101st Annual Meeting 2010—Apr. 17-21, 2010, 2 pages.
Henningham et al., "Structure-informed design of an enzymatically inactive vaccine component for group A *Streptococcus*." MBio, Jul./Aug. 2013, vol. 4, No. 4, pii: e00509-13.
Hernandez, C. et al., "Pegylated Arginase I: A Potential Therapeutic Approach in T-ALL," Blood, 115(25):5214-5221 (2010).
Holtsberg, F. W. et al., "Poly(ethylene glycol) (PEG) Conjugated Arginine Deiminase: Effects of PEG Formulations on its Pharmacological Properties," Journal of Controlled Release, 80:259-271 (2002).
International Pharmaceutical Excipients Council Japan (ed.), lyakutenkabutsu Jiten [Pharmaceutical Excipient Dictionary] 2007, Yakuji Nippo Limited, Jul. 25, 2007, p. 220-221.
Izzo, F. et al., "Pegylated Arginine Deiminase Treatment of Patients With Unresectable Hepatocellular Carcinoma: Results From Phase I/II Studies," Journal of Clinical Oncology, 22(10):1815-1822 (2004).
Kelly, M., et al., Abstract 4519: Small Cell Lung Cancers Lack Expression of Argininosuccinate Synthase (ASS) and are sensitive to Arginine Deprivation Using Arginine Deiminase-PEG20 (ADI-PEG20), Cancer Research, 70, AACR 101st Annual Meeting, Apr. 17-21, 2010, 2 pages.
Kelly, M. P. et al., "Arginine Deiminase PEG20 Inhibits Growth of Small Cell Lung Cancers Lacking Expression of Argininosuccinate Synthetase," British Journal of Cancer, 106(2):324-332 (2012).
Kim, R. H. et al., "ADI, Autophagy and Apoptosis: Metabolic Stress as a Therapeutic Option for Prostate Cancer," Autophagy, 5(4):567-568 (2009).
Kim, R. H. et al., "Arginine Deiminase as a Novel Therapy for Prostate Cancer Induces Autophagy and Caspase-Independent Apoptosis," Cancer Research, 69(2):700-708 (2009).
Komada, Y., et al., "Apoptoptic Cell Death of Human T Lymphoblastoid Cells Induced by Arginine Deimanse," International Journal of Hematology, 65:129-141 (1997).
Kung, C., et al., "Autophagy in Tumor Suppression and Cancer Therapy," Critical Reviews in Eukaryotic Gene Expression, vol. 21, No. 1, 2011, pp. 71-100.
NCBI Acc# 4E4J_A from Gallego et al, 2012. Alignment with SEQ ID No. 8, 2 pages.
Ni, Y. et al., "Arginine Deiminase, a Potential Anti-Tumor Drug," Cancer Letters 261:1-11 (2008).
Ni et al., "Rapid evolution of arginine deiminase for improved anti-tumor activity," Appl Microbiol Biotechnol., Jan. 11, 2011, vol. 90, No. 1, pp. 193-201.
Noh, E-J. et al., "Arginine Deiminase Enhances Dexamethasone-Induced Cytotoxicity in Human T-Lymphoblastic Leukemia CCFR-CEM Cells," Int. J. Cancer, 112:502-508 (2004).
Ohno, T. et al., "Argininosuccinate Synthetase Gene Expression in Leukemias: Potential Diagnostic Marker for Blastic Crisis of Chronic Myelocytic Leukemia," Leukemia Research, 16(5):475-483 (1992).
Poteete and Hardy, "Genetic Analysis of Bacteriophage T4 Lysozyme Structure and Function." Journal of Bacteriology, 176(22): 6783-6788 (1994).
Rodriguez, C. O. et al., "Abstract 4848: Pegylated arginine deiminase induces autophagy in canine melanoma and canine osteosarcoma," In: Proceedings of the 101st Annual Meeting of the American Association for Cancer Research, Apr. 17-21, 2010, Washington, DC, Philadelphia, PA: AACR Cancer Research, 70(8 Suppl.): Abstract nr 4848 (2010), 2 pages.
Savaraj, N., et al., "Arginine Deprivation, Autophagy, Apoptosis (AAA) for the Treatment of Melanoma," Current Molecular Medicine 2010, vol. 10, pp. 405-412.
Shen, L., et al., "Drug Evaluation: ADI-PEG-20—a PEGylated Arginine Deiminase for Arginine-Auxotrophic Cancers," Current Opinon in Molecular Therapeutics, 2006, vol. 8, No. 3, pp. 240-248.
Singapore Application No. 11201507354Q, Search Report and Written Opinion dated Oct. 10, 2016, 16 pages.
Sugimura, K., et al., "Tumor Growth Inhibitory Activity of a Lymphocyte Blastogenesis Inhibitory Factor," Cancer Research, 50, Jan. 15, 1990, pp. 345-349.
Sugimura, K., et al., "Elevated Argininosuccinate Synthetase Activity in Adult T Leukemia Cell Lines," Leukemia Research, vol. 14, No. 10, 1990, pp. 931-934.
Sugimura et al., "Polymorphism in genes for the enzyme arginine deiminase among *Mycoplasma* species." Infect. Immun. Jan. 1, 1993, vol. 61, No. 1, pp. 329-331.
Szlosarek, P., et al., "Abstract 4067: Pegylated Arginine Deiminase (ADI-PEG20) as a Potential Novel Therapy for Argininosuccinate Synthetase-Deficient Acute Myeloid Leukemia," Proceedings of the 102nd Annual Meeting of the American Associate for Cancer Research, Apr. 2-6, 2011, vol. 71, No. 8 (Supp), 2 pages.
Szlosarek, P., et al., "In Vivo Loss of Expression of Argininosuccinate Synthetase in Malignant Pleural Mesothelioma is a Biomarker for Susceptibility to Arginine Depletion," Cancer Therapy: Preclinical, Clin Cancer Research, vol. 12, No. 23. Dec. 1, 2006, pp. 7123-7131.
Szlosarek, P., et al., "Effect of Inactivation of Argininosuccinate Synthetase on Sensitivity of Lymphomas to Caspase-Dependent Apoptosis Following Treatment with Arginine Deiminase," Journal of Clinical Oncology, vol. 28. No. 15 (May 20 Supp), 2010, 2 pages.
USPTO in house BLAST alignment ADI-PEG 20 (the variant of SEQ ID No. 1 herein consisting of the substitutions K112E and P21OS) alignment with SEQ ID No. 8. Performed May 10, 2016.
Wang, M. et al., "Engineering an arginine catabolizing bioconjugate: Biochemical and pharmacological characterization of PEGylated derivatives of arginine deiminase from mycoplasma arthritidis," Bioconjugate Chem., 17:1447-1459 (2006).
Weickmann and Fahrney. "Arginine deiminase from Mycoplasma arthritidis. Evidence for multiple forms." Journal of Biological Chemistry (1977); 252.8: 2615-2620.
Yang, T., et al., "A Randomised Phase II Study of Pegylated Arginine Deiminase (ADI-PEG 20) in Asian Advanced Hepatocellular Carcinoma Patients," British Journal of Cancer, vol. 103, 2010, pp. 954-960.
You, M. et al., "Abstract 61: Enhancing Arginine Deprivation Therapy in Melanoma by Combining with Cisplatin," In: Proceedings of the 101st Annual Meeting of the American Association for Cancer Research, Apr. 17-21, 2010, Washington, DC, Philadelphia, PA: AACR Cancer Research; 70(8 Suppl.):Abstract nr 61, (2010), 2 pages.
You, M. et al., "Abstract #3418: Arginine Deprivation and Soluble TRAIL Strikingly Enhance Death in Argininosuccinate Synthetase Negative Melanoma Cells," Proc. Am. Assoc. Cancer Research; Apr. 18-22, 2009, 2 pages.
You, M., et al., "Abstract 4096: TRAIL Enhances Cytotoxicity of Arginine Depletion Therapy in Argininosuccinate Synthetase-Negative Melanoma Cells Through Interruption of Autophagy Via Activation of Caspases," Proceedings of the 102nd Annual Meeting of the American Association for Cancer Research; Apr. 2-6, 2011, Cancer Research 2011, vol. 71, No. 8 (Supp), 2 pages.
You, M., et al., "The Combination of ADI-PEG20 and TRAIL Effectively Increases Cell Death in Melanoma Cell Lines," Biochemical and Biophysical Research Communications, 394:760-766 (2010).
Zamora, R. et al., "Inducible Nitric Oxide Synthase and Inflammatory Diseases," Molecular Medicine, 6(5):347-360 (2000).
Zeidan, A. et al., "Pegasparaginase: where do we stand?", Expert Opinion Biol. Ther, 9(1):111-119 (2009).
UniProtKB Submission F9UJU2_9MOLU, Arginine deiminase; Mycoplasma columbinum SF7 (Jan. 9, 2013). Retrieved from the Internet Jun. 22, 2014: <http://www.uniprot.org/uniprot/F9UJU2.txt?version=6>, 1 page.

(56) References Cited

OTHER PUBLICATIONS

UniProtKB/TrEMBL Submission A7LHN6_9MOLU (Jan. 9, 2013) Retrieved from the Internet Jun. 22, 2014: <http://www.uniprot.org/uniprot/A7LHN6.txt?version=28>, 1 page.

Venugopal, V. et al., "Histidine-dependent activation of arginine deiminase in clostridium sporogenes: Kinetic evidence on in vivo allosteric interactions," FEBS Letters, 51(1):246-248 (1975).

Zlotogorski, A. "Distribution of skin surface pH on the forehead and cheek of adults." Archives of Dermatological Research (1987); 279.6: 398-401.

[Author Unknown] GenBank: EGV00288.1, "arginine deiminase [Mycoplasma columbinum SF7]" Aug. 8, 2011, 2 pages, downloaded May 2, 2019 at https://www.ncbi.nlm.nih.gov/protein/343128488.

Extended European Search Report for European Application No. 15842576.9, dated Jun. 18, 2018, 8 pages.

Invitation to Pay Additional Fees for International Application No. PCT/US2014/026766, dated Jul. 21, 2014, 3 pages.

ENGINEERED CHIMERIC PEGYLATED ADI AND METHODS OF USE

CROSS-REFERENCE TO RELATED APPLICATIONS

This application is a § 371 U.S. national phase application of PCT/US2015/21189, which claims priority under 35 U.S.C. § 119(e) to U.S. Application No. 61/954,929, filed on Mar. 18, 2014, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is TDWG_002_02WO_ST25.txt. The text file is about 200 KB, was created on Mar. 11, 2015, and is being submitted electronically via EFS-Web.

BACKGROUND

Technical Field

The present invention relates generally to engineered ADI, in particular recombinant chimeric ADI proteins engineered to reduce antigenicity. Such engineered chimeric ADI proteins are useful for treating arginine-dependent diseases such as cancer.

Description of the Related Art

Amino acid deprivation therapy can be an effective treatment of some forms of cancer. To date, there is one known clinical example relevant to this approach which utilizes asparaginase to lower circulating levels of asparagine and inhibit protein synthesis. This treatment is particularly effective for acute lymphoblastic leukemia (Avramis 2005, Viera Pinheiro 2004). Acute lymphoblastic leukemia cells require the amino acid asparagine for growth and proliferation. In contrast, most normal human cells are capable of synthesizing asparagine and are unaffected by asparagine depletion. Therefore, decreasing serum asparagine with asparaginase can selectively kill the cancer cells without harming the normal cells, tissues, and host. An *E. coli* derived form of asparaginase has been approved for human use. However, asparaginase is found only in microbes; which makes it highly immunogenic in humans and also has a short serum half-life following injection (Avramis 2005). To make asparaginase a more effective drug, these drawbacks were minimized by formulating the *E. coli* derived asparaginase with polyethylene glycol (PEG) to reduce the immunogenicity of this enzyme and the associated allergic reactions. In addition, PEG greatly prolongs the circulating half-life of asparaginase, which reduces both the frequency of treatment and the total cost of the therapy. PEG formulated asparaginase is approved for use and is marketed under the trade name Oncaspar® (Oncaspar® 2011, Avramis 2005, Viera Pinheiro 2004, Fu 2007, Zeidan 2008).

Arginine is another non-essential amino acid for humans and mice (for review see Rogers 1994). In humans, arginine can be synthesized from citrulline in two steps via the Krebs (urea) cycle enzymes argininosuccinate synthetase (ASS, L-citrulline:L-aspartate ligase [AMP-forming], EC 6.3.4.5) and argininosuccinate lyase (ASL, L-argininosuccinate arginine-lyase, EC 4.3.2.) (Haines 2011, Wu 2009, Morris 2006, Husson 2003, Tapiero 2002, Rogers 1994). ASS catalyzes the conversion of citrulline and aspartic acid to argininosuccinate, which is then converted to arginine and fumaric acid by ASL.

ADI-PEG 20 treatment requires multiple doses over a period of time. After a number of treatments, anti-ADI-PEG 20 antibodies can develop that may limit its continued effectiveness. Therefore, there is a need in the art for ADI that is engineered to improve and extend the efficacy of arginine depletion therapy.

References: Oncaspar FDA Label, Revised 7, 2006; downloaded from FDA website on Apr. 5, 2011; Avramis V I, Panosyan E H. 2005. Clin Pharmacokinet 44:367-393; Fu C H, Sakamoto K M. 2007. Expert Opin Pharmacother 8:1977-1984; Haines R J, et al. 2011. Int J Biochem Mol Biol 2:8-23; Husson A, et al. 2003. Eur J Biochem 270: 1887-1899; Morris S M Jr. 2006. Am J Clin Nutr 83(Suppl): 598S-512S; Viera Pinheiro J P, Boos J. 2004. Br J Haematol 125: 117-127; Wu G, et al. 2009. Amino Acids 37:153-168; Zeidan A, et al. 2008. Expert Opin Biol Ther 9:111-119; Rogers Q R. Special Publication 86, Agriculture Experiment Station, University of Illinois, Apr. 4-5, 1994:9-21; Tapiero H, Mathe G, Couvreur P, Tew K D (2002) I. Arginine. Biomed Pharmacother 56: 439-445; Wheatley D N (2004) Anticancer Drugs 15(9): 825-833; Feun L G, et al, British Journal of Cancer, 2012, 106, 1481-1485; Dillon B J, et al, Cancer, 2004, 100(4), 826-33.

BRIEF SUMMARY

One aspect of the present invention provides a recombinant chimeric arginine deiminase (ADI) comprising a catalytic domain of an ADI protein derived from a first microorganism and an α-helical domain of an ADI protein derived from a second microorganism. In one embodiment, the first microorganism is selected from the genera *Mycoplasma, Clostridium, Bacillus, Borrelia, Enterococcus, Streptococcus, Lactobacillus,* and *Giardia*. In a further embodiment, the first microorganism is selected from the group consisting of *Mycoplasma* pneumonia, *Mycoplasma hominis, Mycoplasma arginini, Mycoplasma arthritidis, Streptococcus pyogenes, Streptococcus pneumonia, Borrelia burgdorferi, Borrelia afzelii, Giardia intestinalis, Clostridium perfringens, Bacillus licheniformis,* and *Enterococcus faecalis*. In yet another embodiment, the first microorganism is selected from the group consisting of *M. arginini, M. arthritidis, M. hominis, Mycoplasma pneumonia, Mycoplasma phocicerebrale, Mycoplasma orale, Mycoplasma gateae, Mycoplasma phocidae, Mycoplasma columbinum, Mycoplasma iowae, Mycoplasma crocodyli, Mycoplasma fermentans, Mycoplasma gallinarum, Mycoplasma iners, Mycoplasma penetrans, Mycoplasma gallisepticum, Mycoplasma alligatoris, Mycoplasma mobile,* and *Mycoplasma capricolum*. In one embodiment, the second microorganism optionally differs from the first microorganism and is selected from the genera *Mycoplasma, Clostridium, Bacillus, Borrelia, Enterococcus, Streptococcus, Lactobacillus,* and *Giardia*. In another embodiment, the second microorganism optionally differs from the first microorganism and is selected from the group consisting of *Mycoplasma pneumonia, Mycoplasma hominis, Mycoplasma arginini, Mycoplasma arthritidis, Streptococcus pyogenes, Streptococcus pneumonia, Borrelia burgdorferi, Borrelia afzelii, Giardia intestinalis, Clostridium perfringens, Bacillus licheniformis,* and *Enterococcus faecalis*. In yet another embodiment, the second microorganism optionally differs from the first microorganism and is selected from the group consisting of *M. arginini, M. arthritidis, M. hominis, Mycoplasma pneumonia, Mycoplasma phocicerebrale, Mycoplasma orale, Mycoplasma gateae, Mycoplasma phocidae, Mycoplasma columbinum, Mycoplasma iowae, Mycoplasma crocodyli, Mycoplasma fermentans, Mycoplasma gallinarum, Mycoplasma iners, Mycoplasma penetrans, Mycoplasma gallisepticum, Mycoplasma alligatoris, Mycoplasma mobile,* and *Mycoplasma capricolum.*

In one embodiment, the first microorganism is selected from the group consisting of *Mycoplasma gallinarum, Mycoplasma iners,* and *Mycoplasma* columbinum and the second microorganism is selected from the group consisting of *Mycoplasma gallinarum, Mycoplasma iners,* and *Mycoplasma* columbinum, wherein the first and second microorganism are optionally different microorganisms.

In a further embodiment, the first microorganism is *M. arginini* and the second microorganism is *M. arthritidis,* and in other specific embodiments, the first microorganism is *M. arginini* and the second microorganism is *M. hominis* or the first microorganism is *M. arthritidis* and the second microorganism is *M. arginini*. In certain embodiments, the first microorganism is *M. gateae* and the second microorganism is *M. arthritidis*. In certain embodiments, the first microorganism is *M. gateae* and the second microorganism is *M. columbinum*. In some embodiments, the first microorganism is *M. gateae* and the second microorganism is *M. phocicerebrale*. In some embodiments, the first microorganism is *M. gateae* and the second microorganism is *M. phocidae*. In particular embodiments, the first microorganism is *M. phocicerebrale* and the second microorganism is *M. arginini*. In certain embodiments, the first microorganism is *M. phocicerebrale* and the second microorganism is *M. gateae*. In specific embodiments, the first microorganism is *M. phocicerebrale* and the second microorganism is *M. phocicerebrale*. In certain embodiments, the first microorganism is *M. phocidae* and the second microorganism is *M. arginini*. In some embodiments, the first microorganism is *M. phocidae* and the second microorganism is *M. arthritidis*. In certain embodiments, the first microorganism is *M. phocidae* and the second microorganism is *M. columbinum*. In particular embodiments, the first microorganism is *M. phocidae* and the second microorganism is *M. gateae*. In certain embodiments, the first microorganism is *M. phocidae* and the second microorganism is *M. phocicerebrale*. In some embodiments, the first microorganism is *M. gallinarum* and the second microorganism is *M. columbinum*. In certain embodiments, the first microorganism is *M. gallinarum* and the second microorganism is *M. iners*. In some embodiments, the first microorganism is *M. iners* and the second microorganism is *M. columbinum*. In certain embodiments, the first microorganism is *M. iners* and the second microorganism is *M. gallinarum*.

Illustrative recombinant chimeric ADI molecules comprise, consist, or consist essentially of the amino acid sequence set forth in any one of SEQ ID NOs:4-13 or 22-59 or a variant thereof having at least 80% or 90% sequence identity to any of SEQ ID NOs:4-13 or 22-59.

In certain embodiments of the recombinant chimeric ADI described herein, the recombinant chimeric ADI has been modified to remove at least one pegylation site. In another embodiment of the recombinant chimeric ADI described herein, at least one lysine residue has been modified by an amino acid substitution. In certain embodiments of the recombinant chimeric ADI described herein, at least 5 lysine residues have been modified by an amino acid substitution, at least 10 lysine residues have been modified by an amino acid substitution, at least 15 lysine residues have been modified by an amino acid substitution, or at least 20 lysine residues have been modified by an amino acid substitution. Illustrative recombinant chimeric ADI molecules as described herein comprise the amino acid sequence set forth in any one of SEQ ID NOs:10-13.

In another embodiment of the recombinant chimeric ADI described herein, the ADI is covalently bonded via a biocompatible linker to polyethylene glycol. In this regard, the arginine deiminase may be covalently bonded to more than one polyethylene glycol molecule and in certain embodiments may be covalently bonded to about 1 to about 10 polyethylene glycol molecules and in one specific embodiment, to 5±3 PEG molecules. The PEG molecules covalently bonded to the ADI as described herein may be straight chain or branch chain PEG molecules and may have a total weight average molecular weight of from about 1,000 to about 40,000 and in one embodiment, from about 10,000 to about 30,000.

In certain embodiments of the recombinant chimeric ADI described herein, the biocompatible linker comprises a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof. In one embodiment, the source of the succinyl group is succinimidyl succinate.

Other aspects of the invention provide a polynucleotide encoding the recombinant chimeric ADI described herein, vectors comprising the polynucleotide and isolated host cells comprising such vectors.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008).

Systems for cloning and expression of a protein in a variety of different host cells are well known. Suitable host cells include mammalian cells, bacteria, yeast, and baculovirus systems. Mammalian cell lines available in the art for expression of a heterologous polypeptide include Chinese hamster ovary (CHO) cells, HeLa cells, baby hamster kidney cells, HEK-293 cells, human fibrosarcoma cell line HT-1080 (see, e.g., Moran, Nat. Biotechnol. 28:1139-40, 2010), NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al, *J. Gen Virol.* 36:59 (1977)); baby hamster kidney cells (BHK, ATCC CCL 10); mouse sertoli cells (TM4, *Mather, Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for polypeptide production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200L WAVE bioreactors, among others known in the art.

A common bacterial host is *E. coli.* The expression of proteins in prokaryotic cells such as *E. coli* is well established in the art. For a review, see for example Pluckthun, *A. Bio/Technology.* 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21 (DE3), a λDE3 lysogen of BL21 that supports T7-mediated expression and is deficient in Ion and ompT proteases for improved target protein stability. Also included are expression host strains carrying plasmids encoding tRNAs rarely used in *E. coli,* such as Rosetta® (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His-Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the protein of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., chimeric ADI proteins.

Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the chimeric ADI proteins have a purity of at least about 90%, as measured according to routine techniques in the art. In certain embodiments, such as diagnostic compositions or certain therapeutic compositions, the chimeric ADI proteins have a purity of at least about 95%. In specific embodiments, such as therapeutic or pharmaceutical compositions, the chimeric ADI proteins have a purity of at least about 97% or 98% or 99%. In other embodiments, such as when being used as reference or research reagents, proteins can be of lesser purity, and may have a purity of at least about 50%, 60%, 70%, or 80%. Purity can be measured overall or in relation to selected components, such as other proteins, e.g., purity on a protein basis.

In certain embodiments, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the chimeric ADI proteins are made from a eukaryotic cell such as a mammalian or human cell in substantially serum free media.

Another aspect of the invention provides a composition comprising one or more of the recombinant chimeric ADI described herein and a physiologically acceptable carrier. In one embodiment, the composition may further comprise an autophagy modulator. Autophagy modulators include, but are not limited to chloroquine, 3-methyladenine, hydroxychloroquine, bafilomycin A1, 5-amino-4-imidazole carboxamide riboside (AICAR), okadaic acid, N6-mercaptopurine riboside, vinblastine, wortmannin, rapamycin, everolimus, metformin, perifosine, resveratrol, and tamoxifen. In another embodiment, the compositions comprising the recombinant chimeric ADI described herein may further comprise a chemotherapeutic agent, such as but not limited to docetaxel, carboplatin, cyclophosphamide, gemcitabine, cisplatin, sorafenib, sunitinib or everolimus, or combinations thereof.

Yet another aspect of the present invention provides a method of treating, ameliorating the symptoms of, or inhibiting the progression of a cancer comprising administering to a patient in need thereof a therapeutically effective amount of a composition comprising one or more of the recombinant chimeric ADI described herein and a physiologically acceptable carrier, thereby treating, ameliorating the symptoms of, or inhibiting the progression of the cancer. In this regard, the cancer can include, but is not limited to melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

BRIEF DESCRIPTION OF THE SEQUENCES

SEQ ID NO:1 is the amino acid sequence of wild type *M. hominis* ADI.

SEQ ID NO:2 is the amino acid sequence of wild type *M. arginini* ADI.

SEQ ID NO:3 is the amino acid sequence of wild type *M. arthritidis* ADI.

SEQ ID NO:4 is the amino acid sequence of the DS1 recombinant chimeric ADI protein.

SEQ ID NO:5 is the amino acid sequence of the DS2 recombinant chimeric ADI protein.

SEQ ID NO:6 is the amino acid sequence of the DS3 recombinant chimeric ADI protein.

SEQ ID NO:7 is the amino acid sequence of the DS4 recombinant chimeric ADI protein.

SEQ ID NO:8 is the amino acid sequence of a recombinant chimeric ADI derived from *M. hominis* Phoenix (see SEQ ID NO:14; plus lysine substitutions) (catalytic domain) and *M. arginini* (α-helical domain).

SEQ ID NO:9 is the amino acid sequence of a recombinant chimeric ADI derived from *M. hominis* Phoenix (see SEQ ID NO:14) (catalytic domain) and *M. arthritidis* (α-helical domain).

SEQ ID NO:10 is the amino acid sequence of the DS1-1 lysine reduction mutant of the recombinant chimeric ADI protein (see Table E3).

SEQ ID NO:11 is the amino acid sequence of the DS1-2 lysine reduction mutant of the recombinant chimeric ADI protein (see Table E3).

SEQ ID NO:12 is the amino acid sequence of the DS1-3 lysine reduction mutant of the recombinant chimeric ADI protein (see Table E3).

SEQ ID NO:13 is the amino acid sequence of the DS1-4 lysine reduction mutant of the recombinant chimeric ADI protein (see Table E3).

SEQ ID NO:14 is the amino acid sequence of the ADI Phoenix sequence. This ADI sequence is identical to *M. hominis* ADI except for K112E and P210S substitutions.

SEQ ID NO:15 is the amino acid sequence of *M. alligatoris* ADI.

SEQ ID NO:16 is the amino acid sequence of *M. colombinum* ADI.

SEQ ID NO:17 is the amino acid sequence of *M. gallinarum* ADI.

SEQ ID NO:18 is the amino acid sequence of *M. gatea* ADI.

SEQ ID NO:19 is the amino acid sequence of *M. iners* ADI.

SEQ ID NO:20 is the amino acid sequence of *M. phocicerabrale* ADI.

SEQ ID NO:21 is the amino acid sequence of *M. phocidae* ADI.

SEQ ID NOs:22-59 are the amino acid sequences of chimeric ADI proteins.

DETAILED DESCRIPTION

The present invention relates generally to chimeric ADI proteins, e.g., engineered to have reduced antigenicity as compared with corresponding wild type ADI molecules. The present invention also relates to methods of treating cancer and other disorders with chimeric ADI, and in particular chimeric ADI-PEG 20.

Normal cells do not require arginine for growth, since they can synthesize arginine from citrulline in a two-step process catalyzed by ASS and ASL. In contrast, certain cancers do not express ASS. Certain cancers do not express ASL, and other cancers may have diminished expression of, or may not express ASS and/or ASL. Therefore, these cancers are auxotrophic for arginine. This metabolic difference may be capitalized upon to develop a safe and effective therapy to treat these forms of cancer. ADI catalyzes the conversion of arginine to citrulline via the arginine dihydrolase pathway, and may thus be used to eliminate arginine.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Protein Science, Current Protocols in Molecular Biology or Current Protocols in Immunology, John Wiley & Sons, New York, N.Y. (2009); Ausubel et al., Short Protocols in Molecular Biology, 3rd ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

"Patient" refers to an animal, in certain embodiments a mammal, and in a specific embodiment, a human.

"Biocompatible" refers to materials or compounds which are generally not injurious to biological functions and which will not result in any degree of unacceptable toxicity, including allergenic and disease states.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence listing.

Throughout the present disclosure, the following abbreviations may be used: PEG, polyethylene glycol; ADI, arginine deiminase; SS, succinimidyl succinate; SSA, succinimidyl succinimide; SPA, succinimidyl propionate; NHS, N-hydroxy-succinimide; ASS1 or ASS, argininosuccinate synthetase; ASL, argininosuccinate lyase.

In certain embodiments, the chimeric ADI enzymes as described herein are compared to the benchmark ADI-PEG 20 molecule derived from *M. hominis*. As used herein, "ADI-PEG 20" refers to the ADI molecule known in the art and described for example in U.S. Pat. Nos. 6,183,738; 6,635,462; Ascierto Pa., et al. (2005) Pegylated arginine deiminase treatment of patients with metastatic melanoma: results from phase I and II studies. J Clin Oncol 23(30): 7660-7668; Izzo F, et al. (2004) Pegylated arginine deiminase treatment of patients with unresectable hepatocellular carcinoma: results from phase I/I studies. J Clin Oncol 22(10): 1815-1822; Holtsberg F W, et al. (2002), Poly (ethylene glycol) (PEG) conjugated arginine deiminase: effects of PEG formulations on its pharmacological properties. J Control Release 80(1-3): 259-271; Kelly et al., (2012) British Journal of Cancer 106, 324-332. As would be recognized by the skilled artisan, this molecule is a pegylated (PEG 20,000) ADI enzyme derived from *M. hominis*, and has two substitutions (K112E; P210S) relative to the wild type *M. hominis* ADI enzyme.

The terms "polypeptide," "protein" and "peptide" and "enzyme" are used interchangeably and mean a polymer of amino acids not limited to any particular length. The terms do not exclude modifications such as myristoylation, sulfation, glycosylation, phosphorylation and addition or deletion of signal sequences. The terms "polypeptide" or "protein" or "enzyme" mean one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the chimeric ADI enzymes of the present disclosure, or sequences that have deletions from, additions to, and/or substitutions of one or more amino acid of the chimeric ADI enzymes. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In the present invention, a chimeric ADI or a polynucleotide encoding a chimeric ADI may be derived, cloned or produced from any source, including, for example, microorganisms, recombinant biotechnology or any combination thereof. For example, arginine deiminase may be cloned from microorganisms of the genera *Mycoplasma, Clostridium, Bacillus, Borrelia, Enterococcus, Streptococcus, Lactobacillus, Giardia*. In certain embodiments, arginine deiminase is cloned from *Mycoplasma pneumoniae, Mycoplasma hominis, Mycoplasma arginini, Mycoplasma arthritidis, Mycoplasma phocicerebrale, Mycoplasma orale, Mycoplasma gateae, Mycoplasma phocidae, Mycoplasma columbinum, Mycoplasma iowae, Mycoplasma crocodyli, Mycoplasma fermentans, Mycoplasma penetrans, Mycoplasma gallisepticum, Mycoplasma gallinarum, Mycoplasma iners, Mycoplasma alligatoris, Mycoplasma mobile*, and *Mycoplasma capricolum, Steptococcus pyogenes, Steptococcus pneumoniae, Borrelia burgdorferi, Borrelia afzelii, Giardia intestinalis, Clostridium perfringens, Bacillus licheniformis, Enterococcus faecalis, Lactobacillus* sake, or any combination thereof. The amino acid sequences of certain of these arginine deiminases is provided in Table A1 below.

TABLE A1

Exemplary ADI sequences for cloning of chimeric ADI

| Source | Sequence | SEQ ID NO: |
|---|---|---|
| M. hominis | MSVFDSKENGIHVYSETGELETVLVHEPGREIDYITPARLDELLFSAI LESHDARKEHQSFVKIMKDRGINVVELTDLVAETYDLASKAAKEEFIE TFLEETVPVLTEANKEAVRAFLLSKPTHEMVEFMMSGITKYELGVESE NELIVDPMPNLYFTRDPFASVGNGVTIHFMRYIVRRRETLFARFVERN HPKLVKTPWYYDPAMKMSIEGGDVFIYNNETLVVGVSERTDLDTITLL AKNIKANKEVEFKRIVAINVPKWTNLMELDTWLTMIDKNKFLYSPIAN DVFKFWDYDLVNGGAEPQPQLNGLPLDKLLASIINNEPVLIPIGGAGA TEMEIARETNPDGTNYLAIKPGLVIGYDRNEKTNAALKAAGITVIPFH GNQLSLGMGNARCMSMPLSRKDVKW | 1 |
| M. arginini | MSVEDSKFKGIHVYSEIGELESVLVHEPGREIDYITPARLDELLESAI LESHDARKEHKQFVAELKANDINVVELIDLVAETYDLASQEAKDKLIE EFLEDSEPVLSEEHKVVVRNFLKAKKTSRELVEIMMAGITKYDLGIEA DHELTVDPMPNLYFTPDPEASVGNGVTIHYMRYKVRQRETLESRFVRS NHPKLINTPWYYDPSLKLSTEGGDVELYNNDTLVVGVSERTDLQTVTL LAKNIVANKESEFKRIVAINVPKWTNLMHLDTWLTMLDKDKFLYSPIA NDVFKFWDYDLVNGGAEPQPVENGLPLEGLLQSIINKKPVIIPIAGEG ASQMEIERETHEDGTNYLAIRPGVVIGYSRNEKTNAALEAAGIKVLPF HGNQLSLGMGNARCMSMPLSRKDVKW | 2 |
| N. arthritidis | msvfdskfkgihvvseigeietvlvhepgkeidyitparldelifsai leshdarkehkefvaelkkrginvvelvdlivetydiaskeakekile eflddsvpvlsdehratvkkflqsqkstrslveymiagitkhdlkies dlelivdpmpnlyftrdpfasvgngvtihymrykvrqretifsrfvfs nhpklvntpwyydpaegltieggdvfiynndtlvvgvsertdlgtitl iaknikankesefkrivainvpkwtnlmhldtwitmldkdkflyspia ndvfkfwdvdlvngadapqpvdngipledilksiigkkptlipiagag asqidierethfdqtnylavapgivigyarnekthaaleaagitvipf rgnqlslgmgnarcmsmplsrkdvkw | 3 |
| M. alligatoris | MSKINVYSEVGRLKEVLVHTPGDEIRRISPTRLEELLFSAILEPDTAI EEHKRRLNVLEKNGIFAIQLDELVAQTYDQVDQKIKDERIDQWLQEAK PVLNDQLKKLVKNYLLKSQKEFSTKKMVRIMMAGIDKKEINIDLDRDL VVDPMPNLYFTRDPFASVGNGISLHNMKYQTRKRETIFAQFIYKYNKD YKTTPHWFDRFDHGSIEGGDVFVYTKDTLVIGISERTTKEAVLNIAKK IKANTDSKFKKIVAINVPPMPNLMHLDTWITMVDHDKFLYSPNMMKSL KFWLIDLSKEIKMVELEESLSNMLEAIIGKKPILIPIAGKNASQLDID IETHFDGTNYLTIAPGVVVGITSRNKLTUALEDAGVKVLSFDGNQLSL GMGSARCMSMPLVREDIK | 15 |
| M. colombinum | MSKINVYSEIGELKEVINHTPGDEIRRISPSRLDELLFSAILEPNEAI KEHKGFLKILQDKGIKVIQLSDLVAETYTYHATQKEREAFIEKWLDEA EPALTKDLRAKVKSYVLSKEGTPVAMVRTMMAGVSKQELNVESETELV VDPMPNLYFTRDPFASAGNGISLNNMKYVTRFRETIPAEFIPATHPDY KTTPHWFDRLDEGNIEGGDVFIYNKDTLVIGVSERTNKEAILTIAKKI | 16 |

TABLE A1-continued

Exemplary ADI sequences for cloning of chimeric ADI

| Source | Sequence | SEQ ID NO: |
|---|---|---|
| | KNNKEAKFKKIVAINVPPMPNLMHLDTWLTMVDKDKFLYSPNMLSVLK<br>VWEIDLSKEIEMVETNKPLADVLESIIGVKPVLIPIAGKGATQLDIDI<br>ETHFDGTNYLTIAPGVVVGYSRNIKTEAALRAAGVTVLSFEGNQLSLG<br>MGSARCMSMPLVREDVK | |
| M. gallinarum | MSKIRVYSEIGNLKKVIVHTPGDEIRRISPSRLEELLFSAVLEPNAAI<br>EEHKRFVKLLEDRGIQAIQLSDLVAETYVKYATAEQKAAFIEKYLDEA<br>TPALSAENRERAKKYILSLEMQPVKMIRTMMAGLSKYELNVESNIELI<br>IDPMPNLYNTRDPFASAGNGISLNNMKYVVRKRETIFAEFIFAIHPEY<br>KETPEWFDRLDNGSIEGGDVFVYNKDTLVIGVSERTNEEAIITIAKHI<br>QDNKEAEFKKEVAINVPPMPNLMHLDTWITMVDKNKFIYSPNMLSVLK<br>IWEIDLAKPIEMVESNKSLTEVLESIIGEKPILIPIAGEGASQLDIDI<br>ETHFDGTNYLTIAPGVVVGYSRNEKTEKALKAAGITVLSFEGNQLSLG<br>MGSARCMSMPLVREDVK | 17 |
| M. gatea | MSVPDSKFNGIHVYSEIGELESVLVHEPGREIDYITPARLDELLFSAI<br>LESHDARKEHKLFVSELKANDINVVELTDLVTETYDLASQEAKDNLIE<br>EFLEDSEPVLTEELKSVVRTYLKSIKSTRELLQMMMAGITKYDLGIEA<br>DHELIVDPMPNLYFTRDPFASVGNGVTIHYMRYEVRQRETLFSRFVFS<br>NHPKLVNTPWYYDPSLKLSIEGGDVFIYNNNTLVVGVSERTDLETVTL<br>LANNIVANKECEFKRIVAINVPKWTNLMHLDTWLTMIDKDKFLYSPIA<br>NDVFKFWDYDLVNGGEEPQPVENGLPLEGLLESIINKYPILIPIAGEG<br>ASQIDIERETNFDGTNYLAIRPGVVIGYSRNEKTNAALEAAGIKVLPF<br>HGNQLSLGMGNARCMSMPLSRKDVKW | 18 |
| M. iners | MSKINVYSEIGVLKEVINHTPGDEIRRIAPSRLDELLFSAILEPSAAI<br>QEHKSFLKILQDRGIKTIQLSDLVAETYKEYASEAEKEAFIEKYLDEA<br>TPVLSKDMRAKVEEYILSMQGEPVKMVRTMMAGVSKQELNVESEVELI<br>VDPMPNLYFTRDPFASAGNGISLNNMKYVVRKRETIFAEFIFSIHPEY<br>KKTPHWFDRLDNGSTEGGDVFIYNKDTLVIGVSERTNKEATITIAKHI<br>QDNKEAQFKKIVAINVPPMPNLMELDTWLTMVDKNKFLYSPNMLSVLK<br>VWEIDLSKPIEMVETNKPLAEVLESIIGEKPILIPIAGKDATQLDIDI<br>ETHFDGTNILTIAPGVVVGYSRNVKTEAALRAAGVTVLSFEGNQLSLG<br>MGSARCMSMPLVREDVK | 19 |
| M. phocicerabrale | MSVFDSKFNGIHVYSEIGELETVLVHEPGREIDYITPARLDELLFSAI<br>LESHDARKEHQSFVKQLKDNGINVVELTDLVAETYDLASKEEQEKLIE<br>EFLEDSEPVLSEAHKTAVRKFLTSRKSTREMMEEMMAGITKYDLGIEA<br>DHELIVDPMPNLYFTRDPFASVGNGVTIHYMRYKVRQRETLFSRFVFS<br>NHPKLVKTPWYYDPAMKMSIEGGDVFIYNNDTLVVGVSERTDLETITL<br>LAKNIKANKEVEFKRIVAINVPKWTNLMELDTWLTMIDKDKFLYSPIA<br>NDVFKFWDYDLVNGGAEPQPKENGLPLEGLLQSIINKKPVLIPIAGNN<br>ASHIDIERETHFDGTNYLAIKPGVVIGYARNEKTNAALAAAGIKVLPF<br>HGNQLSLGMGNARCMSMPLSRKDVKW | 20 |
| M. phocidae | MSVPDSKFNGIHVYSEIGELQTVLVHEPGREIEYITPARLDELLFSAI<br>LESHDARKEHQEFVAELKKNNINVVELTDLVSETYDMVSNEKQEKLIE<br>EFLEDSEPVLSEEHKGLVRKFLKSLKSSKELIQYMMAGITKHDLNIEA<br>DHELIVDPMPNLYNTRDPFASVGNGVTIHYMRYKVRQRETLFSRFIFA<br>NHPKLMNTPLYYNPDMEISIEGGDVFVYNNETLVVGVSERTDLDTITL<br>LAKNIKANKEREFKRIVAINVPKWTNLMHLDTWLTMLDKDKFLYSPIA<br>NDVFKFWDYDLVNGGDEPQPKVNGLPLEKLLESIINKKPILIPIAGTS<br>ASNIDVERETNFDGTNYLAIAPGVVIGYSRNVKTNEALEAAGIKVLPF<br>KGNQLSLGMGNARCMSMPLSRKDVKW | 21 |

Thus, in some embodiments, the ADI used in a chimeric ADI may comprise the amino acid sequence from Table A1 (any one of SEQ ID NOs: 1-3 or 15-21), or a variant thereof having ADI activity (e.g., able to metabolize arginine into citrulline and ammonia) or a fragment thereof having ADI activity, or engineered chimeras thereof having ADI activity.

The sequences of exemplary chimeric ADI are provided in Table A2 below.

TABLE A2

Chimeric ADI

| Name | Sequence | SEQ ID NO: |
|---|---|---|
| DS1 | MSVFDSKFKGIHVYSEIGELESVLVHEPGREIDYITPARLDELLFSAILESH<br>DARKEHKQFVAELKANDINVVELVDLIVETYDLASKEAKEKLLEEFLDDSVP<br>VLSDEHRATVKKFLQSQKSTRSLVEYMIAGITKHDLKIESDLELIVDPMPNL<br>YFTRDPFASVGNGVTIHYMRYKVRQRETLFSRFVFSNHPKLINTPWYYDPSL<br>KLSIEGGDVFIYNNDTLVVGVSERTDLQTVTLLAKNIVANKESEFKRIVAIN | 4 |

TABLE A2-continued

Chimeric ADI

| Name | Sequence | SEQ ID NO: |
|---|---|---|
| | VPKWTNLMHLDTWLTMLDKDKFLYSPIANDVFKFWDYDLVNGGAEPQPVENG<br>LPLEGLLQSIINKKPVLIPIAGEGASQMEIERETHFDGTNYLAIRPGVVIGY<br>SRNEKTNAALEAAGIKVLPFHGNQLSLGMGNARCMSMPLSRKDVKW | |
| DS2 | MSVFDSKFKGIHVYSEIGELESVLVHEPGREIDYITPARLDELLFSAILESH<br>DARKEHKQFVAELKANDINVVELTDLVAETYDLASRAAKEEFIETFLEETVP<br>VLTEANREAVRAFLLSKPTHEMVEFMMSGITKYELGVESENELIVDPMPNLY<br>FTRDPFASVGNGVTIHYMRYKVRQRETLFSRFVFSNHPKLINTPWYYDPSLK<br>LSIEGGDVFIYNNDTLVVGVSERTDLQTVTLLAKNIVANKESEFKRIVAINV<br>PKWTNLMHLDTWLTMLDKDKFLYSPIANDVFKFWDYDLVNGGAEPQPVENGL<br>PLEGLLQSIINKKPVLIPIAGEGASQMEIERETHFDGTNYLAIRPGVVIGYS<br>RNEKTNAALEAAGIKVLPFHGNQLSLGMGNARCMSMPLSRKDVKW | 5 |
| DS3 | MSVFDSKFKGIHVYSEIGELETVLVHEPGKEIDYITPARLDELLFSAILESH<br>DARKEHKEFVAELKKRGINVVELIDLVAETYDLASQEAKDKLIEEFLSDSEP<br>VLSEEHKVVVRNFLKAKKTSRELVEIMMAGITKYDLGIEADHELIVDPMPNL<br>YFTRDPFASVGNGVTIHYMRYKVRQRETLFSRFVFSNHPKLVNTPWYYDPAE<br>GLTIEGGDVFIYNNDTLVVGVSERTDLQTITLLAKNIKANKESEFKRIVAIM<br>VPKWTNLMHLDTWLTMLDKDKFLYSPIANDVFKFWDYDLVNGGDAPQPVDWG<br>LPLEDLLKSIIGKKPTLIPIAGAGASQIDIERETHFDGTKYLAVAPGIVIGY<br>ARNEKTNAALEAAGITVLPFRGNQLSLGMGNARCMSMPLSRKDVKW | 6 |
| DS4 | MSVFDSKFKGIHVYSEIGELETVLVHEPGKEIDYITPARLDELLFSAILESH<br>DARKEHKEFVAELKKRGINVVELTDLVAETYDLASRAAKEEFIETFLEETVP<br>VLTEANREAVRAFLLSKPTHEMVEFMMSGITKYELGVESENELIVDPMPNLY<br>FTRDPFASVGNGVTIHYMRYKVRQRETLFSRFVFSNKPKLVNTPWYYDPAEG<br>LTIEGGDVFIYNNDTLVVGVSERTDLQTITLLAKNIKANKESEFKRIVAINV<br>PKWTNLMHLDTWLTMLDKDKFLYSPIANDVFKFWDYDLVNGGDAPQPVDNGL<br>PLEDLLKSIIGKKPTLIPIAGAGASQIDIERETHFDGTNYLAVAPGIVIGYA<br>RNEKTNAALEAAGITVLPFRGNQLSLGMGNARCMSMPLSRKDVKW | 7 |
| C2DS1 | MSVFDSKFKGIHVYSEIGELE8VLVHEPGREIDYITPARLDELLF8AILESHDAR<br>KEHKQFVAELKAMDINVVELDELVAQTYDQVDQKIKDEFIDQWLQEAKPVLNDQL<br>KKLVKNYLLKSQKEFSTKKMVRIMMAGIDKKEINIDLDRDLVVDPMPNLYFTRDP<br>FASVGNGVTIHYMRYKVRQRETLFSRFVFSNHPKLINTPWYYDPSLKLSIEGGDV<br>FIYNNDTLVVGVSERTDLQTVTLIAKNIVANKESEFKRIVAINVPKWTNLMHLDT<br>WLTMLDKDKFLYSPIANDVFKFWDYDLVNGGAEPQPVENGLPLEGLLQSIINKKP<br>VLIPIAGEGASQMEIERETKFDGTNYLAIRPGVVIGYSRNEKTNAALEAAGIKVL<br>PFHGNQLSLGMGNARCMSMPLSRKDVKW | 22 |
| C2DS3 | MSVFDSKFKGIKVYSSIGELESVLVHEPGREIDYITPARLDELLFSAILESKDAR<br>KEKKQFVAELKANDINVVELVDLIVETYDLASKEAKEKLLEEFLDDSVPVLSDEH<br>RATVKKFLQSQKSTRSLVEYMIAGITKKDLKIESDLELIVBPMPNLYFTRDPFAS<br>VGNGVTIHYMRYKVRQRETLFSRFVFSNHPKLINTPWYYDPSLKLSIEGGDVFIY<br>NNDTLVVGVSERTDLQTVTLLAKNIVANKESEFKRIVAINVPKWTNLMHLDTWLT<br>MLDKDKFLYSPIANDVFKFWDYDLVNGGAEPQPVENGLPLEGLLQSIINKKPVLI<br>PIAGEGASQMEIERETHFDGTNYLAIRPGVVIGYSRNEKTNAALEAAGIKVLPFH<br>GNQLSLGMGNARCMSMPLSRKDVKW | 23 |
| C2DS4 | MSVFDSKFKGIHVYSEIGELESVLVHEPGREIDYITPARLDELLFSAILESHDAR<br>KEHKQFVAELKANDINVVELSDLVAETYTYHATQKEREAFIEKWLDEAEPALTKD<br>LPAKVKSYVLSKEGTPVAMVRTMMAGVSKQELNVESETELVVDPMPNLYFTRDPF<br>ASVGNGVTIHYMRYKVRQRETLFSRFVFSNHPKLINTPWYYDPSLKLSIEGGDVF<br>IYNNDTLVVGVSERTDLQTVTLLAKNIVANKESEFKRIVAINVPKWTNLMHLDTW<br>LTMLDKDKFLYSPIANDVFKFWDYDLVNGGAEPQPVENGLPLEGLLQSIINKKPV<br>LIPIAGEGASQMEIERETHFDGTNYLAIRPGVVIGYSRNEKTNAALEAAGIKVLP<br>FHGNQLSLGMGNARCMSMPLSRKDVKW | 24 |
| C2DS5 | MSVFDSKFKGIHVYSEIGELESVLVHEPGREIDYITPARLDELLFSAILESHDAR<br>KEKKQFVAELKANDINVVELTDLVTETYDLASQEAKDNLIEEFLEDSEPVLTEEL<br>KSVVRTYLKSIKSTRELIQMMMAGITKYDLGIEADKELIVDPMPNLYFTRDPFAS<br>VGNGVTIHYMRYKVRQRETLFSRFVFSNHPKLINTPWYYDPSLKLSIEGGDVFIY<br>NNDTLVVGVSERTDLQTVTLLAKNIVANKESEFKRIVAINVPKWTNLMHLDTWLT<br>MLDKDKFLYSPIANDVFKFWDYDLVNGGAEPQPVENGLPLEGLLQSIINKKPVLI<br>PIAGEGASQMEIERETHFDGTNYLAIRPGVVIGYSRNEKTNAALEAAGIKVLPFH<br>GNQLSLGMGNARCMSMPLSRKDVKW | 25 |
| C2DS6 | MSVFDSKFKGIHVYSEIGELESVLVHEPGREIDYITPARLDELLFSAILESHDAR<br>KEHKQFVAELKANDINVVELTDLVAETFDLASKEEQEKLIEEFLEDSEPVLSEAH<br>KTAVRKFLTSRKSTREMVEFMMAGITKYDLGIEADHELIVBPMPMLYFTRDPFAS<br>VGNGVTIHYMRYKVRQRETLFSRFVFSNHPKLINTPWYYDPSLKLSIEGGDVFIY<br>NNDTLVVGVSERTDLQTVTLLAKNIVANKESEFKRIVAINVPKWTNLMHLDTWLT<br>MLDKDKFLYSPIANDVFKFWDYDLVNGGAEPQPVENGLPLEGLLQSIINKKPVLI<br>PIAGEGASQMEIERETHFDGTNYLAIRPGVVIGYSRNEKTNAALEAAGIKVLPFH<br>GNQLSLGMGNARCMSMPLSRKDVKW | 26 |

TABLE A2-continued

Chimeric ADI

| Name | Sequence | SEQ ID NO: |
|---|---|---|
| C2DS7 | MSVFDSKFKGIHVYSEIGELESVLVHEPGREIDYITPARLDELLFSAILESHDAR ECEHKQFVAELKANDINWELTDLVSETYDMVSKEKQEKLIEEFLEDSEFVLSEEH KGLVRKFLKSLKSSKELIQYMMAGITKHDLNIEADKELIVDPMPNLYFTRDPFAS VGNGVTIHYMRYKVRQRETLFSRFVFSNHPKLINTPWYYDPSLKLSIEGGDVFIY NNDTLVVGVSERTDLQTVTLLAKNIVANKESEFKRIVAINVPKWTMLMHLDTWLT MLDKDKFLYSPIANDVFKFWDYDLVNGGAEPQPVENGLPLEGLLQSIINKKPVLI PIAGEGASQMEIERETHFDGTNYLAIRPGVVIGYSRMEKTNAALEAAGIKVLPFH GNQLSLGMGNARCMSMPLSRKDVKW | 27 |
| C4DS1 | MSKINVYSEIGELKEVLVHTPGDEIRRISPSRLDELLFSAILEPNEAIKEHKGFL KILQDKGIKVIQLDELVAQTYDQVBQKIKDEFIDQWLQEAKPVLNDQLKKLVKNY LLKSQKEFSTKKMVRIMMAGIDKKEINIDLDRDLVVDPMPNLYFTRDPFASAGNG ISLNNMKYVTRKRETIFAEFIFATHPDYKTTPHWFDRLDEGNIEGGDVFIYNKDT LVIGVSERTNKEAILTIAKKIKNNKEAKFKKIVAINVPPMPNLMHLDTWLTMVDK DKFLYSPNMLSVLKVWEIDLSKEIEMVETNKPLADVLESIIGVKPVLIPIAGKGA TQLDIDIETHFDGTNYLTIAPGVVVGYSRNIKTEAALRAAGVTVLSFEGNQLSLG MGSARCMSMPLVREDVK | 28 |
| C4DS2 | MSKINVYSEIGELKEVLVHTPGDEIRRISPSRLDELLFSAlLEPNEAIKEKKGFL KILQDKGIKVIQLIDLVAETYDLASQEAKDKLIEEFLEDSEPVLSEEHKVVVRNF LKAKKTSRELVEIMMAGITKYDLGIEADHELIVDPMFNLYFTRDPFASAGNGISL NNMKYVTRKRETIFAEFIFATHPDYKTTPHWFDRLDEGNIEGGDVFIYNKDTLVI GVSERTNKEAILTIAKKIKNNKEAKFKKIVAINVPPMPKLMHLDTWLTMVDKDKF LYSPNMLSVLKVWEIDLSKEIEMVETNKPLADVLESIIGVKPVLIPIAGKGATQL DIDIETHFDGTNYLTIAPGVVVGYSRNIKTEAALRAAGVTVLSFEGNQLSLGMGS ARCMSMPLVREDVK | 29 |
| C4DS3 | MSKINVYSEIGELKEVLVHTPGDEIRRISPSRLDELLFSAILEPNEAIKEHKGFL KILQDKGIKVIQLVDLIVETYDLASKEAKEKLLEEFLDDSVPVLSDEHRATVKKF LQSQKSTRSLVEYMIAGITKHDLKIESDLELIVDPMPNLYFTRDPFASAGNGISL NNMKYVTRKRETIFAEFIPATHPDYKTTPHWFDRLDEGNIEGGDVFIYNKDTLVI GVSERTNKEAILTIAKKIKNNKEAKFKKIVAINVPMPNLMHLDTWLTMVDKBKF LYSPNMLSVLKVWEIDLSKEIEMVETNKPLADVLESIIGVKPVLIPIAGKGATQL DIDIETHFDGTNYLTIAPGVVVGYSRKIKTEAALRAAGVTVLSFEGNQLSLGMGS ARCMSMPLVREDVK | 30 |
| C4DS5 | MSKINVYSEIGELKEVLVHTPGDEIRRISPSRLDELLFSAILEPNEAIKEHKGFL KILQDKGIKVIQLTDLVTETYDLASQEAKDNLIEEFLEDSEPVLTEELKSVVRTY LKSIKSTRELIQMMMAGITKYDLGIEADHELIVDPMFNLYFTRDPFASAGNGISL NNMKYVTRKRETIFAEFIFATHPDYKTTPHWFDRLDEGNIEGGDVFIYNKDTLVI GVSERTNKEAILTIAKKIKNNKEAKFKKIVAINVPPMPNLMHLDTWLTMVDKDKF LYSPNMLSVLKVWEIDL5KEIEMVETNKPLADVLES11GVKPVLIPIAGKGATQL DIDIETHFDGTNYLTIAPGVVVGYSRNIKTEAALRAAGVTVLSFEGNQLSLGMGS ARCHSMPLVREDVK | 31 |
| C4DS6 | MSKINVYSEIGELKEVLVHTPGDEIRRISPSRLDELLFSAILEPNEAIKEHKGFL KILQDKGIKVIQLTDLVAETFDLASKEEQEKLIEEFLEDSEPVLSEAHKTAVRKF LTSRKSTREMVEFMMAGITKYDLGIEADHELIVDPMPNLYFTRDPFASAGNGISL MNMKYVTRKRETIFAEFIFATHPDYKTTPHWFDRLDEGNIEGGDVFIYNKDTLVI GVSERTNKEAILTIAKKIKNNKEAKFKKIVAINVPPMPNLMHLDTWLTMVDKDKF LYSPNMLSVLKVWEIDLSKEIEMVETKKPLADVLESIIGVKPVLIPIAGKGATQL DIDIETKFDGTNYLTIAPGVVVGYSRNIKTEAALRAAGVTVLSFEGNQLSLGMGS ARCMSMPLVREDVK | 32 |
| C4DS7 | MSKINVYSEIGELKEVLVHTPGDEIRRISPSRLDELLFSAILEPNEAIKEHKGFL KILQDKGIKVIQLTDLVSETYDMVSKEKQEKLIEEFLEDSEPVLSEEKKGLVRKF LKSLKSSKELIQYMMAGITKHDLNIEADHELIVDPMFNLYFTRDPFASAGNGISL NNMKYVTRKRETIFAEFIFATHPDYKTTPHWFDRLDEGNIEGGDVFIYNKDTLVI GVSERTNKEAILTIAKKIKNNKEAKFKKIVAINVPPMPNLMHLDTWLTMVDKDKF LYSPNMLSVLKVWEIDLSKEIEMVETNKPLADVLESIIGVKPVLIPIAGKGATQL DIDIETHFDGTNYLTIAPGVVVGYSRNIKTEAALRAAGVTVLSFEGNQLSLGMGS ARCMSMPLVREDVK | 33 |
| C4DS8 | MSKINVYSEIGELKEVLVHTPGDEIRRISPSRLDELLFSAILEPNEAIKEHKGFL KILQDKGIKVIQLSDLVAETYVKYATAEQKAAFIEKYLDEATPALSAENRERAKK YILSLEMQPVKMIRTMMAGLSKYELNVESNIELIIDPMPNLYFTRDPFASAGNGI SLNNMKYVTRKRETIFAEFIFATHPDYKTTPHWFDRLDEGNIEGGDVFIYNKDTL VIGV8ERTNKEAILTIAKKIKNNKEAKFKKIVAINVPPMPNLMHLDTWLTMVDKD KFLYSPNMLSVLKVWEIDLSKEIEMVETNKPLADVLE311GVKPVLIPXAGKGAT QLDIDIETHFDGTMYLTIAPGVVVGYSRNIKTEAALRAAGVTVLSFEGNQLSLGM GSARCMSMPLVREDVK | 34 |
| C4DS9 | MSKINVYSEIGELKEVLVHTPGDEIRRTSPSRLDELLFSAILEPNEAIKEHKGFL KILQDKGIKVIQLSDLVAETYKHYASEAEKEAFIEKYLDEATPVLSKDMRAKVKN | 35 |

TABLE A2-continued

Chimeric ADI

| Name | Sequence | SEQ ID NO: |
|---|---|---|
|  | YILSMQGEPVKMVRTMMAGVSKQELNVESEVELIVDPMPNLYFTRDPFASAGNGI SLNNMKYVTRKRETIFAEFIFATHPDYKTTPHWFDRLDEGNIEGGDVFIYNKDTL VIGVSERTNKEAILTIAKKIKNKKEAKFKKIVAINVPPMPNLMHLDTWLTMVDKD KFLYSPNMLSVLKVWEIDLSKEIEMVETNKPLADVLESIIGVKPVLIPIAGKGAT QLDIDIETHFDGTNYLTIAPGVVVGYSRNIKTEAALRAAGVTVLSFEGMQLSLGM GSARCMSMPLVREDVK |  |
| C5DS1 | MSVFDSKFNGIHVYSETGELESVLVHEPGREIDYITPARLDELLFSATLESHDAR KEKKLFVSELKANDINVVELDELVAQTYDQVDQKIKDEFIDQWLQEAKPVLNDQL KKLVKNYLLKSQKEFSTKKMVRIMMAGIDKKEINIDLDRDLVVDPMPNLYFTRDP FASVGNGVTIKYMRYKVRQRETLFSRVFSMHPKLVNTPWYYDPSLKLSIEGGDV FIYNNNTLVVGVSERTDLETVTLLAKNIVANKECEFKRIVAINVPKWTNLMHLDT WLTMLDKDKFLYSPIANDVFKFWDYDLVNGGEEPQPVENGLPLEGLLESIINKKP ILIPIAGEGASQIDIERETHFDGTNYLAIRPGVVIGYSRNEKTNAALEAAGIKVL PFKGNQLSLGMGNARCMSMPLSRKDVKW | 36 |
| C5DS2 | MSVFDSKFNGIHVYSEIGELESVLVHEPGREIDYITPARLDELLFSAILESRDAR KEHKLFVSELKANDINVVELIDLVAETYDLASQEAKDKLIEEFLEDSEPVLSEEH KVVVRNFLKAKKTSRELVEIMMAGITKYDLGIEADHELIVDPMPNLYFTRDPFAS VGNGVTIHYMRYKVRQRETLFSRFVFSNHPKLVNTPWYYDPSLKLSIEGGDYFIY NNNTLWGVSERTDLETVTLLAKNIVANKECEFKRIVAINVPK'WTNLMHLDTWLT MLDKDKFLYSPIANDVFKFWDYDLVNGGEEPQPVENGLPLEGLLESIINKKPILI PIAGEGASQIDIERETHFDGTNYLAIRPGWIGYSRNEKTNAALEAJiGIKVLPFH GNQLSLGMGNARCMSMPLSRKDVKW | 37 |
| C5DS3 | MSVFDSKFNGIHVYSEIGELESVLVHEPGREIDYITPARLDELLFSAILESHEAR KEHKLFVSELKANDINVVELVDLIVETYDLASKEAKEKLLEEFLDDSVPVLSDEH RATVKKFLQSQKSTRSLVEYMIAGITKHDLKIESDLELIVDPMPNLYFTRDPFAS VGNGVTIHYMRYKVRQRETLFSRFVFSNHPKLVNTPWYYDPSLKLSIEGGDVFIY NNNTLVVGVSERTDLETVTLLAKNIVANKECEFKRIVAINVPKWTNLMHLDTWLT MLDKDKFLYSPIANDVFKFWDYDLVNGGEEPQPVENGLPLEGLLESIINKKPILI PIAGEGASQIDIERETHFDGTNYLAIRPGVVIGYSRNEKTNAALEAAGIKVLPFH GNQLSLGMGNARCMSMPLSRKDVKW | 38 |
| C5DS4 | MSVFDSKFNGIHVYSEIGELESVLVHEPGREIDYITPARLDELLFSAILESHDAR KEHKLFVSELKANDINVVELSDLVAETYTYHATQKEREAFIEKWLDEAEPALTKD LRAKVKSYVLSKEGTPVAMVRTMMAGVSKQELNVESETELVVDPMPKLYFTRDPF ASVGNGVTIHYMRYKVRQRETLFSRFVFSNHPKLVNTPWYYDPSLKLSIEGGDVF IYNNNTLVVGVSERTDLETVTLLAKNIVANKECEFKRIVAINVPKWTNLMHLDTW LTMLDKDKFLYSPIANDVFKFWDYDLVNGGEEPQPVENGLPLEGLLESIINKKPI LIPIAGEGASQIDIERETHFDGTNYLAIRPGVVIGYSRNEKTNAALEAAGIKVLP FHGNQLSLGMGNARCMSMPLSRKDVKW | 39 |
| C5DS6 | MSVFDSKFNGTHVYSEIGELESVLVHEPGREIDYITPARLDELLFSAILESHDAR KEKKLFVSELKANDI1WVELTDLVAETFDLASKEEQEKLIEEFLEDSEPVLSEAH KTAVRKFLTSRKSTREMVEFMMAGITKYDLGIEADHELIVDPMPNLYFTRDPFAS VGNGVTIHYMRYKVRQRETLFSRFVFSNHPKLVNTPWYYDPSLKLSIEGGDVFIY NNNTLVVGVSERTDLETVTLLAKNIVANKECEFKRIVAINVPKWTNLMHLDTWLT MLDKDKFLYSPIANDVFKFWDYDLVNGGEEPQPVENGLPLEGLLESIINKKPILI PIAGEGASQIDIERETHFDGTNYLAIRPGVVIGYSRNEKTNAALEAAGIKVLPFH GNQLSLGMGNARCMSMPLSRKDVKW | 40 |
| C5DS7 | MSVFDSKFNGIHVYSEIGELESVLVHEPGREIDYITPARLDELLFSAILESHDAR KEHKLFVSELKANDINVVELTDLVSETYDMVSKEKQEKLIEEFLEDSEPVLSEEH KGLVRKFLKSLKSSKELIQYMMAGITKHDLNIEADHELIVDPMPNLYFTRDPFAS VGNGVTIHYMRYKVRQRETLFSRFVFSNHPKLVNTPWYYDP8LKLSIEGGDVFIY NNNTLVVGVSERTDLETVTLLAKNIVANKECEFKRIVAINVPKWTNLMHLDTWLT MLDKDKFLYSPIANDVFKFWDYDLVMGGEEPQPVENGLPLEGLLESIINKKPILI PIAGEGASQIDIERETHFDGTNYLAIRPGVVIGYSRNEKTNAALEAAGIKVLPFH GNQLSLGMGNARCMSMPLSRKDVKW | 41 |
| C6DS1 | MSVFDSKFNGIKVYSEIGELETVLVHEPGREIDYITPARLDELLFSAILESKDAR KEHQSFVKQLKDNGINVVELDELVAQTYDQVDQKIKDEFIDQWLQEAKPVLNDQL KKLVKNYLLKSQKEFSTKKMVRIMMAGIDKKEINIDLDRDLVVDPMPNLYFTRDP FASVGNGVTIKYMRYKVRQRETLFSRVFSNHPKLVKTPWYYDPAMKMSIEGGDV FIYNNDTLVVGVSERTDLETITLLAKNIKANKEVEFKRIVAINVPKWTNLMHLDT WLTMLDKDKFLYSPIANDVFKFWDYDLVNGGAEPQPKENGLPLEGLLQSIINKKP VLIPIAGNNASHIDIERETHFDGTNYLAIKPGVVIGYARNEKTNAALAAAGIKVL PFHGNQLSLGMGNARCMSMPLSRKDVKW | 42 |
| C6DS2 | MSVFDSKFNGIHVYSEIGELETVLVHEPGREIDYITPARLDELLFSAILESHDAR KEKQSFVKQLKDNGINVVELIDLVAETYDLASQEAKDKLIEEFLEDSEPVLSEEH KVVVRNFLKAKKTSRELVEIMHAGITKYDLGIEADHELIVDPMPNLYFTRDPFAS VGNGVTIHYMRYKVRQRETLFSRFVFSNHPKLVKTPWYYDFAMKMSIEGGDVFIY NNDTLVVGVSERTDLETITLLAKNIKANKEVEFKRIVAINVPKWTNLMHLDTWLT | 43 |

TABLE A2-continued

Chimeric ADI

| Name | Sequence | SEQ ID NO: |
|---|---|---|
|  | MLDKDKFLYSPIANDVFKFWDYDLVMGGAEPQPKENGLPLEGLLQSIINKKPVLI PIAGNNASHIDIERETHFDGTNYLAIKPGVVIGYARNEKTNAALAAAGIKVLPFH GNQLSLGMGNARCMSHPLSRKDVKW |  |
| C6DS3 | MSVFDSKFNGIKVYSEIGELETVLVHEPGREIDYITPARLDELLFSAILESHDAR KEHQSFVKQLKDNGINVVELVDLIVETYDLASKEAKEKLLEEFLDDSVPVLSDEH RATVKKFLQSKSTRSLVEYMIAGITKHDLKIESDLELIVDPMPNLYFTRDPFA8 VGNGVTIHYMRYKVRQRETLFSRFVFSNHPKLVKTPWYYDPAMKMSIEGGDVFIY NNDTLWGVSERTDLETITLLAKNIKANKEVEFKRIVAINVPKWTNLMPILDTWLT MLDKDKFLYSPIAMDVFKFWDYDLVNGGAEPQPKENGLPLEGLLQSIINKKPVLI PIAGNNASHIDIERETHFDGTNYLAIKPGVVIGYARNEKTNAALAAAGIKVLPFH GNGLSLGMGNARCMSMPLSRKDVKW | 44 |
| C6DS4 | MSVFDSKFNGIHVYSEIGELSTVLVHEPGREIDYITPARLDELLFSAILESHEAR KEHQSFVKQLKDMGINVVELSDLVAETYTYHATQKEREAFIEKWLDEAEPALTKD LRAKVKSYVLSKSGTPVAMVRTMMAGVSKQENLNVESETELVVDPMPNLYFTRDPF ASVGNGVTIHYMRYKVRQRETLFSRFVFSNHPKLVKTPWYYDPAMKMSIEGGDVF IYNNDTLVVGVSERTDLETITLLAKNIKANKEVEFKRIVAINVPKWTNLMHLBTW LTMLDKDKFLYSPIANDVFKFWDYDLVNGGAEPQPKENGLPLEGLLQSIINKKPV LIPIAGNNASHIDIERETHFDGTNYLAIKPGVVIGYARNEKTNAALAAAGIKVLP FHGNQLSLGMGNARCMSMPLSRKDVKW | 45 |
| C6DS5 | MSVFDSKFNGIHVYSEIGELETVLVHEPGREIDYITPARLDELLFSAILESKDAR KEHQSFVKQLKDNGINVVELTDLVTETYDLASQEAKDNLIEEFLEDSEPVLTEEL KSVVRTYLKSIKSTRELIQMMMAGITKYDLGIEADHELIVDPMPNLYFTRDPFAS VGNGVTIHYMRYKVRQRETLFSRFVFSNHPKLVKTPWYYDPAMKMSIEGGDVFIY NNDTLVVGVSERTDLETITLLAKNIKANKEVEFKRIVAINVPKWTNLMHLDTWLT MLDKDKFLYSPIANDVFKFWDYDLVNGGAEPQPKENGLPLEGLLQSIINKKPVLI PIAGNNASHIDIERETHFDGTNYLAIKPGVVIGYARNEKTNAALAAAGIKVLPFH GNQLSLGMGNARCMSFLSRKDVKW | 46 |
| C6DS7 | MSVFDSKFNGIHVYSEIGELETVLVHEPGREIDYITPARLDELLFSAILESHDAR KEHQSFVKQLKDNGINVVELTDLVSETYDMVSKEKQEKLIEEFLEDSEPVLSEEH KGLVRKFLKSLKSSKELIQYMMAGITKHDLNIEADHELIVDPMPNLYFTRDPFAS VGNGVTIHYMRYKVRQRETLFSRFVFSNHPKLVKTPWYYDPAMKMSIEGGDVFIY NNDTLVVGVSERTDLETITLLAKNIKANKEVEFKRIVAINVPKWTNLMHLDTWLT MLDKDKFLYSPIANDVFKFWDYDLVNGGAEPQPKENGLPLEGLLQSIINKKPVLI PIAGNNASHIDIERETHFDGTNYLAIKPGVVIGYARNEKTNAALAAAGIKVLFFH GNQLSLGMGNARCMSMPLSRKDVKW | 47 |
| C7DS1 | MSVFDSKFNGIHVYSEIGELQTVLVHEPGREISYITPARLDELLFSAILESHDAR KEHQEFVAELKKNNINVVELDELVAQTYDQVDQKIKDEFIDQWLQEAKPVLNDQL KKLVKNYLLKSQKEFSTKKMVRIMMAGIDKKEINIDLDRDLVVDFMPNLYFTRDP FASVGNGVTIKYMRYKVRQRETLFSRFIFANHPKLMNTPLYYNPDMKLSIEGGDV FVYNNETLVVGVSERTDLDTITLLAKNIKANKEREFKRIVAINVPKWTNLMHLDT WLTMLDKDKFLYSPIANDVFKFWDYDLVNGGDEPQPKVGLPLEKLLESIINKKP ILIPIAGTSASNIDVERETKFDGTNYIAIAPGVVIGYSRNVKTNEALEAAGIKVL PFKGNQLSLGMGNARCMSMPLSRKDVKW | 48 |
| C7DS2 | MSVFDSKFNGIHVYSEIGELQTVLVHEPGREIEYITPARLDELLFSAILESKBAR KEKQEFVAELKKNNINVVELIDLVAETYDLASQEAKDKLIEEFLEDSEFVLSEEH KVVVRNFLKAKKTSRELVEIMMAGITKYDLGIEADHELIVDPMPNLYFTRDPFAS VGNGVTIHYMRYKVRQRETLFSRFIFANHPKLMNTPLYYNPDMKLSIEGGDVFVY NNETLVVGVSERTDLDTITLLAKNIKANKEREFKRIVAINVPKWTNLMHLDTWLT MLDKDKFLYSPIANDVFKFWDYDLVNGGDEPQPKVNGLPLEKLLESIINKKPILI PIAGTSASNIDVERETHFDGTNYLAIAPGVVIGYSRNVKTNEALEAAGIKVLFFK GNQLSLGMGNARCMSMPLSRKDVKW | 49 |
| C7DS3 | MSVFDSKFNGIHVYSEIGELQTVLVHEPGREIEYITFARLDELLFSAILESHDAR KEHQEFVAELKKNNINVVELVDLIVETYDLASKEAKEKLLEEFLDDSVPVLSDEH RATVKKFLQSKSTRSLVEYMIAGITKHDLKIESDLELIVDPMPMLYFTRDPFAS VGNGVTIHYMRYKVRQRETLFSRFIFANHPKLMNTPLYYNPDMKLSIEGGDVFVY NNETLVVGVSERTDLDTITLLAKNIKANKEREFKRIVAINVPKWTNLMHLDTWLT MLDKDKFLYSPIANDVFKFWDYDLVNGGDEPQPKVNGLPLEKLLESIINKKPILI PIAGTSASNIDVERETHFDGTNYLAIAPGVVIGYSRNVKTNEALEAAGIKVLPFK GNQLSLGMGNARCMSMPLSRKDVKW | 50 |
| C7DS4 | MSVFDSKFNGIHVYSEIGELQTVLVHEPGREIEYITPARLDELLFSATLESHDAR KEHQEFVAELKKNNINWELSDLVAETYTYHATQKEREAFIEKVJLDEAEPALTKD LRAKVKSYVLSKEGTPVAMVRTMMAGVSKQELNVESETELVVDPMPNLYFTRDPF ASVGNGVTIHYMRYKVRQRETLFSRFIFANKPKLMNTPLYYNPDMKLSIEGGDVF VYNNETLVVGVSERTDLDTITLLAKNIKANKEREFKRIVAINVPKWTNLHLDTW LTMLDKDKFLYSPIANDVFKFWDYDLVNGGDEPQPKVNGLPLEKLLESIINKKPI LIPIAGTSASNIDVERETHFDGTNYLAIAPGVVIGYSRKVKTNEALEAAGIKVLP FKGNQLSLGMGNARCMSMPLSRKDVKW | 51 |

TABLE A2-continued

Chimeric ADI

| Name | Sequence | SEQ ID NO: |
|---|---|---|
| C7DS5 | MSVFDSKFNGIHVYSEIGELQTVLVHEPGREIEYITPARLDELLFSAILESRDAR KEHQEFVAELKKNNINVVELTDLVTETYDLASQEAKDNLIEEFLEDSEPVLTEEL KSVVRTYLKSIKSTRELIQMMMAGITKYDLGIEADHELIVDPMPNLYFTRDPFAS VGNGVTIHYMRYKVRQRETLFSRFIFANHPKLMNTPLYYNPDMKLSIEGGDYFVY NNETLVVGVSERTDLDTITLLAKNIKANKEREFKRIVAINVPKWTNLMHLDTWLT MLDKDKFLYSPIANDVFKFWDYDLVNGGBEPQFKVNGLPLEKLLESIINKKPILI PIAGTSASNIDVERETHFDGTNYLAIAPGVVIGYSRNVKTNEALEAAGIKVLPFK GNQLSLGMGNARCMSMPLSRKDVKW | 52 |
| C7DS6 | MSVFDSKFNGIHVYSEIGELQTVLVHEPGREIEYITPARLDELLFSAILESHDAR KEKQEFVAELKKNNINVVELTDLVAETFBLASKEEQEKLIEEFLEDSEPVLSEAH KTAVRKFLTSRKSTREMVEFMMAGITKYDLGIEADHELIVDPMPNLYFTRDPFAS VGNGVTIHYMRYKVRQRETLFSRFIFANHPKLMNTPLYYNPDMKLSIEGGDVFVY NNETLVVGVSERTDLDTITLLAKNIKANKEREFKRIVAINVPKWTNLMHLDTWLT MLDKDKFLYSPIANDVFKFWDYDLVNGGDEPQPKVNGLPLEKLLESIINKKPILI PIAGTSASNIDVERETHFDGTNYLAIAPGVVIGYSRNVKTNEALEAAGIKVLPFK GNQLSLGMGNARCMSMPLSRKDVKW | 53 |
| C8DS3 | MSKIRVYSEIGNLKKVLVHTPGDEIRRISPSRLEELLFSAVLEPNAAIEEHKRFV KLLEDRGIQAIQLVDLIVETYDLASKEAKEKLLEEFLDDSVPVLSDEHRATVKKF LQSQKSTRSLVEYMIAGITKHDLKIESDLELIVDPMPNLYFTRDPFASAGNGISL NNMKYVVRKRETIFAEFIFAIHPEYKETPHWFDRLDHGSIEGGDVFVYNKDTLVI GVSERTNKEAIITIAKHIQDNKEAEFKKIVAINVPPMPNLMHLDTWLTMVDKNKF IYSPNMLSVLKIWEIDLAKPIEMVESNKSLTEVLESIIGEKPILIPIAGEGASQL DIDIETHFDGTNYLTIAPGVVVGYSRNEKTEKALKAAGITVLSFEGNQLSLGMGS ARCMSMPLVREDVK | 54 |
| C8DS4 | MSKIRVYSEIGNLKKVLVHTPGDEIRRISPSRLEELLFSAVLEPNAAIEEHKRFV KLLEDRGIQAIQLSDLVAETYTYHATQKEREAFIEKWLDEAEPALTKDLRAKVKS YVLSKEGTPVAMVRTMMAGVSKQELNVESETELVVDPMPNLYFTRDPFASAGNGI SLNNMKYVVRKRETIFAEFIFAIHPEYKETPHWFDRLDHGSIEGGDVFVYNKDTL VIGVSERTNKEAIITIAKHIQDNKEAEFKKIVAINVPPMPNLMHLDTWLTMVDKN KFIYSPNMLSVLKIWEIDLAKPIEMVESNKSLTEVLESIIGEKPILIPIAGEGAS QLDIDIETHFDGTNYLTIAPGVVVGYSRNEKTEKALKAAGITVLSFEGNQLSLGM GSARCMSMPLVREDVK | 55 |
| C8DS9 | MSKIRVYSEIGNLKKVLVHTPGDEIRRISPSRLEELLFSAVLEPNAAIEEHKRFV KLLEDRGIQAIQLSDLVAETYKHYASEAEKEAFIEKYLDEATPVLSKDMRAKVKN YILSMQGEPVKIWRTMMAGVSKQELNVESEVELIVDPMPNLYFTRDPFASAGNGI SLNNMKYVVRKRETIFAEFIFAIHPEYKETPHWFDRLDHGSIEGGDVFVYNKDTL VIGVSERTNKEAIITIAKHIQDNKEAEFKKIVAINVPPMPNLMHLDTWLTMVDKN KFIYSPNMLSVLKIWEIDLAKPIEMVESNKSLTEVLESIIGEKPILIPIAGEGAS QLDIDIETHFDGTNYLTIAPGVVVGYSRNEKTEKALKAAGITVLSFEGNQLSLGM GSARCMSMPLVREDVK | 56 |
| C9DS3 | MSKINVYSEIGVLKEVLVHTPGDEIRRIAPSRLDELLFSAILEPSAAIQEHKSFL KILQDRGIKTIQLVDLIVETYDLASKEAKEKLLEEFLDDSVPVLSDEHRATVKKF LQSQKSTRSLVEYMIAGITKHDLKIESDLELIVDPMPNLYFTRDPFASAGNGISL NNMKYVVRKRETIFAEFIFSIHPEYKKTPHWFDRLDNGSIEGGDVFIYNKDTLVI GVSERTNKEAIITIAKHIQDNKEAQFKKIVAINVPPMPNLMHLDTWLTMVDKNKF LYSPNMLSVLKVWEIDLSKPIEMVETNKPLAEVLESIIGEKPILIPIAGKDATQL DIDIETHFDGTNYLTIAPGVVVGYSRNVKTEAALRAAGVTVLSFEGNQLSLGMGS ARCMSMPLVREDVK | 57 |
| C9DS4 | MSKINVYSEIGVLKEVLVHTPGDEIRRIAPSRLDELLFSAILEPSAAIQEHKSFL KILQDRGIKTIQLSDLVAETYTYHATQKEREAFIEKWLDEAEPALTKDLRAKVKS YVLSKEGTPVAMVRTMMAGVSKQELNVESETELVVDPMPNLYFTRDPFASAGNGI SLNNMKYVVRKRETIFAEFIFSIKPEYKKTPKWFDRLDNGSIEGGDVFIYNKDTL VIGVSERTNKEAIITIAKHIQDNKEAQFKKIVAINVPPMPNLMHLDTWLTMVDKN KFLYSPNMLSVLKVWEIDLSKPIEMVETNKPLAEVLESIIGEKPILIPIAGKDAT QLDIDIETHFDGTNYLTIAPGVVVGYSRNVKTEAALRAAGVTVLSFEGNQLSLGM GSARCMSMPLVREDVK | 58 |
| C9DS8 | mskinvyseigvlkevlvhtpgdeirriapsrldellfsailepsaaiqehksfl kilqdrgiktiqlsdlvaetyvkyataeqkaafiekyldeatpalsaenrerakk yilslemqpvkmirtmmaglskyelnvesnieliidpmpnlyftrdpfasagngi slnnmkyvvrkretifaefifsihpeykktphwfdrldngsieggdvfiynkdtl vigvsertnkeaiitiakhiqdnkeaqfkkivainvppmpnlmhldtwltmvdkn kflyspnmlsvlkvweidlskpiemvetnkplaevlesiigekpilipiagkdat qldidiethfdgtnyltiapgvvvgysrnvkteaalraagvtvlsfegnqlslgm gsarcmsmplvredvk | 59 |

Hence, in some embodiments, the chimeric ADI comprises, consists, or consists essentially of an illustrative chimeric sequence from Table A2 (SEQ ID NOs:4-13 or 22-59), or a variant or fragment thereof having ADI activity.

Certain embodiments include variants of the reference ADI polypeptide sequences described herein, whether described by name or by reference to a sequence identifier (e.g., Tables A1-A2). A "variant" sequence, as the term is used herein, refers to a polypeptide or polynucleotide sequence that differs from a reference sequence disclosed herein by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within +2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In other specific embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In still other specific embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence.

Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.) Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Native ADI may be found in microorganisms and is immunogenic and rapidly cleared from circulation in a patient. These problems may be overcome by engineering ADI to reduce its antigenicity, such as by engineering chimeric ADI molecules. In one embodiment, chimeric ADI are constructed by combining different domains (e.g. catalytic domain and α-helical domains) from different ADI proteins using standard molecular biological, or protein synthesis techniques. In one embodiment, the catalytic domain from *M. arginini* or *M. arthritidis* is combined with the α-helical domain of *M. hominis*. In another embodiment, the catalytic domain of *M. arginini* is combined with the α-helical domain of *M. arthritidis*. In a further embodiment, the catalytic domain of *M. arthritidis* is combined with the α-helical domain of *M. arginini*. As would be recognized by the skilled person, other combinations of catalytic and α-helical domains can be constructed from ADI proteins derived from other species, such as from *Mycoplasma pneumoniae, Steptococcus pyogenes, Steptococcus pneumoniae, Borrelia burgdorferi, Borrelia afzelii, Giardia intestinalis, Clostridium perfringens, Bacillus licheniformis, Enterococcus faecalis*, and *Lactobacillus sake*.

Antigenicity problems may also be overcome by modifying chimeric ADI. Thus, the present disclosure provides chimeric ADI modified by a modifying agent, including, but not limited to macromolecule polymers, proteins, peptides, polysaccharides, or other compounds. Arginine deiminase or chimeras thereof as described herein and the modifying agent may be linked by either covalent bonds or non-covalent interaction to form a stable conjugate or a stable composition to achieve a desired effect. In certain embodiments, the modified chimeric ADI retains the biological activity of an unmodified chimeric ADI and has a longer half-life in vivo and lower antigenicity than the unmodified, chimeric ADI. In certain embodiments, the modified chimeric ADI retains at least 20%, 25%, 30%, 35%, 40%, 45%, 50%, 55%, 60%, 65%, 70%, 75%, 80%, 85%, 90%, 95%, 96%, 97%, 98%, 99% or more of the biological activity of unmodified chimeric ADI.

In one embodiment, a modifying agent can be a polymer or a protein or a fragment thereof that is biocompatible and can increase the half-life of chimeric ADI in blood. The modifying agent can be either chemically coupled to chimeric ADI or where applicable, linked to the chimeric ADI via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, polyacryloyl morpholines, copolymer of amino compounds and oxyolefin, poly hyaluronic acid, polyoxiranes, copolymer of ethanedioic acid and malonic acid, poly (1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol (HO((CH2)$_x$O)nH), polypropylene glycol, polyoxyrehylene (HO((CH$_2$)$_2$O)$_n$H), polyvinyl alcohol ((CH$_2$CHOH)$_n$).

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In one specific embodiment of the present invention, chimeric ADI is modified by coupling with proteins or peptides, wherein one or more proteins or peptides are directly or indirectly linked to chimeric ADI. The proteins can either be naturally existing proteins or their fragments, including but not limited to naturally existing human serum proteins or their fragments, such as thyroxine-binding protein, transthyretin, al-acid glycoprotein, transferrin, fibrinogen, immunoglobulin, Ig Fc regions, albumin, and fragments thereof. By "fragment" is meant any portion of a protein that is smaller than the whole protein but which retains the desired function of the protein. Engineered chimeric ADI may be directly or indirectly linked to a protein via a covalent bond. Direct linking means that one amino acid of chimeric ADI is directly linked to one amino acid of the modifying protein, via a peptide bond or a disulfide bridge. Indirect linking refers to the linkages between a chimeric ADI and a modifying protein, via originally existing chemical groups there between or specific chemical groups added through biological or chemical means, or the combination of the above-mentioned linkages.

In one particular embodiment, chimeric ADI is modified by covalent attachment with PEG. Chimeric ADI covalently modified with PEG (with or without a linker) may be hereinafter referred to as chimeric "ADI-PEG." When compared to unmodified chimeric ADI, chimeric ADI-PEG retains most of its enzymatic activity, is far less antigenic, has a greatly extended circulating half-life, and is much more efficacious in the treatment of tumors.

"Polyethylene glycol" or "PEG" refers to mixtures of condensation polymers of ethylene oxide and water, in a branched or straight chain, represented by the general formula H(OCH$_2$CH$_2$)nOH, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG 12,000 refers to PEG having a total weight average molecular weight of about 12,000; and PEG20,000 refers to PEG having a total weight average molecular weight of about 20,000.

In one embodiment of the present invention, the PEG has a total weight average molecular weight of about 1,000 to about 50,000; in one embodiment from about 3,000 to about 40,000, and in another embodiment from about 5,000 to about 30,000; in certain embodiments from about 8,000 to about 30,000; in other embodiments from about 11,000 to about 30,000; in additional embodiments, from about 12,000 to about 28,000; in still other embodiments, from about 16,000 to about 24,000; and in other embodiments, about 18,000 to about 22,000; in another embodiment, from 19,000 to about 21,000, and in one embodiment, the PEG has a total weight average molecular weight of about 20,000. Generally, PEG with a molecular weight of 30,000 or more is difficult to dissolve, and yields of the formulated product may be reduced. The PEG may be a branched or straight chain. Generally, increasing the molecular weight of the PEG decreases the immunogenicity of the ADI or chimeric ADI. The PEG having a molecular weight described in this embodiment may be used in conjunction with chimeric ADI, and, optionally, a biocompatible linker, to treat cancer, including, for example, acute myeloid leukemia, such as relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, stomach cancer and esophageal cancer.

In another embodiment of the present invention, the PEG has a total weight average molecular weight of about 1,000 to about 50,000; in certain embodiments about 3,000 to about 30,000; in other embodiments from about 3,000 to about 20,000; in one embodiment from about 4,000 to about 12,000; in still other embodiments from about 4,000 to about 10,000; in additional embodiments from about 4,000 to about 8,000; still further embodiments from about 4,000 to about 6,000; and about 5,000 in another embodiment. The PEG may be a branched or straight chain, and in certain embodiments is a straight chain. The PEG having a molecular weight described in this embodiment may be used in conjunction with chimeric ADI, and optionally, a biocompatible linker, to treat graft versus host disease (GVHD) or cancer.

While chimeric ADI-PEG is the illustrative modified chimeric ADI described herein, as would be recognized by the skilled person chimeric ADI may be modified with other polymers or appropriate molecules for the desired effect, in particular reducing antigenicity and increasing serum half-life.

Chimeric ADI may be covalently bonded to a modifying agent, such as PEG, with or without a linker, although a preferred embodiment utilizes a linker.

The linker used to covalently attach chimeric ADI to a modifying agent, e.g. PEG, may be any biocompatible linker. As discussed above, "biocompatible" indicates that the compound or group is non-toxic and may be utilized in vitro or in vivo without causing injury, sickness, disease, or death. A modifying agent, such as PEG, can be bonded to the linker, for example, via an ether bond, a thiol bond, or an amide bond. The linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. In one embodiment, the source of the biocompatible linker is succinimidyl succinate (SS). Other suitable sources of linker may include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In another embodiment, the linker is derived from SS, SPA, SCM, or NHS; in certain embodiments, SS, SPA, or NHS are used, and in other embodiments, SS or SPA are used. Thus, in certain embodiments, potential linkers can be formed from methoxy-PEG succinimidyl succinate (SS), methoxy-PEG succinimidyl glutarate (SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and methoxy-PEG succinimidyl succinimide.

Alternatively, chimeric ADI may be coupled directly to a modifying agent, such as PEG (i.e., without a linker) through an amino group, a sulfhydryl group, a hydroxyl group or a carboxyl group.

Chimeric ADI may be covalently bonded to PEG, via a biocompatible linker, using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety.

The attachment of PEG to chimeric ADI increases the circulating half-life of chimeric ADI. Generally, PEG is attached to a primary amine of chimeric ADI. Selection of the attachment site of PEG, or other modifying agent, on the chimeric ADI is determined by the role of each of the sites within the active domain of the protein, as would be known to the skilled artisan. PEG may be attached to the primary amines of chimeric ADI without substantial loss of enzymatic activity. For example, ADI cloned from *Mycoplasma arginini*, *Mycoplasma arthritidis* and *Mycoplasma hominis* has a number of lysine residues that may be modified by this procedure. In other words, one or more or all of the lysines are possible points at which ADI and chimeric forms of ADI as described herein can be attached to PEG via a biocompatible linker, such as SS, SPA, SCM, SSA and/or NHS. PEG may also be attached to other sites on ADI and chimeric forms of ADI as described herein, as would be apparent to one skilled in the art in view of the present disclosure.

From 1 to about 30 PEG molecules may be covalently bonded to chimeric ADI. In certain embodiments, chimeric ADI is modified with one PEG molecule. In other embodiments, chimeric ADI is modified with more than one PEG molecule. In one embodiment, chimeric ADI is modified with about 1 to about 10 PEG molecules, in one embodiment from about 2 to about 8 PEG molecules and in another embodiment, from about 9 to about 12 PEG molecules. In another embodiment, the chimeric ADI is modified with 1, 2, 3, 4, 5, 6, 7, 8, 9, 10, 11, or 12 PEG molecules. In one specific embodiment, chimeric ADI is modified with 4.5-5.5 PEG molecules per ADI. In another embodiment, chimeric ADI is modified with 5±1.5 PEG molecules.

In another embodiment, about 15% to about 70% of the primary amino groups in chimeric ADI are modified with PEG, in one embodiment about 20% to about 65%, about 25% to about 60%, or in certain embodiments about 30% to about 55%, or 45% to about 50%, and in other embodiments about 20% or 30% or 40% or 50% of the primary amino groups in arginine deiminase are modified with PEG. As would be understood by the skilled artisan, the range of primary amino groups depends upon how many lysines are successfully removed. In certain embodiments, all of the lysines may be removed and the N-terminus of the molecule is PEGylated. When PEG is covalently bonded to the end terminus of chimeric ADI, it may be desirable to have only 1 PEG molecule utilized. Increasing the number of PEG units on chimeric ADI increases the circulating half-life of the enzyme. However, increasing the number of PEG units on chimeric ADI decreases the specific activity of the enzyme. Thus, a balance needs to be achieved between the two, as would be apparent to one skilled in the art in view of the present disclosure.

In the present invention, a common feature of biocompatible linker is that they attach to a primary amine of arginine deiminase via a succinyl group. Once coupled with chimeric ADI, SS-PEG has an ester linkage next to the PEG, which may render this site sensitive to serum esterase, which may release PEG from chimeric ADI in the body. SPA-PEG and PEG2-NHS do not have an ester linkage, so they are not sensitive to serum esterase.

In certain embodiments, a biocompatible linker is used in the present invention. PEG which is attached to the protein may be either a straight chain, as with SS-PEG, SPA-PEG and SC-PEG, or a branched chain of PEG may be used, as with PEG2-NHS.

In certain embodiments, the chimeric ADI of the present disclosure may be modified as described in U.S. Pat. No. 6,635,462. In particular, modifications of one or more of the naturally occurring amino acid residues of ADI and chimeric molecules of ADI, in particular derived from *Mycoplasma hominis, M. arthritidis* and *M. arginini*, can provide for an enzyme that is more easily renatured and formulated thereby improving existing techniques for the manufacture of chimeric ADI and therapeutic compositions comprising the same. In one embodiment, the chimeric ADI of the present disclosure is modified to remove one or more lysine residues (e.g., the lysine can be substituted with another amino acid or analogues thereof, or a non-natural amino acid). In particular, in one embodiment, the chimeric ADI is modified to be free of the lysine at position 112, 374, 405 or 408 of SEQ ID NO:1 (*M. hominis* ADI), or a combination of one or more of these positions. In a further embodiment, the chimeric ADI is modified to be free of one or more lysines, for example, 1, 2, 3, 4, 5, 6, 7, 8, 9, 10, 11, 12, 13, 14, 15, 16, 17, 18, 19, 20, 21, or more lysine residues, should they be present, can be substituted with another amino acid or analogues thereof, or a nonnatural amino acid. In one embodiment, a chimeric ADI has 5 lysines substituted, for example, at position 7, 88, 137, 209, and 380 of SEQ ID NO: 4. In another embodiment, a chimeric ADI has 10 lysines substituted, for example, at positions 7, 9, 59, 88, 115, 116, 137, 178, 209, and 380 of SEQ ID NO: 4. In yet another embodiment, a chimeric ADI has 15 lysines substituted, for example, at positions 7, 9, 59, 66, 88, 91, 93, 115, 116, 137, 141, 178, 209, 279, and at position 380 of SEQ ID NO: 4. In one embodiment, a chimeric ADI comprises 21 lysines substituted, for example, at positions 7, 9, 56, 59, 66, 88, 91, 93, 96, 115, 116, 137, 141, 178, 209, 254, 279, 325, 326, 380, and 406 of SEQ ID NO: 4. Illustrative chimeric ADI molecules having lysine substitutions are set forth in SEQ ID NOs: 10-13.

In certain embodiments, pegylation sites associated with ADI located at or adjacent to the catalytic region of the enzyme are modified. For purposes of the present invention, the phrase "pegylation site" may be defined as any site or position of ADI or a chimeric ADI that may be covalently modified with polyethylene glycol. A "pegylation site" can be considered located at or adjacent to the catalytic region of the enzyme where pegylation of the site results in a significant reduction in catalytic activity of the enzyme. The pegylation of such sites has traditionally resulted in the inactivation of the enzyme. For example, ADI from *Mycoplasma hominis* has a lysine at the 112 position which can be considered to be at or adjacent the catalytic region of the enzyme. The attachment of PEG to this lysine at the 112 position can inactivate the enzyme. In addition, ADI from *Mycoplasma hominis* has a cysteine at the 397 position which can be considered to be at or adjacent the catalytic region of the enzyme. The amino acid substitutions for cysteine at the 397 position can inactivate the enzyme. In particular, substituting alanine, histidine, arginine, serine, lysine or tyrosine for cysteine at the 397 position can result in a loss of all detectable enzyme activity. ADI from *Mycoplasma hominis* also has three lysines located near this conserved cysteine, in particular Lys374, Lys405 and Lys408. The attachment of PEG to Lys374, Lys405, Lys408 or combinations thereof can inactivate the enzyme.

It is to be understood that ADI derived from other organisms may also have pegylation sites corresponding to 112 position of ADI from *Mycoplasma hominis*. For example, ADI from *Steptococcus pyrogenes* has lysine at the 104 position, ADI from *Mycoplasma pneumoniae* has lysine at the 106 position, and ADI from *Giardia intestinalis* has lysine at the 114 position. In addition, ADI from some organisms may have lysines corresponding to the same general location as the 112 position of ADI from *Mycoplasma hominis*. The location of lysine in ADI from such organisms are known to the skilled person and are described in U.S. Pat. No. 6,635,462.

Thus, in one embodiment, the present invention provides for certain amino acid substitutions in the polypeptide chain of ADI. These amino acid substitutions provide for modified ADI that loses less activity when modified by a modifying agent, e.g., upon pegylation. By eliminating pegylation sites, or other known modification sites, at or adjacent to the catalytic region of enzyme, optimal modification, e.g., pegylation, can be achieved without the loss of activity.

It is to be understood that other embodiments of the invention are based on the understanding that certain structural characteristics of arginine deiminase may prevent or interfere with the proper and rapid renaturation when produced via recombinant technology. In particular, these structural characteristics hinder or prevent the enzyme from assuming an active conformation during recombinant production. For purposes of the present invention, the phrase "active conformation" may be defined as a three-dimensional structure that allows for enzymatic activity by unmodified or modified arginine deiminase or chimeric arginine deiminase. The active conformation may, in particular, be necessary for catalyzing the conversion of arginine into citrulline. The phrase "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominis* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma hominis*.

The present invention thus again provides for certain amino acid substitutions in the polypeptide chain of wild type arginine deiminases and chimeric arginine deiminases derived therefrom. Such amino acid substitutions can eliminate the problematic structural characteristics in the peptide chain of arginine deiminase. Such amino acid substitutions provide for improved renaturation of the modified arginine deiminase. These amino acid substitutions make possible rapid renaturing of modified chimeric arginine deiminases using reduced amounts of buffer. These amino acid substitutions may also provide for increased yields of renatured modified chimeric arginine deiminase. In one embodiment of the invention, the modified chimeric arginine deiminase has an amino acid substitution at P210 or the equivalent residue. As mentioned above, arginine deiminase derived from *Mycoplasma hominis* has the amino acid proline located at the 210 position. While not limiting the present invention, it is presently believed that the presence of the amino acid proline at position 210 results in a bend or kink in the normal polypeptide chain that increases the difficulty of renaturing (i.e., refolding) arginine deiminase. Substitutions for proline at position 210 make possible the rapid renaturation of modified arginine deiminase and chimeras derived therefrom using reduced amounts of buffer. Substitutions for proline at position 210 may also provide for increased yields of renatured modified chimeric arginase deiminase. In one embodiment, the proline at position 210 is substituted with serine. It is to be understood that in accordance with this aspect of the invention, other substitutions at position 210 may be made. Examples of other substitutions include Pro210 to Thr210, Pro210 to Arg210, Pro210 to Asn210, Pro210 to Gin210 or Pro210 to Met210. By eliminating those structural characteristics associated with the amino acid of position 210 of the wild-type arginine deiminase and chimeras derived therefrom, proper refolding of the enzyme can be achieved.

The methods of the present invention can involve either in vitro or in vivo applications. In the case of in vitro applications, including cell culture applications, the compounds described herein can be added to the cells in cultures and then incubated. The compounds of the present invention may also be used to facilitate the production of monoclonal and/or polyclonal antibodies, using antibody production techniques well known in the art. The monoclonal and/or polyclonal antibodies can then be used in a wide variety of diagnostic applications, as would be apparent to one skilled in the art.

The in vivo means of administration of the compounds of the present invention will vary depending upon the intended application. Administration of the chimeric ADI compositions described herein, in pure form or in an appropriate pharmaceutical composition, can be carried out via any of the accepted modes of administration of agents for serving similar utilities. The pharmaceutical compositions can be prepared by combining chimeric ADI, e.g., chimeric ADI-PEG, chimeric ADI-PEG 20, with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Modes of administration depend upon the nature of the condition to be treated or prevented. Thus, chimeric ADI-PEG, e.g., chimeric ADI-PEG 20, may be administered orally, intranasally, intraperitoneally, parenterally, intravenously, intralymphatically, intratumorly, intramuscularly, interstitially, intra-arterially, subcutaneously, intraocularly, intrasynovial, transepithelial, and transdermally. An amount that, following administration, reduces, inhibits, prevents or delays the progression and/or metastasis of a cancer is considered effective. In certain embodiment, the chimeric ADI compositions herein increase median survival time of patients by a statistically significant amount. In one embodiment, the chimeric ADI treatments described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, chimeric ADI treatments increase median survival time of a patient by 1 year, 2 years, 3 years, or longer. In one embodiment, the chimeric ADI treatments described herein increase progression-free survival by 2 weeks, 3 weeks, 4 weeks, 5 weeks, 6 weeks, 7 weeks, 8 weeks, 9 weeks, 10 weeks or longer. In certain embodiments, the chimeric ADI treatments described herein increase progression-free survival by 1 year, 2 years, 3 years, or longer.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In certain embodiments, the amount administered is sufficient to result in stable disease. In other embodiments, the amount administered is sufficient to result in clinically relevant reduction in symptoms of a particular disease indication known to the skilled clinician.

In certain embodiments the amount administered is sufficient to inhibit NO synthesis, inhibit angiogenesis, and or is sufficient to induce apoptosis in tumor cells or any combination thereof. NO synthesis, angiogenesis and apoptosis may be measured using methods known in the art, see, e.g., *Current Protocols in Immunology or Current Protocols in Molecular Biology*, John Wiley & Sons, New York, N.Y. (2009 and updates thereto); Ausubel et al., *Short Protocols in Molecular Biology*, 3 ed., Wiley & Sons, 1995; and other like references. In one particular embodiment the amount administered inhibits NO synthesis and inhibits the growth of melanoma and synergizes with other chemotherapies as described herein, such as cisplatin. Accordingly, one embodiment of the present disclosure provides a method of treating melanoma by administering chimeric ADI-PEG 20 in combination with cisplatin, wherein the treatment depletes endogenous nitric oxide (NO).

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The chimeric ADI compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described chimeric ADI composition in aerosol form may hold a plurality of dosage units. Actual methods of preparing such dosage forms are known, or will be apparent, to those skilled in this art; for example, see

*Remington: The Science and Practice of Pharmacy,* 20th Edition (Philadelphia College of Pharmacy and Science, 2000). The composition to be administered will, in any event, contain a therapeutically effective amount of a chimeric ADI-PEG of the present disclosure, such as chimeric ADI-PEG 20, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, anoral oil, injectable liquid or an aerosol, which is useful in, for example, inhalatory administration. When intended for oral administration, the pharmaceutical composition is generally either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, in certain embodiments, physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of chimeric ADI as herein disclosed, such as chimeric ADI-PEG 20, such that a suitable dosage will be obtained. Typically, this amount is at least 0.01% of chimeric ADI in the composition. When intended for oral administration, this amount may be varied to be between 0.1 and about 70% of the weight of the composition. Certain oral pharmaceutical compositions contain between about 4% and about 75% of chimeric ADI-PEG. In certain embodiments, pharmaceutical compositions and preparations according to the present invention are prepared so that a parenteral dosage unit contains between 0.01 to 10% by weight of chimeric ADI-PEG prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to chimeric ADI-PEG and thereby assists in the delivery of the compound. Suitable agents that may act in this capacity include monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises chimeric ADI-PEG as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the chimeric ADI-PEG composition so as to facilitate dissolution or homogeneous suspension of the chimeric ADI-PEG in the aqueous delivery system.

The compositions may be administered in a therapeutically effective amount, which will vary depending upon a variety of factors including the activity of the specific compound (e.g., chimeric ADI-PEG) employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

A therapeutically effective amount of one of the compounds of the present invention is an amount that is effective to inhibit tumor growth. Generally, treatment is initiated with small dosages which can be increased by small increments until the optimum effect under the circumstances is achieved. Generally, a therapeutic dosage of compounds of the present invention may be from about 1 to about 200 mg/kg twice a week to about once every two weeks. For example, the dosage may be about 1 mg/kg once a week as a 2 ml intravenous injection to about 20 mg/kg once every 3 days. In a further embodiment, the dose may be from about 50 $IU/m^2$ to about 8,000 $IU/m^2$, administered about once every 3 days, about once a week, about twice a week, or about once every 2 weeks. In certain embodiments, the dose may be about 50 $IU/m^2$, 60 $IU/m^2$, 70 $IU/m^2$, 80 $IU/m^2$, 90 $IU/m^2$, 100 $IU/m^2$, 110 $IU/m^2$, 120 $IU/m^2$, 130 $IU/m^2$, 140 $IU/m^2$, 150 $IU/m^2$, 160 $IU/m^2$, 170 $IU/m^2$, 180 $IU/m^2$, 190 $IU/m^2$, 200 $IU/m^2$, 210 $IU/m^2$, 220 $IU/m^2$, 230 $IU/m^2$, 240 $IU/m^2$, 250 $IU/m^2$, 260 $IU/m^2$, 270 $IU/m^2$, 280 $IU/m^2$, 290 $IU/m^2$, 300 $IU/m^2$, 310 $IU/m^2$, about 320 $IU/m^2$, about 330 $IU/m^2$, 340 $IU/m^2$ about 350 $IU/m^2$, 360 $IU/m^2$, 370 $IU/m^2$, 380 $IU/m^2$, 390 $IU/m^2$, 400 $IU/m^2$, 410 $IU/m^2$, 420 $IU/m^2$, 430 $IU/m^2$, 440 $IU/m^2$, 450 $IU/m^2$, 500 $IU/m^2$, 550 $IU/m^2$, 600 $IU/m^2$, 620 $IU/m^2$, 630 $IU/m^2$, 640 $IU/m^2$, 650 $IU/m^2$, 660 $IU/m^2$, 670 $IU/m^2$, 680 $IU/m^2$, 690 $IU/m^2$, 700 $IU/m^2$, 750 $IU/m^2$, 800 $IU/m^2$, 850 $IU/m^2$, 900 $IU/m^2$, 950 $IU/m^2$, 1,000 $IU/m^2$, 1,100 $IU/m^2$, 1,200 $IU/m^2$, 1,300 $IU/m^2$, 1,400 $IU/m^2$, 1,500 $IU/m^2$, 1,600 $IU/m^2$, 1,700 $IU/m^2$, 1,800 $IU/m^2$, 1,900 $IU/m^2$, 2,000 $IU/m^2$, 2,100 $IU/m^2$, 2,200 $IU/m^2$, 2,300 $IU/m^2$, 2,400 $IU/m^2$, 2,500 $IU/m^2$, 2,600 $IU/m^2$, 2,700 $IU/m^2$, 2,800 $IU/m^2$, 2,900 $IU/m^2$, 3,000 $IU/m^2$, 3,100 $IU/m^2$, 3200 $IU/m^2$, 3,300 $IU/m^2$, 3,400 $IU/m^2$, 3,500 $IU/m^2$, 3,600 $IU/m^2$, 3,700 $IU/m^2$, 3,800 $IU/m^2$, 3,900 $IU/m^2$, 4000 $IU/m^2$, 4,100 $IU/m^2$, 4,200 $IU/m^2$, 4,300 $IU/m^2$, 4,400 $IU/m^2$, 4,500 $IU/m^2$, 4,600 $IU/m^2$, 4,700 $IU/m^2$, 4,800 $IU/m^2$, 4,900 $IU/m^2$, 5,000 $IU/m^2$, 5,100 $IU/m^2$, 5,200 $IU/m^2$, 5,300 $IU/m^2$, 5,400 $IU/m^2$, 5,500 $IU/m^2$, 5,600 $IU/m^2$, 5,700 $IU/m^2$, 5,800 $IU/m^2$, 5,900 $IU/m^2$, 6,000 $IU/m^2$, 6,100 $IU/m^2$, 6,200 $IU/m^2$, 6,300 $IU/m^2$, 6,400 $IU/m^2$, 6,500 $IU/m^2$, 6,600 $IU/m^2$, 6,700 $IU/m^2$, 6,800 $IU/m^2$, 6,900 $IU/m^2$, 7,000 $IU/m^2$, 7,100 $IU/m^2$, 7,200 $IU/m^2$, 7,300 $IU/m^2$, 7,400 $IU/m^2$, 7,500 $IU/m^2$, 7,600 $IU/m^2$, 7,700 $IU/m^2$, 7,800 $IU/m^2$, 7,900 $IU/m^2$, or about 8,000 $IU/m^2$ administered about once every 3 days, about once a week, about twice a week, or about once every 2 weeks. In some embodiments, the dose may be about 1 $mg/m^2$, 2 $mg/m^2$, 3 $mg/m^2$, 4 $mg/m^2$, 5 $mg/m^2$, 6 $mg/m^2$, 7 $mg/m^2$, 8 $mg/m^2$, 9 $mg/m^2$, 10 $mg/m^2$, 15 $mg/m^2$, 20 $mg/m^2$, 25 $mg/m^2$, 30 $mg/m^2$, 35 $mg/m^2$, 40 $mg/m^2$, 45 $mg/m^2$, 50 $mg/m^2$, 55 $mg/m^2$, 60 $mg/m^2$, 65 $mg/m^2$, 70 $mg/m^2$, 75 $mg/m^2$, or about 80 $mg/m^2$ administered about once every 3 days, about once a week, about twice a week, or about once every 2 weeks.

In certain embodiments, the dose may be modified as desired by the skilled clinician. In some embodiments, the optimum dosage with chimeric ADI-SS-PEG5,000 may be about twice a week, while the optimum dosage with chimeric ADI-SS-PEG20,000 may be from about once a week to about once every two weeks. In certain embodiments, the optimum dosage with chimeric ADI-SS-PEG20,000 may be about twice a week.

Chimeric ADI-PEG may be mixed with a phosphate buffered saline solution, or any other appropriate solution known to those skilled in the art, prior to injection. In one embodiment, a liquid composition comprising chimeric ADI-PEG comprises about 10 to about 12 mg of chimeric ADI, about 20 to about 40 mg of polyethylene glycol, 1.27 mg+5% monobasic sodium phosphate, USP; about 3 mg+5% dibasic sodium phosphate, USP; 7.6 mg+5% sodium chloride, USP; at a pH of about 6.6 to about 7; in an appropriate amount of water for injection (e.g., about 1 ml or about 2 ml). In one embodiment, a liquid composition comprising a chimeric ADI-PEG comprises histidine-HCl, and in certain embodiments, the composition buffer is from about 0.0035M Histidine-HCl to about 0.35M Histidine-HCl. In one particular embodiment, the composition is formulated in a buffer comprising 0.035 M Histidine-HCl at pH 6.8 with 0.13 M sodium chloride. In another embodiment, the composition is formulated in a buffer comprising 0.02M sodium phosphate buffer at pH 6.8 with 0.13 M sodium chloride.

In one embodiment, a composition comprising chimeric ADI or chimeric ADI-PEG has a pH of about 5 to about 9, about 6 to about 8, or about 6.5 to about 7.5. In some embodiments, the composition comprising chimeric ADI has a pH of about 6.8±1.0.

In one embodiment, free PEG in a composition comprising chimeric ADI-PEG is between 1-10%, and in a further embodiment, is less than 7%, less than 6%, less than 5%, less than 4%, less than 3%, less than 2% or less than 1% of the total PEG. In certain embodiments, the unmodified chimeric ADI in a composition comprising chimeric ADI-PEG is less than about 1%, 0.9%, 0.8%, 0.7%, 0.6%, 0.5%, 0.4%, 0.3%, 0.2% or less than 0.1%. Generally, compositions comprising chimeric ADI-PEG have total impurities less than or equal to about 4%, 3%, 2%, 1.5%, 1% or 0.5%. In one embodiment, the endotoxin limit meets the requirements stated in USP, i.e., ≤50 EU/mL.

In one embodiment, the free sulfhydryl in a composition comprising chimeric ADI or chimeric ADI-PEG is greater than about 90%. In some embodiments, the free sulfhydryl in a composition comprising chimeric ADI or chimeric ADI-PEG is about 91%, about 92%, about 93%, about 94% or about 95%, about 96% about 97%, about 98% about 99% or more.

In one embodiment, the chimeric ADI or chimeric ADI-PEG in a composition has a Km of from about 0.5 µM to about 15 µM, and in a further embodiment, is from about 1 µM to about 12 µM, about 1 µM to about 10 µM, about 1.5 µM to about 9 µM, about 1.5 µM to about 8 µM or about 1.5 µM to about 7 µM. In certain embodiments, the chimeric ADI or chimeric ADI-PEG in a composition has a Km of about 1.5 µM to about 6.5 µM. In some embodiments, the chimeric ADI or chimeric ADI-PEG in a composition has a Km of about 1.5 µM, about 2 µM, about 2.5 µM, about 3 µM, about 3.5 µM, about 4 µM, about 4.5 µM, about 5 µM, about 5.5 µM, about 6 µM, about 6.5 µM, or about 7 µM. In one embodiment, the chimeric ADI or chimeric ADI-PEG in a composition has a reduced Km compared to a wild type ADI or wild type ADI-PEG in the composition.

In one embodiment, the chimeric ADI or chimeric ADI-PEG in a composition has a Kcat of from about 0.5 $sec^{-1}$ to about 15 sec$^{-1}$, and in a further embodiment, is from about 1 sec$^{-1}$ to about 12 sec$^{-1}$, about 1 sec$^{-1}$ to about 10 sec$^{-1}$, about 1.5 sec$^{-1}$ to about 9 sec$^{-1}$, about 2 sec$^{-1}$ to about 8 sec$^{-1}$ or about 2.5 sec$^{-1}$ to about 7 sec$^{-1}$. In certain embodiments, the chimeric ADI or chimeric ADI-PEG in a composition has a Kcat of about 2.5 sec$^{-1}$ to about 7.5 sec$^{-1}$. In some embodiments, the chimeric ADI or chimeric ADI-PEG in a composition has a Kcat of about 2.5 sec$^{-1}$, about 3 sec$^{-1}$, about 3.5 sec$^{-1}$, about 4 sec$^{-1}$, about 4.5 sec$^{-1}$, about 5 sec$^{-1}$, about 5.5 sec$^{-1}$, about 6 sec$^{-1}$, about 6.5 sec$^{-1}$, about 7 sec$^{-1}$, about 7.5 sec$^{-1}$ or about 8 sec. In one embodiment, the chimeric ADI or chimeric ADI-PEG in a composition has a higher Kcat than a wild type ADI or wild type ADI-PEG in the composition.

In one embodiment, the chimeric ADI or chimeric ADI-PEG in a composition has a conductivity (also referred to in the art as specific conductance) of about 5 mS/cm to about 20 mS/cm, and in further embodiments, from about 5 mS/cm to about 15 mS/cm, about 7 mS/cm to about 15 mS/cm, about 9 mS/cm to about 15 mS/cm or about 10 mS/cm to about 15 mS/cm. In some embodiments, the chimeric ADI or chimeric ADI-PEG in a composition has a conductivity of about 9 mS/cm, about 10 mS/cm, about 11 mS/cm, about 12 mS/cm or about 13 mS/cm, about 14 mS/cm or about 15 mS/cm. In certain embodiments, the chimeric ADI or chimeric ADI-PEG in a composition has a conductivity of about 13 mS/cm±1.0 mS/cm.

In one embodiment, the chimeric ADI or chimeric ADI-PEG in a composition has an osmolality of about 50 mOsm/kg to about 500 mOsm/kg, about 100 mOsm/kg to about 400 mOsm/kg, about 150 mOsm/kg to about 350 mOsm/kg, about 200 mOsm/kg to about 350 mOsm/kg or about 250 mOsm/kg to about 350 mOsm/kg. In certain embodiments, the chimeric ADI or chimeric ADI-PEG in a composition has an osmolality of about 300±30 mOsm/kg.

In one embodiment, the protein concentration is about 11.0±1.0 mg/mL. In certain embodiments, the protein concentration is between about 8 and about 15 mg/mL. In another embodiment, the protein concentration is about 8, 9, 10, 10.5, 11, 11.5, 12, 12.5, 13, 13.5, 14, or 15 mg/mL.

In one embodiment, the specific enzyme activity is between 1.0 and 150 IU/mg, where 1 IU is defined as the amount of enzyme that converts one μmol of arginine into one μmol of citrulline and 1 μmol of ammonia in one minute at 37° C. and the potency is 100±20 IU/mg. In another embodiment, the specific enzyme activity is about 5.5, 6, 6.5, 7, 7.5, 8, 8.5, 9.0, 9.5, 10, 10.5, 11, 11.5, 12, 12.5, 13, 13.5, 14, 14.5, 15, 16, 17, 18, 19, 20, 21,22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, or about 150±2.0 IU/mg. In one particular embodiment, the specific enzyme activity is 100±10.0 IU/mg.

Compositions comprising chimeric ADI-PEG of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising chimeric ADI-PEG (e.g., chimeric ADI-PEG 20) of the invention and each active agent in its own separate pharmaceutical dosage formulation. For example, chimeric ADI-PEG as described herein and the other active agent can be administered to the patient together in a single oral dosage composition such as a tablet or capsule, or each agent administered in separate oral dosage formulations. Similarly, chimeric ADI-PEG as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising chimeric ADI-PEG and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of the chimeric ADI compositions of this disclosure in combination with one or more other therapeutic agents. Such therapeutic agents may be accepted in the art as a standard treatment for a particular disease state as described herein, such as a particular cancer or GVHD. Exemplary therapeutic agents contemplated include cytokines, growth factors, steroids, NSAIDs, DMARDs, anti-inflammatories, chemotherapeutics, radiotherapeutics, autophagy modulators, or other active and ancillary agents.

In certain embodiments, the chimeric ADI compositions disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and docetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin. Further chemotherapeutic agents include sorafenib and other protein kinase inhibitors such as afatinib, axitinib, bevacizumab, cetuximab, crizotinib, dasatinib, erlotinib, fostamatinib, gefitinib, imatinib, lapatinib, lenvatinib, mubritinib, nilotinib, panitumumab, pazopanib, pegaptanib, ranibizumab, ruxolitinib, trastuzumab, vandetanib, vemurafenib, and sunitinib; sirolimus (rapamycin), everolimus and other mTOR inhibitors. Pharmaceutically acceptable salts, acids or derivatives of any of the above are also contemplated for use herein.

In certain embodiments, the chimeric ADI compositions disclosed herein may be administered in conjunction with any number of autophagy inhibitors. In some preferred embodiments, the autophagy inhibitor is selected from the group consisting of: chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels, adenosine, N6-mercaptopurine riboside, wortmannin, and vinblastine.

In addition, antisense or siRNA that modulates expression of proteins essential for autophagy, such as for example ATG5, may also be used.

In one embodiment, the combination of chimeric ADI-PEG with one or more therapeutic agents acts additively or synergistically. In this regard, synergizing agents are described herein, which include a therapeutic agent (e.g., chemotherapeutic agent, autophagy inhibitor, mTOR inhibitor, or any other therapeutic agent used for the treatment of cancer, GVHD, or inflammatory bowel disease as described herein) that is capable of acting synergistically with chimeric ADI-PEG as provided herein, where such synergy manifests as a detectable effect that is greater (i.e., in a statistically significant manner relative to an appropriate control condition) in magnitude than the effect that can be detected when the chemotherapeutic agent is present but the ADI-PEG composition is absent, and/or when the ADI-PEG is present but the chemotherapeutic agent is absent. Methods for measuring synergy are known in the art (see e.g., Cancer Res Jan. 15, 2010 70; 440).

The compositions comprising chimeric ADI, and optionally other therapeutic agents, as described herein may be used in therapeutic methods for treating of cancer and methods for preventing metastasis of a cancer. Thus, the present invention provides for methods for treating, ameliorating the symptoms of, or inhibiting the progression of or prevention of a variety of different cancers. In another embodiment, the present disclosure provides methods for treating, ameliorating the symptoms of, or inhibiting the progression of GVHD. In particular the present disclosure provides methods for treating, ameliorating the symptoms of, or inhibiting the progression of a cancer or GVHD in a patient comprising administering to the patient a therapeutically effective amount of chimeric ADI composition as described herein, thereby treating, ameliorating the symptoms of, or inhibiting the progression of the cancer or GVHD. Thus, the chimeric ADI compositions described herein may be administered to an individual afflicted with inflammatory bowel disease (e.g., Crohn's disease; ulcerative colitis), GVHD or a cancer, including, but not limited to leukemia (e.g. acute myeloid leukemia and relapsed acute myeloid leukemia), melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multiform, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

In one embodiment, the present disclosure provides a method of treating, ameliorating the symptoms of, or inhibiting the progression of myeloid leukemia, such as, but not limited to, acute myeloid leukemia (AML), by administering a therapeutically effective amount of a chimeric ADI-PEG 20. In certain embodiments, the myeloid leukemia, such as AML, is deficient in ASS, ASL, or both. In a further embodiment, the present disclosure provides a method of treating AML comprising administering chimeric ADI-PEG 20 about once every 3 days, about once a week, about twice a week, or about once every 2 weeks. In certain embodiments, the dose of chimeric ADI-PEG 20 administered for the treatment of AML is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In particular embodiments, the dose of chimeric ADI-PEG 20 administered for the treatment of AML is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating AML, wherein the dose of chimeric ADI is doubled and may be increased to 640 IU/m2 per week or more. In one particular embodiment the chimeric ADI for the treatment of AML is modified with 3.5-6.5, or in one embodiment, 4.5-5.5 PEG molecules per chimeric ADI. In another embodiment, the present disclosure provides a method of treating AML by administering a composition comprising chimeric ADI-PEG 20 wherein the composition comprises a chimeric ADI modified with 5±1.5 PEG molecules, and in one embodiment, 5±1.5 straight chain PEG molecules, and, in certain embodiments, the composition comprises less than about 0.5% native chimeric ADI (i.e., unmodified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of sarcomas, including but not limited to metastatic sarcomas, by administering a therapeutically effective amount of a chimeric ADI-PEG 20. In certain embodiments, the sarcoma is deficient in ASS, ASL, or both. In a further embodiment, the present disclosure provides a method of treating a sarcoma comprising administering chimeric ADI-PEG 20 about once every 3 days, about once a week, about twice a week, or about once every 2 weeks. In certain embodiments, the dose of chimeric ADI-PEG 20 administered for the treatment of sarcomas is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In particular embodiments, the dose of chimeric ADI-PEG 20 administered for the treatment of sarcomas is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating sarcoma, wherein the dose of chimeric ADI is doubled and may be increased to 640 IU/m2 per week or more. In one particular embodiment the chimeric ADI for the treatment of AML is modified with 3.5-6.5, or in one embodiment, 4.5-5.5 PEG molecules per chimeric ADI. In another embodiment, the present disclosure provides a method of treating a sarcoma, including a metastatic sarcoma, by administering a composition comprising chimeric ADI-PEG 20 wherein the composition comprises an chimeric ADI modified with 5±1.5 PEG molecules, and in one embodiment, 5±1.5 straight chain PEG molecules, and, in certain embodiments, the composition comprises less than about 0.5% native chimeric ADI (i.e., unmodified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of pancreatic cancer by administering a therapeutically effective amount of chimeric ADI-PEG 20, optionally in combination with an autophagy inhibitor, such as but not limited to chloroquine, 3-methyladenine, hydroxychloroquine, bafilomycin A1, 5-amino-4-imidazole carboxamide riboside (AICAR), okadaic acid, N6-mercaptopurine riboside, wortmannin, and vinblastine.

In certain embodiments, the pancreatic cancer is deficient in ASS, ASL, or both. In a further embodiment, the present disclosure provides a method of treating pancreatic cancer comprising administering ADI-PEG 20 about once every 3 days, about once a week, about twice a week, or about once every 2 weeks; optionally in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine, or other autophagy inhibitor, may be modified as needed by a skilled clinician using dosages known in the art. As would be understood by the skilled person, the autophagy inhibitor may be administered before, at the same time as or after a composition comprising ADI-PEG 20. In certain embodiments, the dose of ADI-PEG 20 administered for the treatment of pancreatic cancer is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In particular embodiments, the dose of ADI-PEG 20 administered for the treatment of pancreatic cancer is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating pancreatic cancer, wherein the dose of chimeric ADI is doubled and may be increased to 640 IU/m2 per week or more. In one particular embodiment the chimeric ADI for the treatment of pancreatic cancer is modified with 3.5-6.5, or in one embodiment, 4.5-5.5 PEG molecules per chimeric ADI. In another embodiment, the present disclosure provides a method of treating pancreatic cancer by administering a composition comprising chimeric ADI-PEG 20, optionally in combination with chloroquine, or other appropriate autophagy inhibitor, wherein the composition comprises a chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of small cell lung cancer by administering a therapeutically effective amount of ADI-PEG 20, optionally in combination with an autophagy inhibitor. In certain embodiments, the small cell lung cancer is deficient in ASS, ASL, or both. In a further embodiment, the present disclosure provides a method of treating small cell lung cancer comprising administering chimeric ADI-PEG 20 about once every 3 days, about once a week, about twice a week, or about once every 2 weeks; optionally in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine may be modified as needed by a skilled clinician using dosages known in the art. As would be understood by the skilled person, the autophagy inhibitor may be administered before, at the same time as or after a composition comprising chimeric ADI-PEG 20. In certain embodiments, the dose of chimeric ADI-PEG 20 administered for the treatment of small cell lung cancer is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In particular embodiments, the dose of chimeric ADI-PEG 20 administered for the treatment of small cell lung cancer is between about 1 mg/m2 and about 80 mg/m2 and in other embodiments is about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating small cell lung cancer, wherein the dose of chimeric ADI is doubled and may be increased to 640 IU/m2 per week or more. In one particular embodiment the chimeric ADI for the treatment of small cell lung cancer is modified with 3.5-6.5, or in one embodiment, 4.5-5.5 PEG molecules per chimeric ADI. In another embodiment, the present disclosure provides a method of treating small cell lung cancer by administering a composition comprising chimeric ADI-PEG 20 optionally in combination with chloroquine, wherein the composition comprises an chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of sarcomas (including but not limited to, metastatic sarcomas) by administering a therapeutically effective amount of chimeric ADI-PEG 20, optionally in combination with an autophagy inhibitor. In certain embodiments, the sarcoma is deficient in ASS, ASL, or both. In a further embodiment, the present disclosure provides a method of treating sarcoma comprising administering chimeric ADI-PEG 20 about once every 3 days, about once a week, about twice a week, or about once every 2 weeks; optionally in combination with a therapeutically effective amount of an autophagy inhibitor, such as chloroquine. In this regard, a therapeutically effective dose of chloroquine may be an initial dose of about 600 mg base followed by an additional 300 mg base and a single dose of 300 mg base on each of two consecutive days. This represents a total dose of 2.5 g chloroquine phosphate or 1.5 g base in three days. In further embodiments, the dose may be about 300 mg base. The dose of chloroquine may be modified as needed by a skilled clinician using dosages known in the art. As would be understood by the skilled person, the autophagy inhibitor may be administered before, at the same time as or after a composition comprising ADI-PEG 20. In certain embodiments, the dose of ADI-PEG 20 administered for the treatment of sarcoma is between about about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In certain embodiments, the dose of ADI-PEG 20 administered for the treatment of sarcoma is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating sarcoma, wherein the dose of chimeric ADI is doubled and may be increased to 640 IU/m$^2$ per week or more. In one particular embodiment the chimeric ADI for the treatment of sarcoma is modified with 3.5-6.5, or in one embodiment, 4.5-5.5 PEG molecules per chimeric ADI. In another embodiment, the present disclosure provides a method of treating sarcoma by administering a composition comprising chimeric ADI-PEG 20, optionally in combination with chloroquine, wherein the composition comprises a chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of melanoma by administering a therapeutically effective amount of chimeric ADI-PEG 20, optionally in combination with docetaxel. In certain embodiments, the melanoma is deficient in ASS, ASL, or both. In a further embodiment, the present disclosure provides a method of treating melanoma comprising administering chimeric ADI-PEG 20 about once every 3 days, about once a week, about twice a week, or about once every 2 weeks; optionally in combination with a therapeutically effective amount of docetaxel. In this regard, a therapeutically effective dose of docetaxel may comprise 75 mg/m$^2$ or 100 mg/m$^2$ administered intravenously over between 30 minutes and 1 hour about every 3 weeks. As would be understood by the skilled clinician, the dose of docetaxel may be modified depending on disease indication and/or prior treatments, and docetaxel may be administered before, at the same time as or after a composition comprising chimeric ADI-PEG 20. In certain embodiments, the dose of chimeric ADI-PEG 20 administered for the treatment of melanoma is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. the dose of chimeric ADI-PEG 20 administered for the treatment of melanoma is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating melanoma, wherein the dose of chimeric ADI is doubled and may be increased to 640 IU/m2 per week or more. In one particular embodiment the chimeric ADI for the treatment of melanoma is modified with 3.5-6.5, or in one embodiment, 4.5-5.5, PEG molecules per chimeric ADI. In another embodiment, the present disclosure provides a method of treating melanoma by a composition comprising chimeric ADI-PEG 20, optionally in combination with docetaxel, wherein the composition comprises an chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of melanoma by administering a therapeutically effective amount of chimeric ADI-PEG 20, optionally in combination with cisplatin. In certain embodiments, the melanoma is deficient in ASS, ASL, or both. In a further embodiment, the present disclosure provides a method of treating melanoma comprising administering chimeric ADI-PEG 20 about once every 3 days, about once a week, about twice a week, or about once every 2 weeks; optionally in combination with a therapeutically effective amount of cisplatin. In this regard, a therapeutically effective dose of cisplatin may comprise administration either once per cycle (every 3-4 weeks) at 50-100 mg/m$^2$, or daily for 5 days for a total of 100 mg/m$^2$ per cycle. As would be understood by the skilled clinician, the dose of cisplatin may be modified depending on disease indication, individual patient, and/or prior treatments, and cisplatin may be administered before, at the same time as or after a composition comprising chimeric ADI-PEG 20. In certain embodiments, the dose of chimeric ADI-PEG 20 administered for the treatment of melanoma is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In certain embodiments, the dose of chimeric ADI-PEG 20 administered for the treatment of melanoma is between about 1 mg/m2 and about 80 mg/m2 and in other embodiments is about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating melanoma, wherein the dose of chimeric ADI is doubled and may be increased to 640 IU/m2 per week or more. In one particular embodiment the chimeric ADI for the treatment of melanoma is modified with 3.5-6.5, or in one embodiment, 4.5-5.5, PEG molecules per chimeric ADI. In another embodiment, the present disclosure provides a method of treating melanoma by administering a composition comprising chimeric ADI-PEG 20, optionally in combination with cisplatin, wherein the composition comprises a chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

In one embodiment, the present disclosure provides a method of treating, ameliorating the symptoms of, or inhibiting the progression of renal cell carcinoma by administering a therapeutically effective amount of chimeric ADI-PEG 20, optionally in combination with an mTOR inhibitor, such as but not limited to rapamycin, temsirolimus, everolimus, and ridaforolimus. In certain embodiments, the renal cell carcinoma is deficient in ASS, ASL, or both. In a further embodiment, the present disclosure provides a method of treating renal cell carcinoma comprising administering chimeric ADI-PEG 20 about once every 3 days, about once a week, about twice a week, or about once every 2 weeks; optionally in combination with a therapeutically effective amount of an mTOR inhibitor, such as rapamycin. The dose of rapamycin, or other mTOR inhibitor, may be determined as needed by a skilled clinician using dosages known in the art. As would be understood by the skilled person, the mTOR inhibitor may be administered before, at the same time as or after a composition comprising chimeric ADI-PEG 20. In certain embodiments, the dose of chimeric ADI-PEG 20 administered for the treatment of renal cell carcinoma is between about 50 IU/m$^2$ and about 8,000 IU/m$^2$, and in other embodiments is about 50 IU/m2, about 100 IU/m$^2$, 150 IU/m$^2$, 200 IU/m$^2$, 250 IU/m$^2$, 300 IU/m$^2$, 350 IU/m$^2$, 400 IU/m$^2$, 450 IU/m$^2$, 500 IU/m$^2$, 550 IU/m$^2$, 600 IU/m$^2$, 650 IU/m$^2$, 700 IU/m$^2$, 750 IU/m$^2$, 800 IU/m$^2$, about 900 IU/m$^2$, about 1,000 IU/m$^2$, 1,500 IU/m$^2$ about 2,000 IU/m$^2$, about 2,500 IU/m$^2$, about 3,000 IU/m$^2$, 3,500 IU/m$^2$, 4,000 IU/m$^2$, 4,500 IU/m$^2$, 5,000 IU/m$^2$, 5,500 IU/m$^2$, 6,000 IU/m$^2$, 6,500 IU/m$^2$, 7,000 IU/m$^2$, 7,500 IU/m$^2$, or about 8,000 IU/m$^2$. In certain embodiments, the dose of chimeric ADI-PEG 20 administered for the treatment of melanoma is between about about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, or about 80 mg/m$^2$. In certain embodiments, the present disclosure provides a method of treating renal cell carcinoma, wherein the dose of chimeric ADI is doubled and may be increased to 640 IU/m$^2$ per week or more. In one particular embodiment the chimeric ADI for the treatment of renal cell carcinoma is modified with 3.5-6.5, or in one embodiment, 4.5-5.5 PEG molecules per chimeric ADI. In another embodiment, the present disclosure provides a method of treating renal cell carcinoma by administering a composition comprising chimeric ADI-PEG 20, optionally in combination with rapamycin, or other appropriate mTOR inhibitor, wherein the composition comprises a chimeric ADI modified with 5±1.5 PEG molecules, and in one embodiment, 5±1.5 straight chain PEG molecules, and, in certain embodiments, the composition comprises less than about 0.5% native chimeric ADI (i.e., not modified with PEG) and/or less than about 5% free PEG. In a further embodiment, the composition comprises a histidine-HCL buffer.

The present disclosure also provides methods of treating, ameliorating the symptoms of, or inhibiting the progression of an inflammatory disorder in a patient comprising administering to the patient a composition comprising chimeric ADI (e.g., chimeric ADI-PEG, in particular chimeric ADI-PEG 20), as described herein, alone or in combination with one or more other therapeutic agents. In one embodiment, the present disclosure also provides methods of treating, ameliorating the symptoms of, or inhibiting the progression of an inflammatory bowel disease in a patient comprising administering to the patient a composition comprising chimeric ADI (e.g., chimeric ADI-PEG, in particular chimeric ADI-PEG 20), as described herein, alone or in combination with one or more other therapeutic agents. In this regard, the present disclosure provides methods of treating, ameliorating the symptoms of, or inhibiting the progression of Crohn's disease or ulcerative colitis in a patient comprising administering to the patient a composition comprising chimeric ADI (e.g., chimeric ADI-PEG, in particular chimeric ADI-PEG 20), as described herein, alone or in combination with one or more other therapeutic agents.

In another embodiment, the present disclosure provides a method of treating, ameliorating the symptoms of, or inhibiting the progression of a cancer in a patient comprising administering to the patient a composition comprising chimeric ADI, and optionally one or more other therapeutic agents, as described herein, wherein the cancer is deficient in ASS, ASL, or both. In this regard, ASS or ASL deficiency may be a reduction in expression as measured by mRNA expression or protein expression, or may be a reduction in protein activity, and generally comprises a statistically significant reduction in expression or activity as determined by the skilled person. Reduced ASS or ASL expression or activity may be a reduction in expression or activity of about 5%, 10%, 15%, 20%, 25%, 30%, 35%, 40%, 45%, 50%, 55%, 60%, 65%, 70%, or more, as compared to expression or activity in an appropriate control sample known to be cancer free. In certain embodiments, ASS or ASL expression or activity is reduced by at least twofold as compared to expression or activity in a non-cancer control sample.

In certain embodiments, the reduced expression or activity of ASS or ASL results from methylation of the ASS or ASL promoter. In another embodiment the reduction in expression or activity of ASS or ASL results from a DNA mutation (e.g., one or more point mutations, small deletions, insertions, and the like) or a chromosomal abnormality resulting in deletion of the gene. In one embodiment, the cancer is ASS or ASL negative, meaning no expression or activity is observed.

Reduction in ASS or ASL expression or activity may be measured using any methods known in the art, such as but not limited to, quantitative PCR, immunohistochemistry, enzyme activity assays (e.g., assay to measure conversion of citrulline into argininosuccinate or conversion of argininosuccinate into arginine and fumarate), and the like.

Thus, the present invention provides methods for treating, ameliorating the symptoms of, or inhibiting the progression of a cancer in a patient comprising administering to the patient a composition comprising chimeric ADI as described herein, wherein the cancer exhibits reduced expression or activity of ASS or ASL, or both, wherein the cancer includes, but is not limited to leukemia (e.g. acute myeloid leukemia and relapsed acute myeloid leukemia), melanoma, sarcomas (including, but not limited to, metastatic sarcomas, uterine leiomyosarcoma), pancreatic cancer, prostate cancer (such as, but not limited to, hormone refractory prostate cancer), mesothelioma, lymphatic leukemia, chronic myelogenous leukemia, lymphoma, small cell lung cancer, breast cancer, ovarian cancer, colorectal cancer, gastric cancer (including, but not limited to, gastric adenocarcinoma), glioma, glioblastoma multi-form, retinoblastoma, neuroblastoma, non-small cell lung cancer (NSCLC), kidney cancer (including but not limited to renal cell carcinoma), bladder cancer, uterine cancer, esophageal cancer, brain cancer, head and neck cancers (including, but not limited to, squamous cell carcinoma of the head and neck; cancer of the tongue), cervical cancer, testicular cancer, gallbladder, cholangiocarcinoma, and stomach cancer.

Various studies in the literature have shown that ASS is deficient in the following tumors:

TABLE 1

| ASS-Deficient Tumors | |
|---|---|
| Tumor Type | ASS Deficiency (%) |
| Prostate | 88/88 (100%) |
| Renal | 98/98 (100%) |
|  | 41/45 (91%) |
|  | 31/31 (100%) |
| Lymphoma | 511/532 (96%) |
| Sarcoma | 619/701 (88%) |
| Pancreatic | 41/47 (87%) |
| Acute Myelogenous Leukemia | 46/53 (87%) |
| Small Cell Lung | 7/16 (44%) |
| HCC | 33/44 (75%) |
|  | 20/20 (100%) |
| Melanoma | 119/119 (100%) |
|  | 24/29 (83%) |
|  | 17/27 (63%) |
|  | 20/20 (100%) |
| Bladder | 31/48 (65%) |
|  | 133/242 (55%) |
| Mesothelioma | 52/82 (63%) |
| Gastric | 68/121 (56%) |
| Breast | 46/111 (41%) |
| Non-Small Cell Lung | 28/90 (31%) |
| Glioblastoma | 39/55 (71%) |
| Colorectal | 31 (3%) |
| Ovarian | 23/54 (43%) at diagnosis |
|  | 25/34 (74%) at relapse |

Accordingly, treatment of these ASS-deficient cancers is specifically contemplated herein, with chimeric ADI-PEG alone or in combination with other treatments.

The present invention further provides methods for treating, ameliorating the symptoms of, or inhibiting the progression of cancer in a patient comprising administering to the patient a composition comprising chimeric ADI as described herein (e.g., chimeric ADI-PEG and in particular chimeric ADI-PEG 20), in combination with an autophagy inhibitor. In one embodiment, the present invention provides methods for treating cancer in a patient comprising administering to the patient a therapeutically effective amount of a composition comprising chimeric ADI as described herein in combination with autophagy inhibitor wherein the cancer is pancreatic cancer or small cell lung cancer.

In certain embodiments, the present invention provides methods of treatment where administration of the compositions comprising chimeric ADI described herein depletes arginine in the plasma for at least one month, 2 months, 3 months, 4 months, 5 months, 6 months or longer.

EXAMPLES

Example 1

Chimeric ADI Enzymes are Active and Less Cross-Reactive with Patient Anti-ADI-Peg 20 Antibodies This Example describes the generation of artificially engineered chimeric ADI enzymes composed of (1) protein with arginine deiminase enzymatic activity, (2) reduced cross reactivity with anti-ADI-PEG 20 antibodies, (3) reduced number of lysine residues, and/or (4) PEG conjugation with chemically stable linkers.

ADI Preparation.

Recombinant chimeric ADI enzymes were cloned, expressed, and purified for testing according to standard protocols, as described, for example, in Gallego et al., PLOS One, 7(10):e47886, 2012; Monstadt and Holldorf, Biochem. J. 273:739-745, 1990; Joo Noh et al., Molecules and Cells. 13:137-143, 2002; and Sugimura et al., Infection and Immunity. 58:2510-2515, 1990. See Table A1 for the amino acid sequences of the chimeric ADI enzymes.

Human Anti-ADI-PEG20 Antibody Purification.

Anti-ADI-PEG20 antibody was purified from plasma samples of patients who had received ADI-PEG20 during a clinical study. A total of 60 ml of plasma was pooled from 8 different patients that had reached high titer (titer >/=4) against ADI-PEG20 as determined by an ELISA assay. A two-step purification was used, a Protein "A" chromatography (GE Healthcare) followed by an ADI affinity chromatography. ~20 mg of purified antibody was obtained and stored at −80° C. in aliquots until needed.

ADI Enzyme Assays.

Arginine deiminase (ADI) catalyzes the conversion of L-arginine to L-citrulline and ammonia. The amount of L-citrulline can be detected by a colorimetric endpoint assay (see, for example, Knipp and Vasak, Analytical Biochem. 286:257-264, 2000) and compared to a standard curve of known amounts of L-citrulline in order to calculate the specific activity of ADI expressed as IU/mg of protein. One IU of enzyme activity is defined as the amount of enzyme that produces 1 µmol of citrulline per minute at the pH and temperature being tested. Standard assay conditions were performed at 37° C. in Physiological HEPES Buffer (PHB) 50 mM HEPES, 160 mM NaCl pH 7.4 (Lang and Zander, Clin Chem Lab Med. 37:563-571, 1999) plus 0.1% BSA. All samples and standards were run in duplicate or triplicate where conditions permitted.

Km and Kcat values were determined by using a variation of the activity assay described above. As with the activity assay, all reactions were run at 37° C. in PHB plus 0.1% BSA. Enzyme concentration, reaction time, and substrate concentration range were adjusted for each of the ADI or ADIr constructs to account for their differences in activity. In general, 2 nM enzyme, 5 minute reaction time, and a 0-160 µM arginine was used as starting conditions. When optimizing the conditions, particular attention was paid towards the amount of substrate consumed as a percentage of total substrate added to the reaction. The lower limit of detection is 1 µM of citrulline with the lower limit of quantitation being 2 µM. A citrulline standard curve was run on every plate and used to quantify the citrulline produced by the enzymatic reaction.

Calculations.

The citrulline concentration (µM) produced in each reaction well was calculated and averaged using the citrulline standard curve. The velocity of each reaction was then calculated in µM/min/50 nM ADI. Specific activity (IU/mg or µmols product/min/mg ADI) was calculated by multiplying this value by the "IU" factor (IU factor was calculated from the molecular weight of the ADI and the reaction volume).

Arginine Deiminase Enzymatic Activity.

The results of the ADI enzyme assays are shown in Table E1.

TABLE E1

Chimeric ADI Enzymes.

| Name | SEQ ID NO: | Catalytic Domain | α-Helical Domain | Specific Activity |
|---|---|---|---|---|
| M. hominis | 1 | M. hominis | M. hominis | +++ |
| DS1 | 4 | M. arginini (1-74, 153-410) | M. arthritidis (75-152) | +++ |
| DS2 | 5 | M. arginini (1-74, 153-410) | M. hominis (75-151) | +++ |
| DS3 | 6 | M. arthritidis (1-74, 153-410) | M. arginini (75-152) | +++ |
| DS4 | 7 | M. arthritidis (1-74, 153-410) | M. hominis (75-151) | +++ |
| C2DS1 | 22 | M. arginini (1-74, 153-410) | M. alligatoris (71-148) | + |
| C2DS3 | 23 | M. arginini (1-74, 153-410) | M. arthritidis (75-152) | +++ |
| C2DS4 | 24 | M. arginini (1-74, 153-410) | M. columbinum (68-147) | +++ |
| C2DS5 | 25 | M. arginini (1-74, 153-410) | M. gateae (75-152) | +++ |
| C2DS6 | 26 | M. arginini (1-74, 153-410) | M. phocicerebrale (75-152) | +++ |
| C2DS7 | 27 | M. arginini (1-74, 153-410) | M. phocidae (75-152) | +++ |
| C4DS1 | 28 | M. columbinum (1-67, 148-401) | M. alligatoris (71-148) | n.d. |
| C4DS2 | 29 | M. columbinum (1-67, 148-401) | M. arginini (75-152) | n.d. |
| C4DS3 | 30 | M. columbinum (1-67, 148-401) | M. arthritidis (75-152) | +++ |
| C4DS5 | 31 | M. columbinum (1-67, 148-401) | M. gateae (75-152) | +++ |
| C4DS6 | 32 | M. columbinum (1-67, 148-401) | M. phocicerebrale (75-152) | ++ |
| C4DS7 | 33 | M. columbinum (1-67, 148-401) | M. phocidae (75-152) | n.d. |
| C4DS8 | 34 | M. columbinum (1-67, 148-401) | M. gallinarum (68-147) | ++++ |
| C4DS9 | 35 | M. columbinum (1-67, 148-401) | M. iners (68-147) | +++++ |
| C5DS1 | 36 | M. gateae (1-74, 153-410) | M. alligatoris (71-148) | +++ |
| C5DS2 | 37 | M. gateae (1-74, 153-410) | M. arginini (75-152) | ++++ |
| C5DS3 | 38 | M. gateae (1-74, 153-410) | M. arthritidis (75-152) | +++ |
| C5DS4 | 39 | M. gateae (1-74, 153-410) | M. columbinum (68-147) | +++ |
| C5DS6 | 40 | M. gateae (1-74, 153-410) | M. phocicerebrale (75-152) | +++ |
| C5DS7 | 41 | M. gateae (1-74, 153-410) | M. phocidae (75-152) | +++ |
| C6DS1 | 42 | M. phocicerebrale (1-74, 153-410) | M. alligatoris (71-148) | n.d. |
| C6DS2 | 43 | M. phocicerebrale (1-74, 153-410) | M. arginini (75-152) | ++++ |
| C6DS3 | 44 | M. phocicerebrale (1-74, 153-410) | M. arthritidis (75-152) | + |
| C6DS4 | 45 | M. phocicerebrale (1-74, 153-410) | M. columbinum (68-147) | n.d. |
| C6DS5 | 46 | M. phocicerebrale (1-74, 153-410) | M. gateae (75-152) | +++ |

TABLE E1-continued

Chimeric ADI Enzymes.

| Name | SEQ ID NO: | Catalytic Domain | α-Helical Domain | Specific Activity |
|---|---|---|---|---|
| C6DS7 | 47 | M. phocicerebrale (1-74, 153-410) | M. phocidae (75-152) | +++ |
| C7DS1 | 48 | M. phocidae (1-74, 153-410) | M. alligatoris (71-148) | n.d. |
| C7DS2 | 49 | M. phocidae (1-74, 153-410) | M. arginini (75-152) | ++++ |
| C7DS3 | 50 | M. phocidae (1-74, 153-410) | M. arthritidis (75-152) | +++ |
| C7DS4 | 51 | M. phocidae (1-74, 153-410) | M. columbinum (68-147) | +++ |
| C7DS5 | 52 | M. phocidae (1-74, 153-410) | M. gateae (75-152) | +++ |
| C7DS6 | 53 | M. phocidae (1-74, 153-410) | M. phocicerebrale (75-152) | ++++ |
| C8DS3 | 54 | M. gallinarum (1-67, 148-401) | M. arthritidis (75-152) | n.d. |
| C8DS4 | 55 | M. gallinarum (1-67, 148-401) | M. columbinum (68-147) | +++++ |
| C8DS9 | 56 | M. gallinarum (1-67, 148-401) | M. iners (68-147) | +++++ |
| C9DS3 | 57 | M. iners (1-67, 148-401) | M. arthritidis (75-152) | n.d. |
| C9DS4 | 58 | M. iners (1-67, 148-401) | M. columbinum (68-147) | +++++ |
| C9DS8 | 59 | M. iners (1-67, 148-401) | M. gallinarum (68-147) | ++++ |

Chimeric molecules were engineered from M. arginini (SEQ ID NO: 2), M. arthritidis (SEQ ID NO: 3), and M. hominis (Phoenix sequence set forth in SEQ ID NO: 14, with modifications). The parenthetical numbers specify the amino acid residues from the natural enzymes, used to form the domains. A C-terminal tryptophan was added to the published M. arthritidis sequence and mutation C251S was made for M. arginini and M. arthritidis. The ADI specific activity (IU/mg) of these non-pegylated enzymes is shown relative to ADI-PEG 20 (+++).

The results in Table E1 show that the engineered chimeric ADI enzymes described herein have efficient catalytic activity. The catalytic parameters Km and kcat for these enzymes is sufficient to remove arginine and maintain low arginine concentrations in the blood. These parameters are preferably less than 20 μM and greater than 1 sec$^{-1}$, respectively. The pH optimum is around 7.4 so as to maintain efficient catalytic activity in blood. The enzyme stability, as well as that of the covalently linked PEG, is such that it should be maintained during long-term storage and patient treatment at 37° C.

Reduced Cross Reactivity with Anti-ADI-PEG 20 Antibodies.

ADI is composed of two domains, a catalytic domain and an α-helical domain. The present invention is directed in part to engineered, artificial, chimeric, recombinant enzymes with ADI activity. Each is composed of two domains, where each domain is selected from a number of possible species. Domain boundaries are determined by examination of ADI X-ray crystal structures from M. hominis and M. arginini, and extending this to other Mycoplasma ADI enzymes by homology.

The use of domains from different species of ADI enzymes can maintain the catalytic activity while changing a number of surface residues. Some of these surface residues form epitopes for anti-ADI-PEG 20 antibodies developed during a patient's treatment with ADI-PEG 20. Their replacement can reduce the antigenicity with respect to anti-ADI-PEG 20 antibodies, therefore reducing anti-ADI-PEG 20 antibody neutralization and clearance of the modified drug. This is shown in Table E2, where two preparations of anti-ADI-PEG 20 antibodies showed less binding to the DS1, DS2, DS3, and DS4 antigens, compared to M. hominis ADI. This can be attributed to residue changes on the surface of these antigens that alter the epitopes and disrupt antibody-antigen binding interactions.

TABLE E2

Reduction of Anti-ADI-PEG 20 Antibody Binding to ADI Antigens Compared to ADI-PEG 20

| | | Antigens | | | |
|---|---|---|---|---|---|
| Antibody | Conc μg/mL | DS1 1 μg/mL | DS2 1 μg/mL | DS3 1 μg/mL | DS4 1 μg/mL |
| Human anti-ADI-PEG 20 IgG (titer 3) | 10.0 | Yes | No | Yes | No |
| Human anti-ADI-PEG 20 IgG (titer 3) | 25.0 | Yes | No | Yes | No |
| Human anti-ADI-PEG 20 IgG (titer 3) | 50.0 | Yes | Yes | Yes | Yes |
| Human anti-ADI-PEG 20 IgG (titer 4) | 0.5 | Yes | No | Yes | No |
| Human anti-ADI-PEG 20 IgG (titer 4) | 1.0 | Yes | No | Yes | No |
| Human anti-ADI-PEG 20 IgG (titer 4) | 5.0 | Yes | Yes | Yes | Yes |

Surface Lysine Residue Content Reduction.

The M. arginini (catalytic domain)—M. arthritidis (a-helical domain) chimeras were further modified by replacing surface lysine residues with amino acid residues other than lysine and monitoring ADI activity. Four mutants were made (Table E3) and their ADI activity was determined.

TABLE E3

ADI Lysine Replacement Mutants for DS1 (M. arginini (catalytic): M. arthritidis (α-helical))

Lysine residues

| | 7 | 9 | 56 | 59 | 86 | 88 | 91 | 93 | 96 | 115 | 116 | 133 | 141 | 170 | 178 | 194 | 225 | 226 | 328 | 330 | 406 |
|---|---|---|---|---|---|---|---|---|---|---|---|---|---|---|---|---|---|---|---|---|---|
| DS1 | K | K | K | K | K | K | K | K | K | K | K | K | K | K | K | K | K | K | K | K | K |
| DS1-1 | H | K | K | K | K | R | K | K | K | K | R | K | K | R | K | K | K | K | K | T | K |
| DS1-2 | H | N | K | Q | K | R | K | K | R | N | R | K | I | R | K | K | K | K | K | T | K |
| DS1-3 | H | N | K | Q | R | R | Q | N | K | R | N | R | G | I | R | K | R | K | K | T | K |
| DS1-4 | H | N | T | Q | R | R | Q | N | L | R | N | R | G | I | R | R | R | R | R | T | R |

DS1 Lysine replacement mutants, made in groups of 5 or 6.

Table E4 shows ADI activity of the DS1 (M. arginini-M. arthritidis) enzyme and 4 lysine replacement mutants. Lysine reduction was undertaken to reduce the number of potential pegylation sites.

TABLE E4

ADI Enzyme Activity
ADI Enzyme Yield and Activity

| Enzyme | Number of Lys Residues | ADI Specific Activity |
|---|---|---|
| DS1 | 29 | +++ |
| DS1-1 | 24 | +++ |
| DS1-2 | 19 | +++ |
| DS1-3 | 14 | +++ |
| DS1-4 | 8 | +++ |

With around 30 potential pegylation sites, the PEG occupancy is generally small at each site. Reducing the number of potential pegylation sites will result in higher PEG occupancies and more complete shielding at each remaining site. This is expected to increase proteolytic protection and reduce immune cross reactivity to affinity matured anti-ADI-PEG 20 antibodies from previous treatments. It will also produce a more uniform drug.

In summary, the present Examples describes engineered ADI enzymes with excellent ADI activity, with anti-ADI-PEG 20 antibody epitopes removed to reduce antibody neutralization and clearance, and with protection from proteolysis and renal clearance by pegylation.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A recombinant chimeric arginine deiminase (ADI) comprising a catalytic domain of an ADI protein derived from a first microorganism and an α-helical domain of an ADI protein derived from a second microorganism, wherein the first microorganism differs from the second microorganism, wherein the recombinant chimeric ADI comprises that amino acid sequence set forth in any one of SEQ ID NOs: 55, 56, 35, 58, 34, or 59 or a variant having at least 98% identity to any one of SEQ ID NOs: 55, 56, 35, 58, 34, or 59, with or without the hexahistidine tag.

2. The recombinant chimeric ADI of claim 1, wherein the recombinant chimeric ADI comprises the amino acid sequence set forth in any one of SEQ ID NOs: 55, 56, 35, 58, 34, or 59, with or without the hexahistidine tag.

3. The recombinant chimeric ADI of claim 1, wherein the recombinant chimeric ADI has been modified to remove at least one pegylation site.

4. The recombinant chimeric ADI of claim 1, wherein at least one lysine residue has been modified by an amino acid substitution.

5. The recombinant chimeric ADI of claim 1 covalently bonded via a biocompatible linker to polyethylene glycol (PEG).

6. The recombinant chimeric ADI of claim 5, wherein the arginine deiminase is covalently bonded to more than one polyethylene glycol molecule.

7. The recombinant chimeric ADI of claim 5, wherein the arginine deiminase is covalently bonded to about 1 to about 10 polyethylene glycol molecules.

8. The recombinant chimeric ADI of claim 5, wherein the arginine deiminase is covalently bonded to 5±3 PEG molecules.

9. The recombinant chimeric ADI of claim 5, wherein the PEG molecules are straight chain or branch chain PEG molecules.

10. The recombinant chimeric ADI of claim 5, wherein the polyethylene glycol has a total weight average molecular weight of from about 1,000 to about 40,000.

11. The recombinant chimeric ADI of claim 4, wherein the polyethylene glycol has a total weight average molecular weight of from about 10,000 to about 30,000.

12. The recombinant chimeric ADI of claim 5, wherein the biocompatible linker comprises a succinyl group, an amide group, an imide group, a carbamate group, an ester group, an epoxy group, a carboxyl group, a hydroxyl group, a carbohydrate, a tyrosine group, a cysteine group, a histidine group, a methylene group, or a combination thereof.

13. The recombinant chimeric ADI of claim 12, wherein the source of the succinyl group is succinimidyl succinate.

14. A polynucleotide encoding the recombinant chimeric ADI of claim 1.

15. A vector comprising the polynucleotide of claim 14.

16. An isolated host cell comprising the vector of claim 15.

17. A composition comprising the recombinant chimeric ADI of claim 1 and a physiologically acceptable carrier.

18. The composition of claim 17, further comprising an autophagy modulator.

19. The composition of claim 18, wherein the autophagy modulator is selected from the group consisting of chloroquine, 3-methyladenine, hydroxychloroquine, bafilomycin A1, 5-amino-4-imidazole carboxamide riboside (AICAR), okadaic acid, N6-mercaptopurine riboside, vinblastine, wortmannin, rapamycin, everolimus, metformin, perifosine, resveratrol, and tamoxifen.

20. The composition of claim 17, further comprising a chemotherapeutic agent.

21. The composition of claim 20 wherein the chemotherapeutic agent is selected from the group consisting of docetaxel, carboplatin, cyclophosphamide, gemcitabine, cisplatin, sorafenib, sunitinib and everolimus.

22. A method of treating, ameliorating the symptoms of, or inhibiting the progression of a cancer comprising administering to a patient in need thereof a therapeutically effective amount of the composition of claim 17, thereby treating, ameliorating the symptoms of, or inhibiting the progression of the cancer.

23. The method of claim 22 wherein the cancer is selected from the group consisting of melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

* * * * *

SEQUENCE LISTING

```
<160> NUMBER OF SEQ ID NOS: 59

<210> SEQ ID NO 1
<211> LENGTH: 409
<212> TYPE: PRT
<213> ORGANISM: Mycoplasma hominis

<400> SEQUENCE: 1

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Pro Ile Glu Gly Gly Asp Val Phe Ile Tyr Asn Asn Glu Thr Leu
    210                 215                 220
```

```
Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
            245                 250                 255

Ala Ile Asn Val Pro Lys Trp Thr Asn Leu Met His Leu Asp Thr Trp
                260                 265                 270

Leu Thr Met Leu Asp Lys Asn Lys Phe Leu Tyr Ser Pro Ile Ala Asn
            275                 280                 285

Asp Val Phe Lys Phe Trp Asp Tyr Asp Leu Val Asn Gly Gly Ala Glu
                290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
            325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 2
<211> LENGTH: 410
<212> TYPE: PRT
<213> ORGANISM: Mycoplasma arginini

<400> SEQUENCE: 2

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
```

```
                180             185             190
Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
            245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 3
<211> LENGTH: 410
<212> TYPE: PRT
<213> ORGANISM: Mycoplasma arthritidis

<400> SEQUENCE: 3

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Glu Phe Val Ala Glu
        50                  55                  60

Leu Lys Lys Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
130                 135                 140
```

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
        180                 185                 190

Asn His Pro Lys Leu Val Asn Thr Pro Trp Tyr Tyr Asp Pro Ala Glu
    195                 200                 205

Gly Leu Thr Ile Glu Gly Gly Asp Val Phe Ile Tyr Asn Asn Asp Thr
210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
        355                 360                 365

Lys Thr Asn Ala Ala Leu Glu Ala Ala Gly Ile Thr Val Leu Pro Phe
    370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 4
<211> LENGTH: 410
<212> TYPE: PRT
<213> ORGANISM: Artificial Sequence
<220> FEATURE:
<223> OTHER INFORMATION: DS1 recombinant chimeric ADI protein

<400> SEQUENCE: 4

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
                100                 105                 110

Thr Val Lys Lys Phe Leu Gln Ser Gln Lys Ser Thr Arg Ser Leu Val
            115                 120                 125

Glu Tyr Met Ile Ala Gly Ile Thr Lys His Asp Leu Lys Ile Glu Ser
        130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
            245                 250                 255

Val Ala Ile Asn Val Pro Lys Trp Thr Asn Leu Met His Leu Asp Thr
        260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
        290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ala Gly Glu Gly
            325                 330                 335

Ala Ser Gln Met Glu Ile Glu Arg Glu Thr His Phe Asp Gly Thr Asn
        340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
        370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 5
<211> LENGTH: 409
<212> TYPE: PRT
<213> ORGANISM: Artificial Sequence
<220> FEATURE:
<223> OTHER INFORMATION: DS2 recombinant chimeric ADI protein

<400> SEQUENCE: 5

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

```
Leu Glu Ser His Asp Ala Arg Lys Glu His Lys Gln Phe Val Ala Glu
 50                  55                  60
Leu Lys Ala Asn Asp Ile Asn Val Val Glu Leu Thr Asp Leu Val Ala
 65                  70                  75                  80
Glu Thr Tyr Asp Leu Ala Ser Arg Ala Ala Lys Glu Glu Phe Ile Glu
                 85                  90                  95
Thr Phe Leu Glu Glu Thr Val Pro Val Leu Thr Glu Ala Asn Arg Glu
            100                 105                 110
Ala Val Arg Ala Phe Leu Leu Ser Lys Pro Thr His Glu Met Val Glu
        115                 120                 125
Phe Met Met Ser Gly Ile Thr Lys Tyr Glu Leu Gly Val Glu Ser Glu
130                 135                 140
Asn Glu Leu Ile Val Asp Pro Met Pro Asn Leu Tyr Phe Thr Arg Asp
145                 150                 155                 160
Pro Phe Ala Ser Val Gly Asn Gly Val Thr Ile His Tyr Met Arg Tyr
                165                 170                 175
Lys Val Arg Gln Arg Glu Thr Leu Phe Ser Arg Phe Val Phe Ser Asn
            180                 185                 190
His Pro Lys Leu Ile Asn Thr Pro Trp Tyr Tyr Asp Pro Ser Leu Lys
        195                 200                 205
Leu Ser Ile Glu Gly Gly Asp Val Phe Ile Tyr Asn Asn Asp Thr Leu
210                 215                 220
Val Val Gly Val Ser Glu Arg Thr Asp Leu Gln Thr Val Thr Leu Leu
225                 230                 235                 240
Ala Lys Asn Ile Val Ala Asn Lys Glu Ser Glu Phe Lys Arg Ile Val
                245                 250                 255
Ala Ile Asn Val Pro Lys Trp Thr Asn Leu Met His Leu Asp Thr Trp
            260                 265                 270
Leu Thr Met Leu Asp Lys Asp Lys Phe Leu Tyr Ser Pro Ile Ala Asn
        275                 280                 285
Asp Val Phe Lys Phe Trp Asp Tyr Asp Leu Val Asn Gly Gly Ala Glu
290                 295                 300
Pro Gln Pro Val Glu Asn Gly Leu Pro Leu Glu Gly Leu Leu Gln Ser
305                 310                 315                 320
Ile Ile Asn Lys Lys Pro Val Leu Ile Pro Ile Ala Gly Glu Gly Ala
                325                 330                 335
Ser Gln Met Glu Ile Glu Arg Glu Thr His Phe Asp Gly Thr Asn Tyr
            340                 345                 350
Leu Ala Ile Arg Pro Gly Val Val Ile Gly Tyr Ser Arg Asn Glu Lys
        355                 360                 365
Thr Asn Ala Ala Leu Glu Ala Ala Gly Ile Lys Val Leu Pro Phe His
370                 375                 380
Gly Asn Gln Leu Ser Leu Gly Met Gly Asn Ala Arg Cys Met Ser Met
385                 390                 395                 400
Pro Leu Ser Arg Lys Asp Val Lys Trp
                405

<210> SEQ ID NO 6
<211> LENGTH: 410
<212> TYPE: PRT
<213> ORGANISM: Artificial Sequence
<220> FEATURE:
<223> OTHER INFORMATION: DS3 recombinant chimeric ADI protein

<400> SEQUENCE: 6
```

-continued

```
Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Glu Phe Val Ala Glu
            50                  55                  60

Leu Lys Lys Arg Gly Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
            115                 120                 125

Glu Ile Met Met Ala Gly Ile Thr Lys Tyr Asp Leu Gly Ile Glu Ala
            130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ala Glu
            195                 200                 205

Gly Leu Thr Ile Glu Gly Gly Asp Val Phe Ile Tyr Asn Asn Asp Thr
            210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Asp
            290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
            355                 360                 365

Lys Thr Asn Ala Ala Leu Glu Ala Ala Gly Ile Thr Val Leu Pro Phe
            370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```

-continued

```
<210> SEQ ID NO 7
<211> LENGTH: 409
<212> TYPE: PRT
<213> ORGANISM: Artificial Sequence
<220> FEATURE:
<223> OTHER INFORMATION: DS4 recombinant chimeric ADI protein

<400> SEQUENCE: 7

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Ala Glu
    50                  55                  60

Leu Lys Lys Arg Gly Ile Asn Val Val Glu Leu Thr Asp Leu Val Ala
65                  70                  75                  80

Glu Thr Tyr Asp Leu Ala Ser Arg Ala Ala Lys Glu Glu Phe Ile Glu
                85                  90                  95

Thr Phe Leu Glu Glu Thr Val Pro Val Leu Thr Glu Ala Asn Arg Glu
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Tyr Met Arg Tyr
                165                 170                 175

Lys Val Arg Gln Arg Glu Thr Leu Phe Ser Arg Phe Val Phe Ser Asn
            180                 185                 190

His Pro Lys Leu Val Asn Thr Pro Trp Tyr Tyr Asp Pro Ala Glu Gly
        195                 200                 205

Leu Thr Ile Glu Gly Gly Asp Val Phe Ile Tyr Asn Asn Asp Thr Leu
    210                 215                 220

Val Val Gly Val Ser Glu Arg Thr Asp Leu Gln Thr Ile Thr Leu Leu
225                 230                 235                 240

Ala Lys Asn Ile Lys Ala Asn Lys Glu Ser Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asp Lys Phe Leu Tyr Ser Pro Ile Ala Asn
        275                 280                 285

Asp Val Phe Lys Phe Trp Asp Tyr Asp Leu Val Asn Gly Gly Asp Ala
    290                 295                 300

Pro Gln Pro Val Asp Asn Gly Leu Pro Leu Glu Asp Leu Leu Lys Ser
305                 310                 315                 320

Ile Ile Gly Lys Lys Pro Thr Leu Ile Pro Ile Ala Gly Ala Gly Ala
                325                 330                 335

Ser Gln Ile Asp Ile Glu Arg Glu Thr His Phe Asp Gly Thr Asn Tyr
            340                 345                 350

Leu Ala Val Ala Pro Gly Ile Val Ile Gly Tyr Ala Arg Asn Glu Lys
        355                 360                 365

Thr Asn Ala Ala Leu Glu Ala Ala Gly Ile Thr Val Leu Pro Phe Arg
```

```
              370                 375                 380
Gly Asn Gln Leu Ser Leu Gly Met Gly Asn Ala Arg Cys Met Ser Met
385                 390                 395                 400

Pro Leu Ser Arg Lys Asp Val Lys Trp
                405
```

<210> SEQ ID NO 8
<211> LENGTH: 410
<212> TYPE: PRT
<213> ORGANISM: Artificial Sequence
<220> FEATURE:
<223> OTHER INFORMATION: recombinant chimeric ADI derived from
      M. hominis (catalytic domain) and M. arginini (alpha-helical
      domain)

<400> SEQUENCE: 8

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Ala Ile
        50                  55                  60

Met Lys Asp Arg Gly Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
                165                 170                 175

Tyr Ile Val Arg Arg Arg Glu Thr Leu Phe Ala Arg Phe Val Phe Arg
            180                 185                 190

Asn His Pro Lys Leu Val Asn Thr Pro Trp Tyr Tyr Asp Pro Ala Met
        195                 200                 205

Arg Met Ser Ile Glu Gly Gly Asp Val Phe Ile Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Val Ala Asn Lys Glu Val Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Gln Leu Asn Gly Leu Pro Leu Asp Arg Leu Leu Ala
305                 310                 315                 320
```

```
Ser Ile Ile Asn Lys Glu Pro Val Leu Ile Pro Ile Gly Gly Ala Gly
            325                 330                 335

Ala Thr Glu Met Glu Ile Ala Arg Glu Thr Asn Phe Asp Gly Thr Asn
            340                 345                 350

Tyr Leu Ala Ile Arg Pro Gly Leu Val Ile Gly Tyr Asp Arg Asn Glu
            355                 360                 365

Lys Thr Asn Ala Ala Leu Glu Ala Ala Gly Ile Thr Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

<210> SEQ ID NO 9
<211> LENGTH: 410
<212> TYPE: PRT
<213> ORGANISM: Artificial Sequence
<220> FEATURE:
<223> OTHER INFORMATION: recombinant chimeric ADI derived from
      M. hominis (catalytic domain) and M. arthritidis (alpha-helical
      domain)

<400> SEQUENCE: 9

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Ala Ile
    50                  55                  60

Met Lys Asp Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
            85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
            115                 120                 125

Glu Tyr Met Ile Ala Gly Ile Thr Lys His Asp Leu Lys Ile Glu Ser
    130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Phe Met Arg
            165                 170                 175

Tyr Ile Val Arg Arg Arg Glu Thr Leu Phe Ala Arg Phe Val Phe Arg
            180                 185                 190

Asn His Pro Lys Leu Val Asn Thr Pro Trp Tyr Tyr Asp Pro Ala Met
            195                 200                 205

Arg Met Ser Ile Glu Gly Gly Asp Val Phe Ile Tyr Asn Asn Glu Thr
    210                 215                 220

Leu Val Val Gly Val Ser Glu Arg Thr Asp Leu Asp Thr Ile Thr Leu
225                 230                 235                 240

Leu Ala Lys Asn Ile Val Ala Asn Lys Glu Val Glu Phe Lys Arg Ile
            245                 250                 255
```

Val Ala Ile Asn Val Pro Lys Trp Thr Asn Leu Met His Leu Asp Thr
                260                 265                 270

Trp Leu Thr Met Leu Asp Lys Asn Lys Phe Leu Tyr Ser Pro Ile Ala
            275                 280                 285

Asn Asp Val Phe Lys Phe Trp Asp Tyr Asp Leu Val Asn Gly Gly Ala
        290                 295                 300

Glu Pro Gln Pro Gln Leu Asn Gly Leu Pro Leu Asp Arg Leu Leu Ala
305                 310                 315                 320

Ser Ile Ile Asn Lys Glu Pro Val Leu Ile Pro Ile Gly Gly Ala Gly
                325                 330                 335

Ala Thr Glu Met Glu Ile Ala Arg Glu Thr Asn Phe Asp Gly Thr Asn
            340                 345                 350

Tyr Leu Ala Ile Arg Pro Gly Leu Val Ile Gly Tyr Asp Arg Asn Glu
        355                 360                 365

Lys Thr Asn Ala Ala Leu Glu Ala Ala Gly Ile Thr Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 10
<211> LENGTH: 410
<212> TYPE: PRT
<213> ORGANISM: Artificial Sequence
<220> FEATURE:
<223> OTHER INFORMATION: DS1-1 lysine reduction mutant of the
      recombinant chimeric ADI protein

<400> SEQUENCE: 10

Met Ser Val Phe Asp Ser His Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Val Asp Leu Ile Val
65                  70                  75                  80

Glu Thr Tyr Asp Leu Ala Ser Arg Glu Ala Lys Glu Lys Leu Leu Glu
                85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
        115                 120                 125

Glu Tyr Met Ile Ala Gly Ile Thr Arg His Asp Leu Lys Ile Glu Ser
    130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

```
Arg Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
            325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Thr Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

<210> SEQ ID NO 11
<211> LENGTH: 410
<212> TYPE: PRT
<213> ORGANISM: Artificial Sequence
<220> FEATURE:
<223> OTHER INFORMATION: DS1-2 lysine reduction mutant of the
      recombinant chimeric ADI protein

<400> SEQUENCE: 11

Met Ser Val Phe Asp Ser His Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Gln Phe Val Ala Glu
50                  55                  60

Leu Lys Ala Asn Asp Ile Asn Val Val Glu Leu Val Asp Leu Ile Val
65                  70                  75                  80

Glu Thr Tyr Asp Leu Ala Ser Arg Glu Ala Lys Glu Lys Leu Leu Glu
            85                  90                  95

Glu Phe Leu Asp Asp Ser Val Pro Val Leu Ser Asp Glu His Arg Ala
            100                 105                 110

Thr Val Arg Asn Phe Leu Gln Ser Gln Lys Ser Thr Arg Ser Leu Val
            115                 120                 125

Glu Tyr Met Ile Ala Gly Ile Thr Arg His Asp Leu Lys Ile Glu Ser
            130                 135                 140

Asp Leu Glu Leu Ile Val Asp Pro Met Pro Asn Leu Tyr Phe Thr Arg
```

```
        145                 150                 155                 160
Asp Pro Phe Ala Ser Val Gly Asn Gly Val Thr Ile His Tyr Met Arg
                165                 170                 175

Tyr Ile Val Arg Gln Arg Glu Thr Leu Phe Ser Arg Phe Val Phe Ser
                180                 185                 190

Asn His Pro Lys Leu Ile Asn Thr Pro Trp Tyr Tyr Asp Pro Ser Leu
                195                 200                 205

Arg Leu Ser Ile Glu Gly Gly Asp Val Phe Ile Tyr Asn Asn Asp Thr
                210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
                275                 280                 285

Asn Asp Val Phe Lys Phe Trp Asp Tyr Asp Leu Val Asn Gly Gly Ala
                290                 295                 300

Glu Pro Gln Pro Val Glu Asn Gly Leu Pro Leu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Leu Ala Ile Arg Pro Gly Val Val Ile Gly Tyr Ser Arg Asn Glu
                355                 360                 365

Lys Thr Asn Ala Ala Leu Glu Ala Ala Gly Ile Thr Val Leu Pro Phe
                370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 12
<211> LENGTH: 410
<212> TYPE: PRT
<213> ORGANISM: Artificial Sequence
<220> FEATURE:
<223> OTHER INFORMATION: DS1-3 lysine reduction mutant of the
      recombinant chimeric ADI protein

<400> SEQUENCE: 12

Met Ser Val Phe Asp Ser His Phe Asn Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Gln Gln Phe Val Ala Glu
                50                  55                  60

Leu Arg Ala Asn Asp Ile Asn Val Val Glu Leu Val Asp Leu Ile Val
65                  70                  75                  80

Glu Thr Tyr Asp Leu Ala Ser Arg Glu Ala Gln Glu Asn Leu Leu Glu
                85                  90                  95
```

Glu Phe Leu Asp Asp Ser Val Pro Val Leu Ser Asp Glu His Arg Ala
                100                 105                 110

Thr Val Arg Asn Phe Leu Gln Ser Gln Lys Ser Thr Arg Ser Leu Val
            115                 120                 125

Glu Tyr Met Ile Ala Gly Ile Thr Arg His Asp Leu Gly Ile Glu Ser
        130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Ile Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Arg Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Arg Asp Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Thr Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 13
<211> LENGTH: 410
<212> TYPE: PRT
<213> ORGANISM: Artificial Sequence
<220> FEATURE:
<223> OTHER INFORMATION: DS1-4 lysine reduction mutant of the
      recombinant chimeric ADI protein

<400> SEQUENCE: 13

Met Ser Val Phe Asp Ser His Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Thr Glu His Gln Gln Phe Val Ala Glu
 50                  55                  60

Leu Arg Ala Asn Asp Ile Asn Val Val Glu Leu Val Asp Leu Ile Val
 65                  70                  75                  80

Glu Thr Tyr Asp Leu Ala Ser Arg Glu Ala Gln Glu Asn Leu Leu Glu
                 85                  90                  95

Glu Phe Leu Asp Asp Ser Val Pro Val Leu Ser Asp Glu His Arg Ala
            100                 105                 110

Thr Val Arg Asn Phe Leu Gln Ser Gln Lys Ser Thr Arg Ser Leu Val
        115                 120                 125

Glu Tyr Met Ile Ala Gly Ile Thr Arg His Asp Leu Gly Ile Glu Ser
130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Ile Val Arg Gln Arg Glu Thr Leu Phe Ser Arg Phe Val Phe Ser
            180                 185                 190

Asn His Pro Leu Leu Ile Asn Thr Pro Trp Tyr Tyr Asp Pro Ser Leu
        195                 200                 205

Arg Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Arg Arg Ile
                245                 250                 255

Val Ala Ile Asn Val Pro Lys Trp Thr Asn Leu Met His Leu Asp Thr
            260                 265                 270

Trp Leu Thr Met Leu Asp Arg Asp Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Val Glu Asn Gly Leu Pro Leu Glu Gly Leu Leu Gln
305                 310                 315                 320

Ser Ile Ile Asn Arg Arg Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Thr Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Arg Asp Val Lys Trp
                405                 410

<210> SEQ ID NO 14
<211> LENGTH: 409
<212> TYPE: PRT
<213> ORGANISM: Artificial Sequence
<220> FEATURE:
<223> OTHER INFORMATION: Mutated M. hominis ADI sequence

<400> SEQUENCE: 14

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Lys Ile
50                  55                  60

Met Lys Asp Arg Gly Ile Asn Val Val Glu Leu Thr Asp Leu Val Ala
65                      70                  75                  80

Glu Thr Tyr Asp Leu Ala Ser Lys Ala Lys Glu Glu Phe Ile Glu
                85                  90                  95

Thr Phe Leu Glu Glu Thr Val Pro Val Leu Thr Glu Ala Asn Lys Glu
                100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
        130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                180                 185                 190

His Pro Lys Leu Val Lys Thr Pro Trp Tyr Tyr Asp Pro Ala Met Lys
                195                 200                 205

Met Ser Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
                260                 265                 270

Leu Thr Met Leu Asp Lys Asn Lys Phe Leu Tyr Ser Pro Ile Ala Asn
            275                 280                 285

Asp Val Phe Lys Phe Trp Asp Tyr Asp Leu Val Asn Gly Gly Ala Glu
            290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
            370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405
```

```
<210> SEQ ID NO 15
<211> LENGTH: 402
<212> TYPE: PRT
<213> ORGANISM: Mycoplasma alligatoris

<400> SEQUENCE: 15

Met Ser Lys Ile Asn Val Tyr Ser Glu Val Gly Arg Leu Lys Glu Val
1               5                   10                  15

Leu Val His Thr Pro Gly Asp Glu Ile Arg Arg Ile Ser Pro Thr Arg
            20                  25                  30

Leu Glu Glu Leu Leu Phe Ser Ala Ile Leu Glu Pro Asp Thr Ala Ile
        35                  40                  45

Glu Glu His Lys Arg Phe Leu Asn Val Leu Glu Lys Asn Gly Ile Lys
    50                  55                  60

Ala Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
            100                 105                 110

Lys Ser Gln Lys Glu Phe Ser Thr Lys Lys Met Val Arg Ile Met Met
        115                 120                 125

Ala Gly Ile Asp Lys Lys Glu Ile Asn Ile Asp Leu Asp Arg Asp Leu
    130                 135                 140

Val Val Asp Pro Met Pro Asn Leu Tyr Phe Thr Arg Asp Pro Phe Ala
145                 150                 155                 160

Ser Val Gly Asn Gly Ile Ser Leu His Asn Met Lys Tyr Gln Thr Arg
                165                 170                 175

Lys Arg Glu Thr Ile Phe Ala Gln Phe Ile Phe Lys Tyr Asn Lys Asp
            180                 185                 190

Tyr Lys Thr Thr Pro His Trp Phe Asp Arg Phe Asp His Gly Ser Ile
        195                 200                 205

Glu Gly Gly Asp Val Phe Val Tyr Thr Lys Asp Thr Leu Val Ile Gly
    210                 215                 220

Ile Ser Glu Arg Thr Thr Lys Glu Ala Val Leu Asn Ile Ala Lys Lys
225                 230                 235                 240

Ile Lys Ala Asn Thr Asp Ser Lys Phe Lys Lys Ile Val Ala Ile Asn
                245                 250                 255

Val Pro Pro Met Pro Asn Leu Met His Leu Asp Thr Trp Ile Thr Met
            260                 265                 270

Val Asp His Asp Lys Phe Leu Tyr Ser Pro Asn Met Met Lys Ser Leu
        275                 280                 285

Lys Phe Trp Leu Ile Asp Leu Ser Lys Glu Ile Lys Met Val Glu Leu
    290                 295                 300

Glu Glu Ser Leu Ser Asn Met Leu Glu Ala Ile Ile Gly Lys Lys Pro
305                 310                 315                 320

Ile Leu Ile Pro Ile Ala Gly Lys Asn Ala Ser Gln Leu Asp Ile Asp
                325                 330                 335

Ile Glu Thr His Phe Asp Gly Thr Asn Tyr Leu Thr Ile Ala Pro Gly
            340                 345                 350

Val Val Val Gly Tyr Ser Arg Asn Lys Leu Thr Gln Lys Ala Leu Glu
        355                 360                 365

Asp Ala Gly Val Lys Val Leu Ser Phe Asp Gly Asn Gln Leu Ser Leu
    370                 375                 380
```

```
Gly Met Gly Ser Ala Arg Cys Met Ser Met Pro Leu Val Arg Glu Asp
385                 390                 395                 400

Ile Lys

<210> SEQ ID NO 16
<211> LENGTH: 401
<212> TYPE: PRT
<213> ORGANISM: Mycoplasma colombinum

<400> SEQUENCE: 16

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
        35                  40                  45

Lys Glu His Lys Gly Phe Leu Lys Ile Leu Gln Asp Lys Gly Ile Lys
    50                  55                  60

Val Ile Gln Leu Ser Asp Leu Val Ala Glu Thr Tyr Thr Tyr His Ala
65                  70                  75                  80

Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
            100                 105                 110

Leu Ser Lys Glu Gly Thr Pro Val Ala Met Val Arg Thr Met Met Ala
        115                 120                 125

Gly Val Ser Lys Gln Glu Leu Asn Val Glu Ser Glu Thr Glu Leu Val
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
            180                 185                 190

Lys Thr Thr Pro His Trp Phe Asp Arg Leu Asp Glu Gly Asn Ile Glu
        195                 200                 205

Gly Gly Asp Val Phe Ile Tyr Asn Lys Asp Thr Leu Val Ile Gly Val
210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350
```

```
Val Val Gly Tyr Ser Arg Asn Ile Lys Thr Glu Ala Ala Leu Arg Ala
            355                 360                 365

Ala Gly Val Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400

Lys

<210> SEQ ID NO 17
<211> LENGTH: 401
<212> TYPE: PRT
<213> ORGANISM: Mycoplasma gallinarum

<400> SEQUENCE:

```
Leu Ile Pro Ile Ala Gly Glu Gly Ala Ser Gln Leu Asp Ile Asp Ile
            325                 330                 335

Glu Thr His Phe Asp Gly Thr Asn Tyr Leu Thr Ile Ala Pro Gly Val
            340                 345                 350

Val Val Gly Tyr Ser Arg Asn Glu Lys Thr Glu Lys Ala Leu Lys Ala
            355                 360                 365

Ala Gly Ile Thr Val Leu Ser Phe Glu Gly Asn Gln Leu Ser Leu Gly
            370                 375                 380

Met Gly Ser Ala Arg Cys Met Ser Met Pro Leu Val Arg Glu Asp Val
385                 390                 395                 400

Lys

<210> SEQ ID NO 18
<211> LENGTH: 410
<212> TYPE: PRT
<213> ORGANISM: Mycoplasma gatea

<400> SEQUENCE: 18

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Leu Phe Val Ser Glu
        50                  55                  60

Leu Lys Ala Asn Asp Ile Asn Val Val Glu Leu Thr Asp Leu Val Thr
65                  70                  75                  80

Glu Thr Tyr Asp Leu Ala Ser Gln Glu Ala Lys Asp Asn Leu Ile Glu
                85                  90                  95

Glu Phe Leu Glu Asp Ser Glu Pro Val Leu Thr Glu Glu Leu Lys Ser
            100                 105                 110

Val Val Arg Thr Tyr Leu Lys Ser Ile Lys Ser Thr Arg Glu Leu Ile
            115                 120                 125

Gln Met Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Ile Tyr Asn Asn Asn Thr
210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285
```

```
Asn Asp Val Phe Lys Phe Trp Asp Tyr Asp Leu Val Asn Gly Gly Glu
        290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
                340                 345                 350

Tyr Leu Ala Ile Arg Pro Gly Val Val Gly Tyr Ser Arg Asn Glu
                355                 360                 365

Lys Thr Asn Ala Ala Leu Glu Ala Ala Gly Ile Lys Val Leu Pro Phe
        370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 19
<211> LENGTH: 401
<212> TYPE: PRT
<213> ORGANISM: Mycoplasma iners

<400> SEQUENCE: 19

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
                20                  25                  30

Leu Asp Glu Leu Leu Phe Ser Ala Ile Leu Glu Pro Ser Ala Ala Ile
            35                  40                  45

Gln Glu His Lys Ser Phe Leu Lys Ile Leu Gln Asp Arg Gly Ile Lys
        50                  55                  60

Thr Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
                100                 105                 110

Leu Ser Met Gln Gly Glu Pro Val Lys Met Val Arg Thr Met Met Ala
            115                 120                 125

Gly Val Ser Lys Gln Glu Leu Asn Val Glu Ser Glu Val Glu Leu Ile
        130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
        210                 215                 220

Ser Glu Arg Thr Asn Lys Glu Ala Ile Thr Ile Ala Lys His Ile
225                 230                 235                 240

Gln Asp Asn Lys Glu Ala Gln Phe Lys Lys Ile Val Ala Ile Asn Val
```

```
                       245                 250                 255
Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
            275                 280                 285

Val Trp Glu Ile Asp Leu Ser Lys Pro Ile Glu Met Val Glu Thr Asn
    290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
            325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
            355                 360                 365

Ala Gly Val Thr Val Leu Ser Phe Glu Gly Asn Gln Leu Ser Leu Gly
            370                 375                 380

Met Gly Ser Ala Arg Cys Met Ser Met Pro Leu Val Arg Glu Asp Val
385                 390                 395                 400

Lys

<210> SEQ ID NO 20
<211> LENGTH: 410
<212> TYPE: PRT
<213> ORGANISM: Mycoplasma phocicerabrale

<400> SEQUENCE: 20

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60

Leu Lys Asp Asn Gly Ile Asn Val Val Glu Leu Thr Asp Leu Val Ala
65                  70                  75                  80

Glu Thr Phe Asp Leu Ala Ser Lys Glu Glu Gln Lys Leu Ile Glu
            85                  90                  95

Glu Phe Leu Glu Asp Ser Glu Pro Val Leu Ser Glu Ala His Lys Thr
            100                 105                 110

Ala Val Arg Lys Phe Leu Thr Ser Arg Lys Ser Thr Arg Glu Met Val
            115                 120                 125

Glu Phe Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
            180                 185                 190

Asn His Pro Lys Leu Val Lys Thr Pro Trp Tyr Tyr Asp Pro Ala Met
            195                 200                 205

Lys Met Ser Ile Glu Gly Gly Asp Val Phe Ile Tyr Asn Asn Asp Thr
```

```
            210                 215                 220
Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
                275                 280                 285

Asn Asp Val Phe Lys Phe Trp Asp Tyr Asp Leu Val Asn Gly Gly Ala
            290                 295                 300

Glu Pro Gln Pro Lys Glu Asn Gly Leu Pro Leu Gly Leu Leu Gln
305                 310                 315                 320

Ser Ile Ile Asn Lys Lys Pro Val Leu Ile Pro Ile Ala Gly Asn Asn
                325                 330                 335

Ala Ser His Ile Asp Ile Glu Arg Glu Thr His Phe Asp Gly Thr Asn
                340                 345                 350

Tyr Leu Ala Ile Lys Pro Gly Val Val Ile Gly Tyr Ala Arg Asn Glu
                355                 360                 365

Lys Thr Asn Ala Ala Leu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 21
<211> LENGTH: 410
<212> TYPE: PRT
<213> ORGANISM: Mycoplasma phocidae

<400> SEQUENCE: 21

Met Ser Val Phe Asp Ser Lys Phe Asn Gly Ile His Val Tyr Ser Glu
1               5

```
Tyr Lys Val Arg Gln Arg Glu Thr Leu Phe Ser Arg Phe Ile Phe Ala
                180                 185                 190

Asn His Pro Lys Leu Met Asn Thr Pro Leu Tyr Tyr Asn Pro Asp Met
            195                 200                 205

Lys Leu Ser Ile Glu Gly Gly Asp Val Phe Val Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
            290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
            370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 22
<211> LENGTH: 413
<212> TYPE: PRT
<213> ORGANISM: Artificial Sequence
<220> FEATURE:
<223> OTHER INFORMATION: C2DS1 recombinant chimeric ADI protein

<400> SEQUENCE: 22

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Asp Glu Leu Val Ala
65                  70                  75                  80

Gln Thr Tyr Asp Gln Val Asp Gln Lys Ile Lys Asp Glu Phe Ile Asp
                85                  90                  95

Gln Trp Leu Gln Glu Ala Lys Pro Val Leu Asn Asp Gln Leu Lys Lys
            100                 105                 110

Leu Val Lys Asn Tyr Leu Leu Lys Ser Gln Lys Glu Phe Ser Thr Lys
        115                 120                 125
```

```
Lys Met Val Arg Ile Met Met Ala Gly Ile Asp Lys Lys Glu Ile Asn
            130                 135                 140

Ile Asp Leu Asp Arg Asp Leu Val Val Asp Pro Met Pro Asn Leu Tyr
145                 150                 155                 160

Phe Thr Arg Asp Pro Phe Ala Ser Val Gly Asn Gly Val Thr Ile His
                165                 170                 175

Tyr Met Arg Tyr Lys Val Arg Gln Arg Glu Thr Leu Phe Ser Arg Phe
                180                 185                 190

Val Phe Ser Asn His Pro Lys Leu Ile Asn Thr Pro Trp Tyr Tyr Asp
                195                 200                 205

Pro Ser Leu Lys Leu Ser Ile Glu Gly Gly Asp Val Phe Ile Tyr Asn
210                 215                 220

Asn Asp Thr Leu Val Val Gly Val Ser Glu Arg Thr Asp Leu Gln Thr
225                 230                 235                 240

Val Thr Leu Leu Ala Lys Asn Ile Val Ala Asn Lys Glu Ser Glu Phe
                245                 250                 255

Lys Arg Ile Val Ala Ile Asn Val Pro Lys Trp Thr Asn Leu Met His
                260                 265                 270

Leu Asp Thr Trp Leu Thr Met Leu Asp Lys Asp Lys Phe Leu Tyr Ser
                275                 280                 285

Pro Ile Ala Asn Asp Val Phe Lys Phe Trp Asp Tyr Asp Leu Val Asn
290                 295                 300

Gly Gly Ala Glu Pro Gln Pro Val Glu Asn Gly Leu Pro Leu Glu Gly
305                 310                 315                 320

Leu Leu Gln Ser Ile Ile Asn Lys Lys Pro Val Leu Ile Pro Ile Ala
                325                 330                 335

Gly Glu Gly Ala Ser Gln Met Glu Ile Glu Arg Glu Thr His Phe Asp
                340                 345                 350

Gly Thr Asn Tyr Leu Ala Ile Arg Pro Gly Val Val Ile Gly Tyr Ser
                355                 360                 365

Arg Asn Glu Lys Thr Asn Ala Ala Leu Glu Ala Ala Gly Ile Lys Val
                370                 375                 380

Leu Pro Phe His Gly Asn Gln Leu Ser Leu Gly Met Gly Asn Ala Arg
385                 390                 395                 400

Cys Met Ser Met Pro Leu Ser Arg Lys Asp Val Lys Trp
                405                 410

<210> SEQ ID NO 23
<211> LENGTH: 410
<212> TYPE: PRT
<213> ORGANISM: Artificial Sequence
<220> FEATURE:
<223> OTHER INFORMATION: C2DS3 recombinant chimeric ADI protein

<400> SEQUENCE: 23

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
        50                  55                  60

Leu Lys Ala Asn Asp Ile Asn Val Val Glu Leu Val Asp Leu Ile Val
65                  70                  75                  80
```

```
Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
            115                 120                 125

Glu Tyr Met Ile Ala Gly Ile Thr Lys His Asp Leu Lys Ile Glu Ser
130             135                 140

Asp Leu Glu Leu Ile Val Asp Pro Met Pro Asn Leu Tyr Phe Thr Arg
145             150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
                180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Val Thr Leu
225             230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
            290                 295                 300

Glu Pro Gln Pro Val Glu Asn Gly Leu Pro Leu Glu Gly Leu Leu Gln
305             310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
                340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385             390                 395                 400

Met Pro Leu Ser Arg Lys Asp Val Lys Trp
                405                 410

<210> SEQ ID NO 24
<211> LENGTH: 412
<212> TYPE: PRT
<213> ORGANISM: Artificial Sequence
<220> FEATURE:
<223> OTHER INFORMATION: C2DS4 recombinant chimeric ADI protein

<400> SEQUENCE: 24

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30
```

```
Asp Tyr Ile Thr Pro Ala Arg Leu Asp Glu Leu Leu Phe Ser Ala Ile
         35                  40                  45

Leu Glu Ser His Asp Ala Arg Lys Glu His Lys Gln Phe Val Ala Glu
 50                  55                  60

Leu Lys Ala Asn Asp Ile Asn Val Val Glu Leu Ser Asp Leu Val Ala
 65                  70                  75                  80

Glu Thr Tyr Thr Tyr His Ala Thr Gln Lys Glu Arg Glu Ala Phe Ile
                 85                  90                  95

Glu Lys Trp Leu Asp Glu Ala Glu Pro Ala Leu Thr Lys Asp Leu Arg
                100                 105                 110

Ala Lys Val Lys Ser Tyr Val Leu Ser Lys Glu Gly Thr Pro Val Ala
                115                 120                 125

Met Val Arg Thr Met Met Ala Gly Val Ser Lys Gln Glu Leu Asn Val
    130                 135                 140

Glu Ser Glu Thr Glu Leu Val Val Asp Pro Met Pro Asn Leu Tyr Phe
145                 150                 155                 160

Thr Arg Asp Pro Phe Ala Ser Val Gly Asn Gly Val Thr Ile His Tyr
                165                 170                 175

Met Arg Tyr Lys Val Arg Gln Arg Glu Thr Leu Phe Ser Arg Phe Val
            180                 185                 190

Phe Ser Asn His Pro Lys Leu Ile Asn Thr Pro Trp Tyr Tyr Asp Pro
        195                 200                 205

Ser Leu Lys Leu Ser Ile Glu Gly Gly Asp Val Phe Ile Tyr Asn Asn
    210                 215                 220

Asp Thr Leu Val Val Gly Val Ser Glu Arg Thr Asp Leu Gln Thr Val
225                 230                 235                 240

Thr Leu Leu Ala Lys Asn Ile Val Ala Asn Lys Glu Ser Glu Phe Lys
                245                 250                 255

Arg Ile Val Ala Ile Asn Val Pro Lys Trp Thr Asn Leu Met His Leu
                260                 265                 270

Asp Thr Trp Leu Thr Met Leu Asp Lys Asp Lys Phe Leu Tyr Ser Pro
            275                 280                 285

Ile Ala Asn Asp Val Phe Lys Phe Trp Asp Tyr Asp Leu Val Asn Gly
        290                 295                 300

Gly Ala Glu Pro Gln Pro Val Glu Asn Gly Leu Pro Leu Glu Gly Leu
305                 310                 315                 320

Leu Gln Ser Ile Ile Asn Lys Lys Pro Val Leu Ile Pro Ile Ala Gly
                325                 330                 335

Glu Gly Ala Ser Gln Met Glu Ile Glu Arg Glu Thr His Phe Asp Gly
            340                 345                 350

Thr Asn Tyr Leu Ala Ile Arg Pro Gly Val Val Ile Gly Tyr Ser Arg
        355                 360                 365

Asn Glu Lys Thr Asn Ala Ala Leu Glu Ala Ala Gly Ile Lys Val Leu
    370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
                405                 410
```

<210> SEQ ID NO 25
<211> LENGTH: 410
<212> TYPE: PRT
<213> ORGANISM: Artificial Sequence
<220> FEATURE:
<223> OTHER INFORMATION: C2DS5 recombinant chimeric ADI protein

<400> SEQUENCE: 25

```
Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Thr Asp Leu Val Thr
65                  70                  75                  80

Glu Thr Tyr Asp Leu Ala Ser Gln Glu Ala Lys Asp Asn Leu Ile Glu
                85                  90                  95

Glu Phe Leu Glu Asp Ser Glu Pro Val Leu Thr Glu Glu Leu Lys Ser
            100                 105                 110

Val Val Arg Thr Tyr Leu Lys Ser Ile Lys Ser Thr Arg Glu Leu Ile
            115                 120                 125

Gln Met Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
            195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
```

<210> SEQ ID NO 26
<211> LENGTH: 410
<212> TYPE: PRT
<213> ORGANISM: Artificial Sequence
<220> FEATURE:
<223> OTHER INFORMATION: C2DS6 recombinant chimeric ADI protein

<400> SEQUENCE: 26

```
Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Thr Asp Leu Val Ala
65                  70                  75                  80

Glu Thr Phe Asp Leu Ala Ser Lys Glu Gln Glu Lys Leu Ile Glu
                85                  90                  95

Glu Phe Leu Glu Asp Ser Glu Pro Val Leu Ser Glu Ala His Lys Thr
            100                 105                 110

Ala Val Arg Lys Phe Leu Thr Ser Arg Lys Ser Thr Arg Glu Met Val
        115                 120                 125

Glu Phe Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
```

355                 360                 365
Lys Thr Asn Ala Ala Leu Glu Ala Ala Gly Ile Lys Val Leu Pro Phe
            370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 27
<211> LENGTH: 410
<212> TYPE: PRT
<213> ORGANISM: Artificial Sequence
<220> FEATURE:
<223> OTHER INFORMATION: C2DS7 recombinant chimeric ADI protein

<400> SEQUENCE: 27

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Thr Asp Leu Val Ser
65                  70                  75                  80

Glu Thr Tyr Asp Met Val Ser Lys Glu Lys Gln Glu Lys Leu Ile Glu
                85                  90                  95

Glu Phe Leu Glu Asp Ser Glu Pro Val Leu Ser Glu Glu His Lys Gly
            100                 105                 110

Leu Val Arg Lys Phe Leu Lys Ser Leu Lys Ser Ser Lys Glu Leu Ile
        115                 120                 125

Gln Tyr Met Met Ala Gly Ile Thr Lys His Asp Leu Asn Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Ser Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln

```
                    305                 310                 315                 320
              Ser Ile Ile Asn Lys Lys Pro Val Leu Ile Pro Ile Ala Gly Glu Gly
                              325                 330                 335

Ala Ser Gln Met Glu Ile Glu Arg Glu Thr His Phe Asp Gly Thr Asn
                              340                 345                 350

Tyr Leu Ala Ile Arg Pro Gly Val Val Ile Gly Tyr Ser Arg Asn Glu
                              355                 360                 365

Lys Thr Asn Ala Ala Leu Glu Ala Ala Gly Ile Lys Val Leu Pro Phe
                              370                 375                 380

His Gly Asn Gln Leu Ser Leu Gly Met Gly Asn Ala Arg Cys Met Ser
              385                 390                 395                 400

Met Pro Leu Ser Arg Lys Asp Val Lys Trp
                              405                 410

<210> SEQ ID NO 28
<211> LENGTH: 402
<212> TYPE: PRT
<213> ORGANISM: Artificial Sequence
<220> FEATURE:
<223> OTHER INFORMATION: C4DS1 recombinant chimeric ADI protein

<400> SEQUENCE: 28

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
                20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
        50                  55                  60

Val Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
                100                 105                 110

Lys Ser Gln Lys Glu Phe Ser Thr Lys Lys Met Val Arg Ile Met Met
            115                 120                 125

Ala Gly Ile Asp Lys Lys Glu Ile Asn Ile Asp Leu Asp Arg Asp Leu
        130                 135                 140

Val Val Asp Pro Met Pro Asn Leu Tyr Phe Thr Arg Asp Pro Phe Ala
145                 150                 155                 160

Ser Ala Gly Asn Gly Ile Ser Leu Asn Asn Met Lys Tyr Val Thr Arg
                165                 170                 175

Lys Arg Glu Thr Ile Phe Ala Glu Phe Ile Phe Ala Thr His Pro Asp
                180                 185                 190

Tyr Lys Thr Thr Pro His Trp Phe Asp Arg Leu Asp Glu Gly Asn Ile
            195                 200                 205

Glu Gly Gly Asp Val Phe Ile Tyr Asn Lys Asp Thr Leu Val Ile Gly
        210                 215                 220

Val Ser Glu Arg Thr Asn Lys Glu Ala Ile Leu Thr Ile Ala Lys Lys
225                 230                 235                 240

Ile Lys Asn Asn Lys Glu Ala Lys Phe Lys Lys Ile Val Ala Ile Asn
                245                 250                 255

Val Pro Pro Met Pro Asn Leu Met His Leu Asp Thr Trp Leu Thr Met
```

```
                  260                 265                 270
Val Asp Lys Asp Lys Phe Leu Tyr Ser Pro Asn Met Leu Ser Val Leu
                275                 280                 285

Lys Val Trp Glu Ile Asp Leu Ser Lys Glu Ile Glu Met Val Glu Thr
            290                 295                 300

Asn Lys Pro Leu Ala Asp Val Leu Glu Ser Ile Ile Gly Val Lys Pro
305                 310                 315                 320

Val Leu Ile Pro Ile Ala Gly Lys Gly Ala Thr Gln Leu Asp Ile Asp
                325                 330                 335

Ile Glu Thr His Phe Asp Gly Thr Asn Tyr Leu Thr Ile Ala Pro Gly
                340                 345                 350

Val Val Val Gly Tyr Ser Arg Asn Ile Lys Thr Glu Ala Ala Leu Arg
            355                 360                 365

Ala Ala Gly Val Thr Val Leu Ser Phe Glu Gly Asn Gln Leu Ser Leu
        370                 375                 380

Gly Met Gly Ser Ala Arg Cys Met Ser Met Pro Leu Val Arg Glu Asp
385                 390                 395                 400

Val Lys

<210> SEQ ID NO 29
<211> LENGTH: 399
<212> TYPE: PRT
<213> ORGANISM: Artificial Sequence
<220> FEATURE:
<223> OTHER INFORMATION: C4DS2 recombinant chimeric ADI protein

<400> SEQUENCE: 29

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
                20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
        50                  55                  60

Val Ile Gln Leu Ile Asp Leu Val Ala Glu Thr Tyr Asp Leu Ala Ser
65                  70                  75                  80

Gln Glu Ala Lys Asp Lys Leu Ile Glu Glu Phe Leu Glu Asp Ser Glu
                85                  90                  95

Pro Val Leu Ser Glu Glu His Lys Val Val Arg Asn Phe Leu Lys
                100                 105                 110

Ala Lys Lys Thr Ser Arg Glu Leu Val Glu Ile Met Met Ala Gly Ile
            115                 120                 125

Thr Lys Tyr Asp Leu Gly Ile Glu Ala Asp His Glu Leu Ile Val Asp
        130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Ala Thr His Pro Asp Tyr Lys Thr
            180                 185                 190

Thr Pro His Trp Phe Asp Arg Leu Asp Glu Gly Asn Ile Glu Gly Gly
        195                 200                 205

Asp Val Phe Ile Tyr Asn Lys Asp Thr Leu Val Ile Gly Val Ser Glu
210                 215                 220
```

```
Arg Thr Asn Lys Glu Ala Ile Leu Thr Ile Ala Lys Ile Lys Asn
225                 230                 235                 240

Asn Lys Glu Ala Lys Phe Lys Lys Ile Val Ala Ile Asn Val Pro Pro
            245                 250                 255

Met Pro Asn Leu Met His Leu Asp Thr Trp Leu Thr Met Val Asp Lys
        260                 265                 270

Asp Lys Phe Leu Tyr Ser Pro Asn Met Leu Ser Val Leu Lys Val Trp
        275                 280                 285

Glu Ile Asp Leu Ser Lys Glu Ile Glu Met Val Glu Thr Asn Lys Pro
    290                 295                 300

Leu Ala Asp Val Leu Glu Ser Ile Ile Gly Val Lys Pro Val Leu Ile
305                 310                 315                 320

Pro Ile Ala Gly Lys Gly Ala Thr Gln Leu Asp Ile Asp Ile Glu Thr
                325                 330                 335

His Phe Asp Gly Thr Asn Tyr Leu Thr Ile Ala Pro Gly Val Val Val
            340                 345                 350

Gly Tyr Ser Arg Asn Ile Lys Thr Glu Ala Ala Leu Arg Ala Ala Gly
        355                 360                 365

Val Thr Val Leu Ser Phe Glu Gly Asn Gln Leu Ser Leu Gly Met Gly
    370                 375                 380

Ser Ala Arg Cys Met Ser Met Pro Leu Val Arg Glu Asp Val Lys
385                 390                 395

<210> SEQ ID NO 30
<211> LENGTH: 399
<212> TYPE: PRT
<213> ORGANISM: Artificial Sequence
<220> FEATURE:
<223> OTHER INFORMATION: C4DS3 recombinant chimeric ADI protein

<400> SEQUENCE: 30

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
        35                  40                  45

Lys Glu His Lys Gly Phe Leu Lys Ile Leu Gln Asp Lys Gly Ile Lys
    50                  55                  60

Val Ile Gln Leu Val Asp Leu Ile Val Glu Thr Tyr Asp Leu Ala Ser
65                  70                  75                  80

Lys Glu Ala Lys Glu Lys Leu Leu Glu Glu Phe Leu Asp Asp Ser Val
                85                  90                  95

Pro Val Leu Ser Asp Glu His Arg Ala Thr Val Lys Lys Phe Leu Gln
            100                 105                 110

Ser Gln Lys Ser Thr Arg Ser Leu Val Glu Tyr Met Ile Ala Gly Ile
        115                 120                 125

Thr Lys His Asp Leu Lys Ile Glu Ser Asp Leu Glu Leu Ile Val Asp
    130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Ala Thr His Pro Asp Tyr Lys Thr
            180                 185                 190
```

```
Thr Pro His Trp Phe Asp Arg Leu Asp Glu Gly Asn Ile Glu Gly Gly
        195                 200                 205

Asp Val Phe Ile Tyr Asn Lys Asp Thr Leu Val Ile Gly Val Ser Glu
    210                 215                 220

Arg Thr Asn Lys Glu Ala Ile Leu Thr Ile Ala Lys Lys Ile Lys Asn
225                 230                 235                 240

Asn Lys Glu Ala Lys Phe Lys Lys Ile Ala Ile Asn Val Pro Pro
                245                 250                 255

Met Pro Asn Leu Met His Leu Asp Thr Trp Leu Thr Met Val Asp Lys
            260                 265                 270

Asp Lys Phe Leu Tyr Ser Pro Asn Met Leu Ser Val Leu Lys Val Trp
                275                 280                 285

Glu Ile Asp Leu Ser Lys Glu Ile Glu Met Val Glu Thr Asn Lys Pro
            290                 295                 300

Leu Ala Asp Val Leu Glu Ser Ile Ile Gly Val Lys Pro Val Leu Ile
305                 310                 315                 320

Pro Ile Ala Gly Lys Gly Ala Thr Gln Leu Asp Ile Asp Ile Glu Thr
                325                 330                 335

His Phe Asp Gly Thr Asn Tyr Leu Thr Ile Ala Pro Gly Val Val Val
            340                 345                 350

Gly Tyr Ser Arg Asn Ile Lys Thr Glu Ala Ala Leu Arg Ala Ala Gly
            355                 360                 365

Val Thr Val Leu Ser Phe Glu Gly Asn Gln Leu Ser Leu Gly Met Gly
        370                 375                 380

Ser Ala Arg Cys Met Ser Met Pro Leu Val Arg Glu Asp Val Lys
385                 390                 395

<210> SEQ ID NO 31
<211> LENGTH: 399
<212> TYPE: PRT
<213> ORGANISM: Artificial Sequence
<220> FEATURE:
<223> OTHER INFORMATION: C4DS5 recombinant chimeric ADI protein

<400> SEQUENCE: 31

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
        35                  40                  45

Lys Glu His Lys Gly Phe Leu Lys Ile Leu Gln Asp Lys Gly Ile Lys
    50                  55                  60

Val Ile Gln Leu Thr Asp Leu Val Thr Glu Thr Tyr Asp Leu Ala Ser
65                  70                  75                  80

Gln Glu Ala Lys Asp Asn Leu Ile Glu Glu Phe Leu Glu Asp Ser Glu
                85                  90                  95

Pro Val Leu Thr Glu Glu Leu Lys Ser Val Val Arg Thr Tyr Leu Lys
            100                 105                 110

Ser Ile Lys Ser Thr Arg Glu Leu Ile Gln Met Met Met Ala Gly Ile
        115                 120                 125

Thr Lys Tyr Asp Leu Gly Ile Glu Ala Asp His Glu Leu Ile Val Asp
    130                 135                 140

Pro Met Pro Asn Leu Tyr Phe Thr Arg Asp Pro Phe Ala Ser Ala Gly
145                 150                 155                 160
```

```
Asn Gly Ile Ser Leu Asn Asn Met Lys Tyr Val Thr Arg Lys Arg Glu
            165                 170                 175

Thr Ile Phe Ala Glu Phe Ile Phe Ala Thr His Pro Asp Tyr Lys Thr
            180                 185                 190

Thr Pro His Trp Phe Asp Arg Leu Asp Glu Gly Asn Ile Glu Gly Gly
            195                 200                 205

Asp Val Phe Ile Tyr Asn Lys Asp Thr Leu Val Ile Gly Val Ser Glu
            210                 215                 220

Arg Thr Asn Lys Glu Ala Ile Leu Thr Ile Ala Lys Lys Ile Lys Asn
225                 230                 235                 240

Asn Lys Glu Ala Lys Phe Lys Lys Ile Val Ala Ile Asn Val Pro Pro
            245                 250                 255

Met Pro Asn Leu Met His Leu Asp Thr Trp Leu Thr Met Val Asp Lys
            260                 265                 270

Asp Lys Phe Leu Tyr Ser Pro Asn Met Leu Ser Val Leu Lys Val Trp
            275                 280                 285

Glu Ile Asp Leu Ser Lys Glu Ile Glu Met Val Glu Thr Asn Lys Pro
            290                 295                 300

Leu Ala Asp Val Leu Glu Ser Ile Ile Gly Val Lys Pro Val Leu Ile
305                 310                 315                 320

Pro Ile Ala Gly Lys Gly Ala Thr Gln Leu Asp Ile Asp Ile Glu Thr
            325                 330                 335

His Phe Asp Gly Thr Asn Tyr Leu Thr Ile Ala Pro Gly Val Val Val
            340                 345                 350

Gly Tyr Ser Arg Asn Ile Lys Thr Glu Ala Ala Leu Arg Ala Ala Gly
            355                 360                 365

Val Thr Val Leu Ser Phe Glu Gly Asn Gln Leu Ser Leu Gly Met Gly
            370                 375                 380

Ser Ala Arg Cys Met Ser Met Pro Leu Val Arg Glu Asp Val Lys
385                 390                 395

<210> SEQ ID NO 32
<211> LENGTH: 399
<212> TYPE: PRT
<213> ORGANISM: Artificial Sequence
<220> FEATURE:
<223> OTHER INFORMATION: C4DS6 recombinant chimeric ADI protein

<400> SEQUENCE: 32

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
            50                  55                  60

Val Ile Gln Leu Thr Asp Leu Val Ala Glu Thr Phe Asp Leu Ala Ser
65                  70                  75                  80

Lys Glu Glu Gln Glu Lys Leu Ile Glu Glu Phe Leu Glu Asp Ser Glu
            85                  90                  95

Pro Val Leu Ser Glu Ala His Lys Thr Ala Val Arg Lys Phe Leu Thr
            100                 105                 110

Ser Arg Lys Ser Thr Arg Glu Met Val Glu Phe Met Met Ala Gly Ile
            115                 120                 125
```

Thr Lys Tyr Asp Leu Gly Ile Glu Ala Asp His Glu Leu Ile Val Asp
            130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
            165                 170                 175

Thr Ile Phe Ala Glu Phe Ile Phe Ala Thr His Pro Asp Tyr Lys Thr
            180                 185                 190

Thr Pro His Trp Phe Asp Arg Leu Asp Glu Gly Asn Ile Glu Gly Gly
            195                 200                 205

Asp Val Phe Ile Tyr Asn Lys Asp Thr Leu Val Ile Gly Val Ser Glu
            210                 215                 220

Arg Thr Asn Lys Glu Ala Ile Leu Thr Ile Ala Lys Lys Ile Lys Asn
225                 230                 235                 240

Asn Lys Glu Ala Lys Phe Lys Lys Ile Val Ala Ile Asn Val Pro Pro
            245                 250                 255

Met Pro Asn Leu Met His Leu Asp Thr Trp Leu Thr Met Val Asp Lys
            260                 265                 270

Asp Lys Phe Leu Tyr Ser Pro Asn Met Leu Ser Val Leu Lys Val Trp
            275                 280                 285

Glu Ile Asp Leu Ser Lys Glu Ile Glu Met Val Glu Thr Asn Lys Pro
290                 295                 300

Leu Ala Asp Val Leu Glu Ser Ile Ile Gly Val Lys Pro Val Leu Ile
305                 310                 315                 320

Pro Ile Ala Gly Lys Gly Ala Thr Gln Leu Asp Ile Asp Ile Glu Thr
            325                 330                 335

His Phe Asp Gly Thr Asn Tyr Leu Thr Ile Ala Pro Gly Val Val Val
            340                 345                 350

Gly Tyr Ser Arg Asn Ile Lys Thr Glu Ala Ala Leu Arg Ala Ala Gly
            355                 360                 365

Val Thr Val Leu Ser Phe Glu Gly Asn Gln Leu Ser Leu Gly Met Gly
            370                 375                 380

Ser Ala Arg Cys Met Ser Met Pro Leu Val Arg Glu Asp Val Lys
385                 390                 395

<210> SEQ ID NO 33
<211> LENGTH: 399
<212> TYPE: PRT
<213> ORGANISM: Artificial Sequence
<220> FEATURE:
<223> OTHER INFORMATION: C4DS7 recombinant chimeric ADI protein

<400> SEQUENCE: 33

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
            50                  55                  60

Val Ile Gln Leu Thr Asp Leu Val Ser Glu Thr Tyr Asp Met Val Ser
65                  70                  75                  80

Lys Glu Lys Gln Glu Lys Leu Ile Glu Glu Phe Leu Glu Asp Ser Glu
            85                  90                  95

```
Pro Val Leu Ser Glu Glu His Lys Gly Leu Val Arg Lys Phe Leu Lys
            100                 105                 110

Ser Leu Lys Ser Ser Lys Glu Leu Ile Gln Tyr Met Met Ala Gly Ile
            115                 120                 125

Thr Lys His Asp Leu Asn Ile Glu Ala Asp His Glu Leu Ile Val Asp
            130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
            165                 170                 175

Thr Ile Phe Ala Glu Phe Ile Phe Ala Thr His Pro Asp Tyr Lys Thr
            180                 185                 190

Thr Pro His Trp Phe Asp Arg Leu Asp Glu Gly Asn Ile Glu Gly Gly
            195                 200                 205

Asp Val Phe Ile Tyr Asn Lys Asp Thr Leu Val Ile Gly Val Ser Glu
            210                 215                 220

Arg Thr Asn Lys Glu Ala Ile Leu Thr Ile Ala Lys Lys Ile Lys Asn
225                 230                 235                 240

Asn Lys Glu Ala Lys Phe Lys Lys Ile Val Ala Ile Asn Val Pro Pro
            245                 250                 255

Met Pro Asn Leu Met His Leu Asp Thr Trp Leu Thr Met Val Asp Lys
            260                 265                 270

Asp Lys Phe Leu Tyr Ser Pro Asn Met Leu Ser Val Leu Lys Val Trp
            275                 280                 285

Glu Ile Asp Leu Ser Lys Glu Ile Glu Met Val Glu Thr Asn Lys Pro
            290                 295                 300

Leu Ala Asp Val Leu Glu Ser Ile Ile Gly Val Lys Pro Val Leu Ile
305                 310                 315                 320

Pro Ile Ala Gly Lys Gly Ala Thr Gln Leu Asp Ile Asp Ile Glu Thr
            325                 330                 335

His Phe Asp Gly Thr Asn Tyr Leu Thr Ile Ala Pro Gly Val Val Val
            340                 345                 350

Gly Tyr Ser Arg Asn Ile Lys Thr Glu Ala Ala Leu Arg Ala Ala Gly
            355                 360                 365

Val Thr Val Leu Ser Phe Glu Gly Asn Gln Leu Ser Leu Gly Met Gly
            370                 375                 380

Ser Ala Arg Cys Met Ser Met Pro Leu Val Arg Glu Asp Val Lys
385                 390                 395

<210> SEQ ID NO 34
<211> LENGTH: 401
<212> TYPE: PRT
<213> ORGANISM: Artificial Sequence
<220> FEATURE:
<223> OTHER INFORMATION: C4DS8 recombinant chimeric ADI protein

<400> SEQUENCE: 34

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
        50                  55                  60
```

```
Val Ile Gln Leu Ser Asp Leu Val Ala Glu Thr Tyr Val Lys Tyr Ala
 65                  70                  75                  80

Thr Ala Glu Gln Lys Ala Ala Phe Ile Glu Lys Tyr Leu Asp Glu Ala
                 85                  90                  95

Thr Pro Ala Leu Ser Ala Glu Asn Arg Glu Arg Ala Lys Lys Tyr Ile
            100                 105                 110

Leu Ser Leu Glu Met Gln Pro Val Lys Met Ile Arg Thr Met Met Ala
        115                 120                 125

Gly Leu Ser Lys Tyr Glu Leu Asn Val Glu Ser Asn Ile Glu Leu Ile
    130                 135                 140

Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
            180                 185                 190

Lys Thr Thr Pro His Trp Phe Asp Arg Leu Asp Glu Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
    290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 35
<211> LENGTH: 401
<212> TYPE: PRT
<213> ORGANISM: Artificial Sequence
<220> FEATURE:
<223> OTHER INFORMATION: C4DS9 recombinant chimeric ADI protein

<400> SEQUENCE: 35

Met Ser Lys Ile Asn Val Tyr Ser Glu Ile Gly Glu Leu Lys Glu Val
 1               5                  10                  15
```

```
Leu Val His Thr Pro Gly Asp Glu Ile Arg Arg Ile Ser Pro Ser Arg
             20                  25                  30

Leu Asp Glu Leu Leu Phe Ser Ala Ile Leu Glu Pro Asn Glu Ala Ile
         35                  40                  45

Lys Glu His Lys Gly Phe Leu Lys Ile Leu Gln Asp Lys Gly Ile Lys
     50                  55                  60

Val Ile Gln Leu Ser Asp Leu Val Ala Glu Thr Tyr Lys His Tyr Ala
 65                  70                  75                  80

Ser Glu Ala Glu Lys Glu Ala Phe Ile Glu Lys Tyr Leu Asp Glu Ala
                 85                  90                  95

Thr Pro Val Leu Ser Lys Asp Met Arg Ala Lys Val Lys Asn Tyr Ile
             100                 105                 110

Leu Ser Met Gln Gly Glu Pro Val Lys Met Val Arg Thr Met Met Ala
         115                 120                 125

Gly Val Ser Lys Gln Glu Leu Asn Val Glu Ser Glu Val Glu Leu Ile
     130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                 165                 170                 175

Arg Glu Thr Ile Phe Ala Glu Phe Ile Phe Ala Thr His Pro Asp Tyr
             180                 185                 190

Lys Thr Thr Pro His Trp Phe Asp Arg Leu Asp Glu Gly Asn Ile Glu
         195                 200                 205

Gly Gly Asp Val Phe Ile Tyr Asn Lys Asp Thr Leu Val Ile Gly Val
     210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                 245                 250                 255

Pro Pro Met Pro Asn Leu Met His Leu Asp Thr Trp Leu Thr Met Val
             260                 265                 270

Asp Lys Asp Lys Phe Leu Tyr Ser Pro Asn Met Leu Ser Val Leu Lys
         275                 280                 285

Val Trp Glu Ile Asp Leu Ser Lys Glu Ile Glu Met Val Glu Thr Asn
     290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                 325                 330                 335

Glu Thr His Phe Asp Gly Thr Asn Tyr Leu Thr Ile Ala Pro Gly Val
             340                 345                 350

Val Val Gly Tyr Ser Arg Asn Ile Lys Thr Glu Ala Ala Leu Arg Ala
         355                 360                 365

Ala Gly Val Thr Val Leu Ser Phe Glu Gly Asn Gln Leu Ser Leu Gly
     370                 375                 380

Met Gly Ser Ala Arg Cys Met Ser Met Pro Leu Val Arg Glu Asp Val
385                 390                 395                 400

Lys

<210> SEQ ID NO 36
<211> LENGTH: 413
<212> TYPE: PRT
<213> ORGANISM: Artificial Sequence
```

-continued

```
<220> FEATURE:
<223> OTHER INFORMATION: C5DS1 recombinant chimeric ADI protein

<400> SEQUENCE: 36

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Leu Phe Val Ser Glu
        50                  55                  60

Leu Lys Ala Asn Asp Ile Asn Val Val Glu Leu Asp Glu Leu Val Ala
65                  70                  75                  80

Gln Thr Tyr Asp Gln Val Asp Gln Lys Ile Lys Asp Glu Phe Ile Asp
                85                  90                  95

Gln Trp Leu Gln Glu Ala Lys Pro Val Leu Asn Asp Gln Leu Lys Lys
            100                 105                 110

Leu Val Lys Asn Tyr Leu Leu Lys Ser Gln Lys Glu Phe Ser Thr Lys
        115                 120                 125

Lys Met Val Arg Ile Met Met Ala Gly Ile Asp Lys Lys Glu Ile Asn
130                 135                 140

Ile Asp Leu Asp Arg Asp Leu Val Val Asp Pro Met Pro Asn Leu Tyr
145                 150                 155                 160

Phe Thr Arg Asp Pro Phe Ala Ser Val Gly Asn Gly Val Thr Ile His
                165                 170                 175

Tyr Met Arg Tyr Lys Val Arg Gln Arg Glu Thr Leu Phe Ser Arg Phe
            180                 185                 190

Val Phe Ser Asn His Pro Lys Leu Val Asn Thr Pro Trp Tyr Tyr Asp
        195                 200                 205

Pro Ser Leu Lys Leu Ser Ile Glu Gly Gly Asp Val Phe Ile Tyr Asn
    210                 215                 220

Asn Asn Thr Leu Val Val Gly Val Ser Glu Arg Thr Asp Leu Glu Thr
225                 230                 235                 240

Val Thr Leu Leu Ala Lys Asn Ile Val Ala Asn Lys Glu Cys Glu Phe
                245                 250                 255

Lys Arg Ile Val Ala Ile Asn Val Pro Lys Trp Thr Asn Leu Met His
            260                 265                 270

Leu Asp Thr Trp Leu Thr Met Leu Asp Lys Asp Lys Phe Leu Tyr Ser
        275                 280                 285

Pro Ile Ala Asn Asp Val Phe Lys Phe Trp Asp Tyr Asp Leu Val Asn
    290                 295                 300

Gly Gly Glu Glu Pro Gln Pro Val Glu Asn Gly Leu Pro Leu Glu Gly
305                 310                 315                 320

Leu Leu Glu Ser Ile Ile Asn Lys Lys Pro Ile Leu Ile Pro Ile Ala
                325                 330                 335

Gly Glu Gly Ala Ser Gln Ile Asp Ile Glu Arg Glu Thr His Phe Asp
            340                 345                 350

Gly Thr Asn Tyr Leu Ala Ile Arg Pro Gly Val Val Ile Gly Tyr Ser
        355                 360                 365

Arg Asn Glu Lys Thr Asn Ala Ala Leu Glu Ala Ala Gly Ile Lys Val
    370                 375                 380

Leu Pro Phe His Gly Asn Gln Leu Ser Leu Gly Met Gly Asn Ala Arg
385                 390                 395                 400
```

Cys Met Ser Met Pro Leu Ser Arg Lys Asp Val Lys Trp
            405                 410

<210> SEQ ID NO 37
<211> LENGTH: 410
<212> TYPE: PRT
<213> ORGANISM: Artificial Sequence
<220> FEATURE:
<223> OTHER INFORMATION: C5DS2 recombinant chimeric ADI protein

<400> SEQUENCE: 37

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Leu Phe Val Ser Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Ile Tyr Asn Asn Asn Thr
    210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Glu
    290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

```
Tyr Leu Ala Ile Arg Pro Gly Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 38
<211> LENGTH: 410
<212> TYPE: PRT
<213> ORGANISM: Artificial Sequence
<220> FEATURE:
<223> OTHER INFORMATION: C5DS3 recombinant chimeric ADI protein

<400> SEQUENCE: 38

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Leu Phe Val Ser Glu
        50                  55                  60

Leu Lys Ala Asn Asp Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Ile Tyr Asn Asn Asn Thr
210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Glu
290                 295                 300
```

```
Glu Pro Gln Pro Val Glu Asn Gly Leu Pro Leu Gly Leu Leu Glu
305                 310                 315                 320

Ser Ile Ile Asn Lys Lys Pro Ile Leu Ile Pro Ile Ala Gly Glu Gly
            325                 330                 335

Ala Ser Gln Ile Asp Ile Glu Arg Glu Thr His Phe Asp Gly Thr Asn
                340                 345                 350

Tyr Leu Ala Ile Arg Pro Gly Val Val Ile Gly Tyr Ser Arg Asn Glu
                355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 39
<211> LENGTH: 412
<212> TYPE: PRT
<213> ORGANISM: Artificial Sequence
<220> FEATURE:
<223> OTHER INFORMATION: C5DS4 recombinant chimeric ADI protein

<400> SEQUENCE: 39

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Leu Phe Val Ser Glu
        50                  55                  60

Leu Lys Ala Asn Asp Ile Asn Val Val Glu Leu Ser Asp Leu Val Ala
65                  70                  75                  80

Glu Thr Tyr Thr Tyr His Ala Thr Gln Lys Glu Arg Glu Ala Phe Ile
                85                  90                  95

Glu Lys Trp Leu Asp Glu Ala Glu Pro Ala Leu Thr Lys Asp Leu Arg
                100                 105                 110

Ala Lys Val Lys Ser Tyr Val Leu Ser Lys Gly Thr Pro Val Ala
            115                 120                 125

Met Val Arg Thr Met Met Ala Gly Val Ser Lys Gln Glu Leu Asn Val
        130                 135                 140

Glu Ser Glu Thr Glu Leu Val Val Asp Pro Met Pro Asn Leu Tyr Phe
145                 150                 155                 160

Thr Arg Asp Pro Phe Ala Ser Val Gly Asn Gly Val Thr Ile His Tyr
                165                 170                 175

Met Arg Tyr Lys Val Arg Gln Arg Glu Thr Leu Phe Ser Arg Phe Val
                180                 185                 190

Phe Ser Asn His Pro Lys Leu Val Asn Thr Pro Trp Tyr Tyr Asp Pro
            195                 200                 205

Ser Leu Lys Leu Ser Ile Glu Gly Gly Asp Val Phe Ile Tyr Asn Asn
        210                 215                 220

Asn Thr Leu Val Val Gly Val Ser Glu Arg Thr Asp Leu Glu Thr Val
225                 230                 235                 240

Thr Leu Leu Ala Lys Asn Ile Val Ala Asn Lys Glu Cys Glu Phe Lys
                245                 250                 255
```

-continued

```
Arg Ile Val Ala Ile Asn Val Pro Lys Trp Thr Asn Leu Met His Leu
            260                 265                 270

Asp Thr Trp Leu Thr Met Leu Asp Lys Asp Lys Phe Leu Tyr Ser Pro
        275                 280                 285

Ile Ala Asn Asp Val Phe Lys Phe Trp Asp Tyr Asp Leu Val Asn Gly
    290                 295                 300

Gly Glu Glu Pro Gln Pro Val Glu Asn Gly Leu Pro Leu Gly Gly Leu
305                 310                 315                 320

Leu Glu Ser Ile Ile Asn Lys Lys Pro Ile Leu Ile Pro Ile Ala Gly
                325                 330                 335

Glu Gly Ala Ser Gln Ile Asp Ile Glu Arg Glu Thr His Phe Asp Gly
            340                 345                 350

Thr Asn Tyr Leu Ala Ile Arg Pro Gly Val Val Ile Gly Tyr Ser Arg
        355                 360                 365

Asn Glu Lys Thr Asn Ala Ala Leu Glu Ala Ala Gly Ile Lys Val Leu
    370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
                405                 410
```

<210> SEQ ID NO 40
<211> LENGTH: 410
<212> TYPE: PRT
<213> ORGANISM: Artificial Sequence
<220> FEATURE:
<223> OTHER INFORMATION: C5DS6 recombinant chimeric ADI protein

<400> SEQUENCE: 40

```
Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Leu Phe Val Ser Glu
    50                  55                  60

Leu Lys Ala Asn Asp Ile Asn Val Val Glu Leu Thr Asp Leu Val Ala
65                  70                  75                  80

Glu Thr Phe Asp Leu Ala Ser Lys Glu Glu Gln Glu Lys Leu Ile Glu
                85                  90                  95

Glu Phe Leu Glu Asp Ser Glu Pro Val Leu Ser Glu Ala His Lys Thr
            100                 105                 110

Ala Val Arg Lys Phe Leu Thr Ser Arg Lys Ser Thr Arg Glu Met Val
        115                 120                 125

Glu Phe Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205
```

-continued

```
Lys Leu Ser Ile Glu Gly Gly Asp Val Phe Ile Tyr Asn Asn Asn Thr
            210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Glu
            290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 41
<211> LENGTH: 410
<212> TYPE: PRT
<213> ORGANISM: Artificial Sequence
<220> FEATURE:
<223> OTHER INFORMATION: C5DS7 recombinant chimeric ADI protein

<400> SEQUENCE: 41

Met Ser Val Phe Asp Ser Lys Phe Asn Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Leu Phe Val Ser Glu
    50                  55                  60

Leu Lys Ala Asn Asp Ile Asn Val Val Glu Leu Thr Asp Leu Val Ser
65                  70                  75                  80

Glu Thr Tyr Asp Met Val Ser Lys Glu Lys Gln Glu Lys Leu Ile Glu
                85                  90                  95

Glu Phe Leu Glu Asp Ser Glu Pro Val Leu Ser Glu His Lys Gly
            100                 105                 110

Leu Val Arg Lys Phe Leu Lys Ser Leu Lys Ser Ser Lys Glu Leu Ile
        115                 120                 125

Gln Tyr Met Met Ala Gly Ile Thr Lys His Asp Leu Asn Ile Glu Ala
    130                 135                 140

Asp His Glu Leu Ile Val Asp Pro Met Pro Asn Leu Tyr Phe Thr Arg
145                 150                 155                 160
```

-continued

```
Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Ile Tyr Asn Asn Asn Thr
    210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Glu
    290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 42
<211> LENGTH: 413
<212> TYPE: PRT
<213> ORGANISM: Artificial Sequence
<220> FEATURE:
<223> OTHER INFORMATION: C6DS1 recombinant chimeric ADI protein

<400> SEQUENCE: 42

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60

Leu Lys Asp Asn Gly Ile Asn Val Glu Leu Asp Glu Leu Val Ala
65                  70                  75                  80

Gln Thr Tyr Asp Gln Val Asp Gln Lys Ile Lys Asp Glu Phe Ile Asp
                85                  90                  95

Gln Trp Leu Gln Glu Ala Lys Pro Val Leu Asn Asp Gln Leu Lys Lys
            100                 105                 110
```

```
Leu Val Lys Asn Tyr Leu Leu Lys Ser Gln Lys Glu Phe Ser Thr Lys
            115                 120                 125

Lys Met Val Arg Ile Met Met Ala Gly Ile Asp Lys Lys Glu Ile Asn
        130                 135                 140

Ile Asp Leu Asp Arg Asp Leu Val Val Asp Pro Met Pro Asn Leu Tyr
145                 150                 155                 160

Phe Thr Arg Asp Pro Phe Ala Ser Val Gly Asn Gly Val Thr Ile His
                165                 170                 175

Tyr Met Arg Tyr Lys Val Arg Gln Arg Glu Thr Leu Phe Ser Arg Phe
            180                 185                 190

Val Phe Ser Asn His Pro Lys Leu Val Lys Thr Pro Trp Tyr Tyr Asp
        195                 200                 205

Pro Ala Met Lys Met Ser Ile Glu Gly Gly Asp Val Phe Ile Tyr Asn
    210                 215                 220

Asn Asp Thr Leu Val Val Gly Val Ser Glu Arg Thr Asp Leu Glu Thr
225                 230                 235                 240

Ile Thr Leu Leu Ala Lys Asn Ile Lys Ala Asn Lys Glu Val Glu Phe
                245                 250                 255

Lys Arg Ile Val Ala Ile Asn Val Pro Lys Trp Thr Asn Leu Met His
            260                 265                 270

Leu Asp Thr Trp Leu Thr Met Leu Asp Lys Asp Lys Phe Leu Tyr Ser
        275                 280                 285

Pro Ile Ala Asn Asp Val Phe Lys Phe Trp Asp Tyr Asp Leu Val Asn
    290                 295                 300

Gly Gly Ala Glu Pro Gln Pro Lys Glu Asn Gly Leu Pro Leu Glu Gly
305                 310                 315                 320

Leu Leu Gln Ser Ile Ile Asn Lys Lys Pro Val Leu Ile Pro Ile Ala
                325                 330                 335

Gly Asn Asn Ala Ser His Ile Asp Ile Glu Arg Glu Thr His Phe Asp
            340                 345                 350

Gly Thr Asn Tyr Leu Ala Ile Lys Pro Gly Val Val Ile Gly Tyr Ala
        355                 360                 365

Arg Asn Glu Lys Thr Asn Ala Ala Leu Ala Ala Ala Gly Ile Lys Val
    370                 375                 380

Leu Pro Phe His Gly Asn Gln Leu Ser Leu Gly Met Gly Asn Ala Arg
385                 390                 395                 400

Cys Met Ser Met Pro Leu Ser Arg Lys Asp Val Lys Trp
                405                 410

<210> SEQ ID NO 43
<211> LENGTH: 410
<212> TYPE: PRT
<213> ORGANISM: Artificial Sequence
<220> FEATURE:
<223> OTHER INFORMATION: C6DS2 recombinant chimeric ADI protein

<400> SEQUENCE: 43

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60
```

Leu Lys Asp Asn Gly Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
            85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
            115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
            180                 185                 190

Asn His Pro Lys Leu Val Lys Thr Pro Trp Tyr Tyr Asp Pro Ala Met
            195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ala
290                 295                 300

Glu Pro Gln Pro Lys Glu Asn Gly Leu Pro Leu Glu Gly Leu Leu Gln
305                 310                 315                 320

Ser Ile Ile Asn Lys Lys Pro Val Leu Ile Pro Ile Ala Gly Asn Asn
            325                 330                 335

Ala Ser His Ile Asp Ile Glu Arg Glu Thr His Phe Asp Gly Thr Asn
            340                 345                 350

Tyr Leu Ala Ile Lys Pro Gly Val Val Ile Gly Tyr Ala Arg Asn Glu
            355                 360                 365

Lys Thr Asn Ala Ala Leu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

<210> SEQ ID NO 44
<211> LENGTH: 410
<212> TYPE: PRT
<213> ORGANISM: Artificial Sequence
<220> FEATURE:
<223> OTHER INFORMATION: C6DS3 recombinant chimeric ADI protein

<400> SEQUENCE: 44

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
           20                  25                  30

Asp Tyr Ile Thr Pro Ala Arg Leu Asp Glu Leu Leu Phe Ser Ala Ile
               35                  40                  45

Leu Glu Ser His Asp Ala Arg Lys Glu His Gln Ser Phe Val Lys Gln
 50                  55                  60

Leu Lys Asp Asn Gly Ile Asn Val Val Glu Leu Val Asp Leu Ile Val
 65                  70                  75                  80

Glu Thr Tyr Asp Leu Ala Ser Lys Glu Ala Lys Glu Lys Leu Leu Glu
                 85                  90                  95

Glu Phe Leu Asp Asp Ser Val Pro Val Leu Ser Asp Glu His Arg Ala
                100                 105                 110

Thr Val Lys Lys Phe Leu Gln Ser Gln Lys Ser Thr Arg Ser Leu Val
                115                 120                 125

Glu Tyr Met Ile Ala Gly Ile Thr Lys His Asp Leu Lys Ile Glu Ser
130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
                180                 185                 190

Asn His Pro Lys Leu Val Lys Thr Pro Trp Tyr Tyr Asp Pro Ala Met
                195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
                275                 280                 285

Asn Asp Val Phe Lys Phe Trp Asp Tyr Asp Leu Val Asn Gly Gly Ala
290                 295                 300

Glu Pro Gln Pro Lys Glu Asn Gly Leu Pro Leu Glu Gly Leu Leu Gln
305                 310                 315                 320

Ser Ile Ile Asn Lys Lys Pro Val Leu Ile Pro Ile Ala Gly Asn Asn
                325                 330                 335

Ala Ser His Ile Asp Ile Glu Arg Glu Thr His Phe Asp Gly Thr Asn
                340                 345                 350

Tyr Leu Ala Ile Lys Pro Gly Val Val Ile Gly Tyr Ala Arg Asn Glu
                355                 360                 365

Lys Thr Asn Ala Ala Leu Ala Ala Gly Ile Lys Val Leu Pro Phe
                370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 45
<211> LENGTH: 412

```
<212> TYPE: PRT
<213> ORGANISM: Artificial Sequence
<220> FEATURE:
<223> OTHER INFORMATION: C6DS4 recombinant chimeric ADI protein

<400> SEQUENCE: 45
```

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60

Leu Lys Asp Asn Gly Ile Asn Val Val Glu Leu Ser Asp Leu Val Ala
65                  70                  75                  80

Glu Thr Tyr Thr Tyr His Ala Thr Gln Lys Glu Arg Glu Ala Phe Ile
                85                  90                  95

Glu Lys Trp Leu Asp Glu Ala Glu Pro Ala Leu Thr Lys Asp Leu Arg
            100                 105                 110

Ala Lys Val Lys Ser Tyr Val Leu Ser Lys Gly Thr Pro Val Ala
        115                 120                 125

Met Val Arg Thr Met Met Ala Gly Val Ser Lys Gln Glu Leu Asn Val
    130                 135                 140

Glu Ser Glu Thr Glu Leu Val Val Asp Pro Met Pro Asn Leu Tyr Phe
145                 150                 155                 160

Thr Arg Asp Pro Phe Ala Ser Val Gly Asn Gly Val Thr Ile His Tyr
                165                 170                 175

Met Arg Tyr Lys Val Arg Gln Arg Glu Thr Leu Phe Ser Arg Phe Val
            180                 185                 190

Phe Ser Asn His Pro Lys Leu Val Lys Thr Pro Trp Tyr Tyr Asp Pro
        195                 200                 205

Ala Met Lys Met Ser Ile Glu Gly Gly Asp Val Phe Ile Tyr Asn Asn
    210                 215                 220

Asp Thr Leu Val Val Gly Val Ser Glu Arg Thr Asp Leu Glu Thr Ile
225                 230                 235                 240

Thr Leu Leu Ala Lys Asn Ile Lys Ala Asn Lys Glu Val Glu Phe Lys
                245                 250                 255

Arg Ile Val Ala Ile Asn Val Pro Lys Trp Thr Asn Leu Met His Leu
            260                 265                 270

Asp Thr Trp Leu Thr Met Leu Asp Lys Asp Lys Phe Leu Tyr Ser Pro
        275                 280                 285

Ile Ala Asn Asp Val Phe Lys Phe Trp Asp Tyr Asp Leu Val Asn Gly
    290                 295                 300

Gly Ala Glu Pro Gln Pro Lys Glu Asn Gly Leu Pro Leu Glu Gly Leu
305                 310                 315                 320

Leu Gln Ser Ile Ile Asn Lys Lys Pro Val Leu Ile Pro Ile Ala Gly
                325                 330                 335

Asn Asn Ala Ser His Ile Asp Ile Glu Arg Glu Thr His Phe Asp Gly
            340                 345                 350

Thr Asn Tyr Leu Ala Ile Lys Pro Gly Val Val Ile Gly Tyr Ala Arg
        355                 360                 365

Asn Glu Lys Thr Asn Ala Ala Leu Ala Ala Ala Gly Ile Lys Val Leu
    370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
            405                 410

<210> SEQ ID NO 46
<211> LENGTH: 410
<212> TYPE: PRT
<213> ORGANISM: Artificial Sequence
<220> FEATURE:
<223> OTHER INFORMATION: C6DS5 recombinant chimeric ADI protein

<400> SEQUENCE: 46

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60

Leu Lys Asp Asn Gly Ile Asn Val Val Glu Leu Thr Asp Leu Val Thr
65                  70                  75                  80

Glu Thr Tyr Asp Leu Ala Ser Gln Glu Ala Lys Asp Asn Leu Ile Glu
                85                  90                  95

Glu Phe Leu Glu Asp Ser Glu Pro Val Leu Thr Glu Glu Leu Lys Ser
            100                 105                 110

Val Val Arg Thr Tyr Leu Lys Ser Ile Lys Ser Thr Arg Glu Leu Ile
        115                 120                 125

Gln Met Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Lys Thr Pro Trp Tyr Tyr Asp Pro Ala Met
        195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Lys Glu Asn Gly Leu Pro Leu Glu Gly Leu Leu Gln
305                 310                 315                 320

Ser Ile Ile Asn Lys Lys Pro Val Leu Ile Pro Ile Ala Gly Asn Asn
                325                 330                 335

```
Ala Ser His Ile Asp Ile Glu Arg Glu Thr His Phe Asp Gly Thr Asn
            340                 345                 350

Tyr Leu Ala Ile Lys Pro Gly Val Val Ile Gly Tyr Ala Arg Asn Glu
        355                 360                 365

Lys Thr Asn Ala Ala Leu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 47
<211> LENGTH: 410
<212> TYPE: PRT
<213> ORGANISM: Artificial Sequence
<220> FEATURE:
<223> OTHER INFORMATION: C6DS7 recombinant chimeric ADI protein

<400> SEQUENCE: 47

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Gln
    50                  55                  60

Leu Lys Asp Asn Gly Ile Asn Val Val Glu Leu Thr Asp Leu Val Ser
65                  70                  75                  80

Glu Thr Tyr Asp Met Val Ser Lys Glu Lys Gln Glu Lys Leu Ile Glu
                85                  90                  95

Glu Phe Leu Glu Asp Ser Glu Pro Val Leu Ser Glu His Lys Gly
            100                 105                 110

Leu Val Arg Lys Phe Leu Lys Ser Leu Lys Ser Ser Lys Glu Leu Ile
        115                 120                 125

Gln Tyr Met Met Ala Gly Ile Thr Lys His Asp Leu Asn Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Lys Thr Pro Trp Tyr Tyr Asp Pro Ala Met
        195                 200                 205

Lys Met Ser Ile Glu Gly Gly Asp Val Phe Ile Tyr Asn Asn Asp Thr
    210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285
```

```
Asn Asp Val Phe Lys Phe Trp Asp Tyr Asp Leu Val Asn Gly Gly Ala
    290                 295                 300
Glu Pro Gln Pro Lys Glu Asn Gly Leu Pro Leu Glu Gly Leu Leu Gln
305                 310                 315                 320
Ser Ile Ile Asn Lys Lys Pro Val Leu Ile Pro Ile Ala Gly Asn Asn
                325                 330                 335
Ala Ser His Ile Asp Ile Glu Arg Glu Thr His Phe Asp Gly Thr Asn
                340                 345                 350
Tyr Leu Ala Ile Lys Pro Gly Val Val Ile Gly Tyr Ala Arg Asn Glu
                355                 360                 365
Lys Thr Asn Ala Ala Leu Ala Ala Gly Ile Lys Val Leu Pro Phe
370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 48
<211> LENGTH: 413
<212> TYPE: PRT
<213> ORGANISM: Artificial Sequence
<220> FEATURE:
<223> OTHER INFORMATION: C7DS1 recombinant chimeric ADI protein

<400> SEQUENCE: 48

Met Ser Val Phe Asp Ser Lys Phe Asn Gly Ile His Val Tyr Ser Glu
1               5                   10                  15
Ile Gly Glu Leu Gln Thr Val Leu His Gly Pro Gly Arg Glu Ile
                20                  25                  30
Glu Tyr Ile Thr Pro Ala Arg Leu Asp Glu Leu Leu Phe Ser Ala Ile
                35                  40                  45
Leu Glu Ser His Asp Ala Arg Lys Glu His Gln Glu Phe Val Ala Glu
                50                  55                  60
Leu Lys Lys Asn Asn Ile Asn Val Val Glu Leu Asp Glu Leu Val Ala
65                  70                  75                  80
Gln Thr Tyr Asp Gln Val Asp Gln Lys Ile Lys Asp Glu Phe Ile Asp
                85                  90                  95
Gln Trp Leu Gln Glu Ala Lys Pro Val Leu Asn Asp Gln Leu Lys Lys
                100                 105                 110
Leu Val Lys Asn Tyr Leu Leu Lys Ser Gln Lys Glu Phe Ser Thr Lys
                115                 120                 125
Lys Met Val Arg Ile Met Met Ala Gly Ile Asp Lys Lys Glu Ile Asn
                130                 135                 140
Ile Asp Leu Asp Arg Asp Leu Val Asp Pro Met Pro Asn Leu Tyr
145                 150                 155                 160
Phe Thr Arg Asp Pro Phe Ala Ser Val Gly Asn Gly Val Thr Ile His
                165                 170                 175
Tyr Met Arg Tyr Lys Val Arg Gln Arg Glu Thr Leu Phe Ser Arg Phe
                180                 185                 190
Ile Phe Ala Asn His Pro Lys Leu Met Asn Thr Pro Leu Tyr Tyr Asn
                195                 200                 205
Pro Asp Met Lys Leu Ser Ile Glu Gly Gly Asp Val Phe Val Tyr Asn
                210                 215                 220
Asn Glu Thr Leu Val Val Gly Val Ser Glu Arg Thr Asp Leu Asp Thr
225                 230                 235                 240
```

-continued

```
Ile Thr Leu Leu Ala Lys Asn Ile Lys Ala Asn Lys Glu Arg Glu Phe
            245                 250                 255
Lys Arg Ile Val Ala Ile Asn Val Pro Lys Trp Thr Asn Leu Met His
        260                 265                 270
Leu Asp Thr Trp Leu Thr Met Leu Asp Lys Asp Lys Phe Leu Tyr Ser
    275                 280                 285
Pro Ile Ala Asn Asp Val Phe Lys Phe Trp Asp Tyr Asp Leu Val Asn
290                 295                 300
Gly Gly Asp Glu Pro Gln Pro Lys Val Asn Gly Leu Pro Leu Glu Lys
305                 310                 315                 320
Leu Leu Glu Ser Ile Ile Asn Lys Lys Pro Ile Leu Ile Pro Ile Ala
                325                 330                 335
Gly Thr Ser Ala Ser Asn Ile Asp Val Glu Arg Glu Thr His Phe Asp
            340                 345                 350
Gly Thr Asn Tyr Leu Ala Ile Ala Pro Gly Val Val Ile Gly Tyr Ser
        355                 360                 365
Arg Asn Val Lys Thr Asn Glu Ala Leu Glu Ala Ala Gly Ile Lys Val
    370                 375                 380
Leu Pro Phe Lys Gly Asn Gln Leu Ser Leu Gly Met Gly Asn Ala Arg
385                 390                 395                 400
Cys Met Ser Met Pro Leu Ser Arg Lys Asp Val Lys Trp
                405                 410

<210> SEQ ID NO 49
<211> LENGTH: 410
<212> TYPE: PRT
<213> ORGANISM: Artificial Sequence
<220> FEATURE:
<223> OTHER INFORMATION: C7DS2 recombinant chimeric ADI protein

<400> SEQUENCE: 49

Met Ser Val Phe Asp Ser Lys Phe Asn Gly Ile His Val Tyr Ser Glu
1               5                   10                  15
Ile Gly Glu Leu Gln Thr Val Leu Val His Glu Pro Gly Arg Glu Ile
            20                  25                  30
Glu Tyr Ile Thr Pro Ala Arg Leu Asp Glu Leu Leu Phe Ser Ala Ile
        35                  40                  45
Leu Glu Ser His Asp Ala Arg Lys Glu His Gln Glu Phe Val Ala Glu
    50                  55                  60
Leu Lys Lys Asn Asn Ile Asn Val Val Glu Leu Ile Asp Leu Val Ala
65                  70                  75                  80
Glu Thr Tyr Asp Leu Ala Ser Gln Glu Ala Lys Asp Lys Leu Ile Glu
                85                  90                  95
Glu Phe Leu Glu Asp Ser Glu Pro Val Leu Ser Glu Glu His Lys Val
            100                 105                 110
Val Val Arg Asn Phe Leu Lys Ala Lys Lys Thr Ser Arg Glu Leu Val
        115                 120                 125
Glu Ile Met Met Ala Gly Ile Thr Lys Tyr Asp Leu Gly Ile Glu Ala
    130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Ile Phe Ala
            180                 185                 190
```

```
Asn His Pro Lys Leu Met Asn Thr Pro Leu Tyr Tyr Asn Pro Asp Met
        195                 200                 205

Lys Leu Ser Ile Glu Gly Gly Asp Val Phe Val Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
            245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
        290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
            325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
        370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 50
<211> LENGTH: 410
<212> TYPE: PRT
<213> ORGANISM: Artificial Sequence
<220> FEATURE:
<223> OTHER INFORMATION: C7DS3 recombinant chimeric ADI protein

<400> SEQUENCE: 50

Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
                20                  25                  30

Glu Tyr Ile Thr Pro Ala Arg Leu Asp Glu Leu Leu Phe Ser Ala Ile
            35                  40                  45

Leu Glu Ser His Asp Ala Arg Lys Glu His Gln Glu Phe Val Ala Glu
        50                  55                  60

Leu Lys Lys Asn Asn Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Thr Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
    130                 135                 140
```

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Ile Phe Ala
        180                 185                 190

Asn His Pro Lys Leu Met Asn Thr Pro Leu Tyr Tyr Asn Pro Asp Met
    195                 200                 205

Lys Leu Ser Ile Glu Gly Gly Asp Val Phe Val Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
    370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 51
<211> LENGTH: 412
<212> TYPE: PRT
<213> ORGANISM: Artificial Sequence
<220> FEATURE:
<223> OTHER INFORMATION: C7DS4 recombinant chimeric ADI protein

<400> SEQUENCE: 51

Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
            20                  25                  30

Glu Tyr Ile Thr Pro Ala Arg Leu Asp Glu Leu Leu Phe Ser Ala Ile
        35                  40                  45

Leu Glu Ser His Asp Ala Arg Lys Glu His Gln Glu Phe Val Ala Glu
    50                  55                  60

Leu Lys Lys Asn Asn Ile Asn Val Val Glu Leu Ser Asp Leu Val Ala
65                  70                  75                  80

Glu Thr Tyr Thr Tyr His Ala Thr Gln Lys Glu Arg Glu Ala Phe Ile
                85                  90                  95

```
Glu Lys Trp Leu Asp Glu Ala Glu Pro Ala Leu Thr Lys Asp Leu Arg
            100                 105                 110

Ala Lys Val Lys Ser Tyr Val Leu Ser Lys Glu Gly Thr Pro Val Ala
            115                 120                 125

Met Val Arg Thr Met Met Ala Gly Val Ser Lys Gln Glu Leu Asn Val
        130                 135                 140

Glu Ser Glu Thr Glu Leu Val Val Asp Pro Met Pro Asn Leu Tyr Phe
145                 150                 155                 160

Thr Arg Asp Pro Phe Ala Ser Val Gly Asn Gly Val Thr Ile His Tyr
                165                 170                 175

Met Arg Tyr Lys Val Arg Gln Arg Glu Thr Leu Phe Ser Arg Phe Ile
            180                 185                 190

Phe Ala Asn His Pro Lys Leu Met Asn Thr Pro Leu Tyr Tyr Asn Pro
        195                 200                 205

Asp Met Lys Leu Ser Ile Glu Gly Gly Asp Val Phe Val Tyr Asn Asn
210                 215                 220

Glu Thr Leu Val Val Gly Val Ser Glu Arg Thr Asp Leu Asp Thr Ile
225                 230                 235                 240

Thr Leu Leu Ala Lys Asn Ile Lys Ala Asn Lys Glu Arg Glu Phe Lys
                245                 250                 255

Arg Ile Val Ala Ile Asn Val Pro Lys Trp Thr Asn Leu Met His Leu
            260                 265                 270

Asp Thr Trp Leu Thr Met Leu Asp Lys Asp Lys Phe Leu Tyr Ser Pro
        275                 280                 285

Ile Ala Asn Asp Val Phe Lys Phe Trp Asp Tyr Asp Leu Val Asn Gly
290                 295                 300

Gly Asp Glu Pro Gln Pro Lys Val Asn Gly Leu Pro Leu Glu Lys Leu
305                 310                 315                 320

Leu Glu Ser Ile Ile Asn Lys Lys Pro Ile Leu Ile Pro Ile Ala Gly
                325                 330                 335

Thr Ser Ala Ser Asn Ile Asp Val Glu Arg Glu Thr His Phe Asp Gly
            340                 345                 350

Thr Asn Tyr Leu Ala Ile Ala Pro Gly Val Val Ile Gly Tyr Ser Arg
        355                 360                 365

Asn Val Lys Thr Asn Glu Ala Leu Glu Ala Ala Gly Ile Lys Val Leu
370                 375                 380

Pro Phe Lys Gly Asn Gln Leu Ser Leu Gly Met Gly Asn Ala Arg Cys
385                 390                 395                 400

Met Ser Met Pro Leu Ser Arg Lys Asp Val Lys Trp
                405                 410

<210> SEQ ID NO 52
<211> LENGTH: 410
<212> TYPE: PRT
<213> ORGANISM: Artificial Sequence
<220> FEATURE:
<223> OTHER INFORMATION: C7DS5 recombinant chimeric ADI protein

<400> SEQUENCE: 52

Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
            20                  25                  30

Glu Tyr Ile Thr Pro Ala Arg Leu Asp Glu Leu Leu Phe Ser Ala Ile
        35                  40                  45
```

```
Leu Glu Ser His Asp Ala Arg Lys Glu His Gln Glu Phe Val Ala Glu
 50                  55                  60
Leu Lys Lys Asn Asn Ile Asn Val Val Glu Leu Thr Asp Leu Val Thr
 65                  70                  75                  80
Glu Thr Tyr Asp Leu Ala Ser Gln Glu Ala Lys Asp Asn Leu Ile Glu
                 85                  90                  95
Glu Phe Leu Glu Asp Ser Glu Pro Val Leu Thr Glu Glu Leu Lys Ser
            100                 105                 110
Val Val Arg Thr Tyr Leu Lys Ser Ile Lys Ser Thr Arg Glu Leu Ile
            115                 120                 125
Gln Met Met Met Ala Gly Ile Thr Lys Tyr Asp Leu Gly Ile Glu Ala
130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Ile Phe Ala
            180                 185                 190
Asn His Pro Lys Leu Met Asn Thr Pro Leu Tyr Tyr Asn Pro Asp Met
            195                 200                 205
Lys Leu Ser Ile Glu Gly Gly Asp Val Phe Val Tyr Asn Asn Glu Thr
210                 215                 220
Leu Val Val Gly Val Ser Glu Arg Thr Asp Leu Asp Thr Ile Thr Leu
225                 230                 235                 240
Leu Ala Lys Asn Ile Lys Ala Asn Lys Glu Arg Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Lys Asp Lys Phe Leu Tyr Ser Pro Ile Ala
            275                 280                 285
Asn Asp Val Phe Lys Phe Trp Asp Tyr Asp Leu Val Asn Gly Gly Asp
            290                 295                 300
Glu Pro Gln Pro Lys Val Asn Gly Leu Pro Leu Glu Lys Leu Leu Glu
305                 310                 315                 320
Ser Ile Ile Asn Lys Lys Pro Ile Leu Ile Pro Ile Ala Gly Thr Ser
                325                 330                 335
Ala Ser Asn Ile Asp Val Glu Arg Glu Thr His Phe Asp Gly Thr Asn
            340                 345                 350
Tyr Leu Ala Ile Ala Pro Gly Val Val Ile Gly Tyr Ser Arg Asn Val
            355                 360                 365
Lys Thr Asn Glu Ala Leu Glu Ala Ala Gly Ile Lys Val Leu Pro Phe
370                 375                 380
Lys Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 53
<211> LENGTH: 410
<212> TYPE: PRT
<213> ORGANISM: Artificial Sequence
<220> FEATURE:
<223> OTHER INFORMATION: C7DS6 recombinant chimeric ADI protein

<400> SEQUENCE: 53
```

```
Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
            20                  25                  30

Glu Tyr Ile Thr Pro Ala Arg Leu Asp Glu Leu Leu Phe Ser Ala Ile
                35                  40                  45

Leu Glu Ser His Asp Ala Arg Lys Glu His Gln Glu Phe Val Ala Glu
        50                  55                  60

Leu Lys Lys Asn Asn Ile Asn Val Val Glu Leu Thr Asp Leu Val Ala
65                  70                  75                  80

Glu Thr Phe Asp Leu Ala Ser Lys Glu Gln Glu Lys Leu Ile Glu
                85                  90                  95

Glu Phe Leu Glu Asp Ser Glu Pro Val Leu Ser Glu Ala His Lys Thr
                100                 105                 110

Ala Val Arg Lys Phe Leu Thr Ser Arg Lys Ser Thr Arg Glu Met Val
            115                 120                 125

Glu Phe Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ala
            180                 185                 190

Asn His Pro Lys Leu Met Asn Thr Pro Leu Tyr Tyr Asn Pro Asp Met
        195                 200                 205

Lys Leu Ser Ile Glu Gly Gly Asp Val Phe Val Tyr Asn Asn Glu Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
        290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```

```
<210> SEQ ID NO 54
<211> LENGTH: 399
<212> TYPE: PRT
<213> ORGANISM: Artificial Sequence
<220> FEATURE:
<223> OTHER INFORMATION: C8DS3 recombinant chimeric ADI protein

<400> SEQUENCE: 54

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
                20                  25                  30

Leu Glu Glu Leu Leu Phe Ser Ala Val Leu Glu Pro Asn Ala Ala Ile
            35                  40                  45

Glu Glu His Lys Arg Phe Val Lys Leu Leu Glu Asp Arg Gly Ile Gln
        50                  55                  60

Ala Ile Gln Leu Val Asp Leu Ile Val Glu Thr Tyr Asp Leu Ala Ser
65                  70                  75                  80

Lys Glu Ala Lys Glu Lys Leu Leu Glu Glu Phe Leu Asp Asp Ser Val
                85                  90                  95

Pro Val Leu Ser Asp Glu His Arg Ala Thr Val Lys Lys Phe Leu Gln
                100                 105                 110

Ser Gln Lys Ser Thr Arg Ser Leu Val Glu Tyr Met Ile Ala Gly Ile
            115                 120                 125

Thr Lys His Asp Leu Lys Ile Glu Ser Asp Leu Glu Leu Ile Val Asp
        130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Val Arg Lys Arg Glu
                165                 170                 175

Thr Ile Phe Ala Glu Phe Ile Phe Ala Ile His Pro Glu Tyr Lys Glu
            180                 185                 190

Thr Pro His Trp Phe Asp Arg Leu Asp His Gly Ser Ile Glu Gly Gly
        195                 200                 205

Asp Val Phe Val Tyr Asn Lys Asp Thr Leu Val Ile Gly Val Ser Glu
210                 215                 220

Arg Thr Asn Lys Glu Ala Ile Ile Thr Ile Ala Lys His Ile Gln Asp
225                 230                 235                 240

Asn Lys Glu Ala Glu Phe Lys Lys Ile Val Ala Ile Asn Val Pro Pro
                245                 250                 255

Met Pro Asn Leu Met His Leu Asp Thr Trp Leu Thr Met Val Asp Lys
            260                 265                 270

Asn Lys Phe Ile Tyr Ser Pro Asn Met Leu Ser Val Leu Lys Ile Trp
        275                 280                 285

Glu Ile Asp Leu Ala Lys Pro Ile Glu Met Val Glu Ser Asn Lys Ser
290                 295                 300

Leu Thr Glu Val Leu Glu Ser Ile Ile Gly Glu Lys Pro Ile Leu Ile
305                 310                 315                 320

Pro Ile Ala Gly Glu Gly Ala Ser Gln Leu Asp Ile Asp Ile Glu Thr
                325                 330                 335

His Phe Asp Gly Thr Asn Tyr Leu Thr Ile Ala Pro Gly Val Val Val
            340                 345                 350

Gly Tyr Ser Arg Asn Glu Lys Thr Glu Lys Ala Leu Lys Ala Ala Gly
        355                 360                 365

Ile Thr Val Leu Ser Phe Glu Gly Asn Gln Leu Ser Leu Gly Met Gly
```

```
                     370                 375                 380
Ser Ala Arg Cys Met Ser Met Pro Leu Val Arg Glu Asp Val Lys
385                 390                 395
```

<210> SEQ ID NO 55
<211> LENGTH: 401
<212> TYPE: PRT
<213> ORGANISM: Artificial Sequence
<220> FEATURE:
<223> OTHER INFORMATION: C8DS4 recombinant chimeric ADI protein

<400> SEQUENCE: 55

```
Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
                20                  25                  30

Leu Glu Glu Leu Leu Phe Ser Ala Val Leu Glu Pro Asn Ala Ala Ile
            35                  40                  45

Glu Glu His Lys Arg Phe Val Lys Leu Leu Glu Asp Arg Gly Ile Gln
        50                  55                  60

Ala Ile Gln Leu Ser Asp Leu Val Ala Glu Thr Tyr Thr Tyr His Ala
65                  70                  75                  80

Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
            100                 105                 110

Leu Ser Lys Glu Gly Thr Pro Val Ala Met Val Arg Thr Met Met Ala
        115                 120                 125

Gly Val Ser Lys Gln Glu Leu Asn Val Glu Ser Glu Thr Glu Leu Val
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ala Ile His Pro Glu Tyr
            180                 185                 190

Lys Glu Thr Pro His Trp Phe Asp Arg Leu Asp His Gly Ser Ile Glu
        195                 200                 205

Gly Gly Asp Val Phe Val Tyr Asn Lys Asp Thr Leu Val Ile Gly Val
210                 215                 220

Ser Glu Arg Thr Asn Lys Glu Ala Ile Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Ile Tyr Ser Pro Asn Met Leu Ser Val Leu Lys
        275                 280                 285

Ile Trp Glu Ile Asp Leu Ala Lys Pro Ile Glu Met Val Glu Ser Asn
290                 295                 300

Lys Ser Leu Thr Glu Val Leu Glu Ser Ile Ile Gly Glu Lys Pro Ile
305                 310                 315                 320

Leu Ile Pro Ile Ala Gly Glu Gly Ala Ser Gln Leu Asp Ile Asp Ile
                325                 330                 335

Glu Thr His Phe Asp Gly Thr Asn Tyr Leu Thr Ile Ala Pro Gly Val
```

```
            340                 345                 350
Val Val Gly Tyr Ser Arg Asn Glu Lys Thr Glu Lys Ala Leu Lys Ala
        355                 360                 365

Ala Gly Ile Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400

Lys

<210> SEQ ID NO 56
<211> LENGTH: 401
<212> TYPE: PRT
<213> ORGANISM: Artificial Sequence
<220> FEATURE:
<223> OTHER INFORMATION: C8DS9 recombinant chimeric ADI protein

<400> SEQUENCE: 56

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile
        35                  40                  45

Glu Glu His Lys Arg Phe Val Lys Leu Leu Glu Asp Arg Gly Ile Gln
50                  55                  60

Ala Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
            100                 105                 110

Leu Ser Met Gln Gly Glu Pro Val Lys Met Val Arg Thr Met Met Ala
        115                 120                 125

Gly Val Ser Lys Gln Glu Leu Asn Val Glu Ser Glu Val Glu Leu Ile
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ala Ile His Pro Glu Tyr
            180                 185                 190

Lys Glu Thr Pro His Trp Phe Asp Arg Leu Asp His Gly Ser Ile Glu
        195                 200                 205

Gly Gly Asp Val Phe Val Tyr Asn Lys Asp Thr Leu Val Ile Gly Val
210                 215                 220

Ser Glu Arg Thr Asn Lys Glu Ala Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Ile Tyr Ser Pro Asn Met Leu Ser Val Leu Lys
        275                 280                 285

Ile Trp Glu Ile Asp Leu Ala Lys Pro Ile Glu Met Val Glu Ser Asn
290                 295                 300
```

```
Lys Ser Leu Thr Glu Val Leu Glu Ser Ile Ile Gly Glu Lys Pro Ile
305                 310                 315                 320

Leu Ile Pro Ile Ala Gly Glu Gly Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Glu Lys Thr Glu Lys Ala Leu Lys Ala
        355                 360                 365

Ala Gly Ile Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 57
<211> LENGTH: 399
<212> TYPE: PRT
<213> ORGANISM: Artificial Sequence
<220> FEATURE:
<223> OTHER INFORMATION: C9DS3 recombinant chimeric ADI protein

<400> SEQUENCE: 57

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
                20                  25                  30

Leu Asp Glu Leu Leu Phe Ser Ala Ile Leu Glu Pro Ser Ala Ala Ile
            35                  40                  45

Gln Glu His Lys Ser Phe Leu Lys Ile Leu Gln Asp Arg Gly Ile Lys
        50                  55                  60

Thr Ile Gln Leu Val Asp Leu Ile Val Glu Thr Tyr Asp Leu Ala Ser
65                  70                  75                  80

Lys Glu Ala Lys Glu Lys Leu Leu Glu Phe Leu Asp Asp Ser Val
                85                  90                  95

Pro Val Leu Ser Asp Glu His Arg Ala Thr Val Lys Lys Phe Leu Gln
                100                 105                 110

Ser Gln Lys Ser Thr Arg Ser Leu Val Glu Tyr Met Ile Ala Gly Ile
                115                 120                 125

Thr Lys His Asp Leu Lys Ile Glu Ser Asp Leu Glu Leu Ile Val Asp
                130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Val Arg Lys Arg Glu
                165                 170                 175

Thr Ile Phe Ala Glu Phe Ile Phe Ser Ile His Pro Glu Tyr Lys Lys
                180                 185                 190

Thr Pro His Trp Phe Asp Arg Leu Asp Asn Gly Ser Ile Glu Gly Gly
                195                 200                 205

Asp Val Phe Ile Tyr Asn Lys Asp Thr Leu Val Ile Gly Val Ser Glu
                210                 215                 220

Arg Thr Asn Lys Glu Ala Ile Ile Thr Ile Ala Lys His Ile Gln Asp
225                 230                 235                 240

Asn Lys Glu Ala Gln Phe Lys Lys Ile Val Ala Ile Asn Val Pro Pro
                245                 250                 255
```

```
Met Pro Asn Leu Met His Leu Asp Thr Trp Leu Thr Met Val Asp Lys
            260                 265                 270

Asn Lys Phe Leu Tyr Ser Pro Asn Met Leu Ser Val Leu Lys Val Trp
        275                 280                 285

Glu Ile Asp Leu Ser Lys Pro Ile Glu Met Val Glu Thr Asn Lys Pro
    290                 295                 300

Leu Ala Glu Val Leu Glu Ser Ile Ile Gly Glu Lys Pro Ile Leu Ile
305                 310                 315                 320

Pro Ile Ala Gly Lys Asp Ala Thr Gln Leu Asp Ile Asp Ile Glu Thr
                325                 330                 335

His Phe Asp Gly Thr Asn Tyr Leu Thr Ile Ala Pro Gly Val Val Val
            340                 345                 350

Gly Tyr Ser Arg Asn Val Lys Thr Glu Ala Ala Leu Arg Ala Ala Gly
        355                 360                 365

Val Thr Val Leu Ser Phe Glu Gly Asn Gln Leu Ser Leu Gly Met Gly
    370                 375                 380

Ser Ala Arg Cys Met Ser Met Pro Leu Val Arg Glu Asp Val Lys
385                 390                 395

<210> SEQ ID NO 58
<211> LENGTH: 401
<212> TYPE: PRT
<213> ORGANISM: Artificial Sequence
<220> FEATURE:
<223> OTHER INFORMATION: C9DS4 recombinant chimeric ADI protein

<400> SEQUENCE: 58

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
        35                  40                  45

Gln Glu His Lys Ser Phe Leu Lys Ile Leu Gln Asp Arg Gly Ile Lys
    50                  55                  60

Thr Ile Gln Leu Ser Asp Leu Val Ala Glu Thr Tyr Thr Tyr His Ala
65                  70                  75                  80

Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
                100                 105                 110

Leu Ser Lys Glu Gly Thr Pro Val Ala Met Val Arg Thr Met Met Ala
            115                 120                 125

Gly Val Ser Lys Gln Glu Leu Asn Val Glu Ser Glu Thr Glu Leu Val
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
    210                 215                 220
```

```
Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
            245                 250                 255

Pro Pro Met Pro Asn Leu Met His Leu Asp Thr Trp Leu Thr Met Val
        260                 265                 270

Asp Lys Asn Lys Phe Leu Tyr Ser Pro Asn Met Leu Ser Val Leu Lys
        275                 280                 285

Val Trp Glu Ile Asp Leu Ser Lys Pro Ile Glu Met Val Glu Thr Asn
290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Val Lys Thr Glu Ala Ala Leu Arg Ala
            355                 360                 365

Ala Gly Val Thr Val Leu Ser Phe Glu Gly Asn Gln Leu Ser Leu Gly
370                 375                 380

Met Gly Ser Ala Arg Cys Met Ser Met Pro Leu Val Arg Glu Asp Val
385                 390                 395                 400

Lys

<210> SEQ ID NO 59
<211> LENGTH: 401
<212> TYPE: PRT
<213> ORGANISM: Artificial Sequence
<220> FEATURE:
<223> OTHER INFORMATION: C9DS8 recombinant chimeric ADI protein

<400> SEQUENCE: 59

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
        35                  40                  45

Gln Glu His Lys Ser Phe Leu Lys Ile Leu Gln Asp Arg Gly Ile Lys
    50                  55                  60

Thr Ile Gln Leu Ser Asp Leu Val Ala Glu Thr Tyr Val Lys Tyr Ala
65                  70                  75                  80

Thr Ala Glu Gln Lys Ala Ala Phe Ile Glu Lys Tyr Leu Asp Glu Ala
                85                  90                  95

Thr Pro Ala Leu Ser Ala Glu Asn Arg Glu Arg Ala Lys Lys Tyr Ile
            100                 105                 110

Leu Ser Leu Glu Met Gln Pro Val Lys Met Ile Arg Thr Met Met Ala
        115                 120                 125

Gly Leu Ser Lys Tyr Glu Leu Asn Val Glu Ser Asn Ile Glu Leu Ile
    130                 135                 140

Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
```

```
                    180                 185                 190
Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
        210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
            245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
            275                 280                 285

Val Trp Glu Ile Asp Leu Ser Lys Pro Ile Glu Met Val Glu Thr Asn
        290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
            325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
        355                 360                 365

Ala Gly Val Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400

Lys
```